(12) United States Patent
Copland, III et al.

(10) Patent No.: US 11,596,629 B2
(45) Date of Patent: Mar. 7, 2023

(54) COMPOUNDS AND METHODS FOR TREATING CANCER

(71) Applicant: Mayo Foundation for Medical Education and Research, Rochester, MN (US)

(72) Inventors: John A. Copland, III, Ponte Vedra Beach, FL (US); Christina Von Roemeling, Jacksonville, FL (US); Han W. Tun, Jacksonville, FL (US); Thomas R. Caulfield, Jacksonville, FL (US); Yon Son Kim, Jacksonville Beach, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 476 days.

(21) Appl. No.: 16/489,133

(22) PCT Filed: Feb. 28, 2018

(86) PCT No.: PCT/US2018/020257
§ 371 (c)(1),
(2) Date: Aug. 27, 2019

(87) PCT Pub. No.: WO2018/160717
PCT Pub. Date: Sep. 7, 2018

(65) Prior Publication Data
US 2020/0061055 A1    Feb. 27, 2020

Related U.S. Application Data

(60) Provisional application No. 62/465,062, filed on Feb. 28, 2017.

(51) Int. Cl.
| A61P 35/00 | (2006.01) |
| A61K 31/4545 | (2006.01) |
| A61K 39/395 | (2006.01) |
| C07K 16/28 | (2006.01) |
| A61K 39/00 | (2006.01) |
| A61K 31/496 | (2006.01) |
| A61K 31/495 | (2006.01) |

(52) U.S. Cl.
CPC ........ *A61K 31/496* (2013.01); *A61K 31/4545* (2013.01); *A61K 31/495* (2013.01); *A61K 39/39541* (2013.01); *A61P 35/00* (2018.01); *C07K 16/2818* (2013.01); *A61K 2039/505* (2013.01); *C07K 2317/24* (2013.01)

(58) Field of Classification Search
CPC ............. A61K 31/496; A61K 31/4545; A61K 31/495; A61K 39/39541; A61K 2039/505; A61K 45/06; A61K 39/39533; A61P 35/00; C07K 16/2818; C07K 2317/24; C07K 16/28
See application file for complete search history.

(56) References Cited

U.S. PATENT DOCUMENTS

| 6,066,730 | A | 5/2000 | Adams et al. |
| 6,297,217 | B1 | 10/2001 | Adams et al. |
| 6,548,668 | B2 | 4/2003 | Adams et al. |
| 6,699,835 | B2 | 3/2004 | Plamondon et al. |
| 7,014,866 | B2 | 3/2006 | Infeld et al. |
| 7,109,323 | B2 | 9/2006 | Plamondon et al. |
| 7,531,526 | B2 | 5/2009 | Adams et al. |
| 7,687,456 | B2 | 3/2010 | Zhou et al. |
| 7,691,852 | B2 | 4/2010 | Shenk et al. |
| 8,080,545 | B2 | 12/2011 | Shenk et al. |
| 8,080,576 | B2 | 12/2011 | Shenk et al. |
| 8,088,741 | B2 | 1/2012 | Smyth et al. |
| 8,357,683 | B2 | 1/2013 | Shenk et al. |
| 8,431,571 | B2 | 4/2013 | Shenk et al. |
| 9,233,102 | B2 | 1/2016 | Copland, III et al. |
| 10,301,273 | B2 * | 5/2019 | Copland, III ...... C07D 295/192 |
| 2006/0079502 | A1 | 4/2006 | Lang |
| 2006/0094744 | A1 | 5/2006 | Maryanoff et al. |
| 2013/0096181 | A1 | 4/2013 | Ashkenazi et al. |
| 2015/0218274 | A1 * | 8/2015 | Sabatos-Peyton ...... A61P 25/00 435/254.2 |
| 2016/0067336 | A1 | 3/2016 | Fand et al. |
| 2017/0015654 | A1 | 1/2017 | Imamura et al. |
| 2019/0302121 | A1 * | 10/2019 | Copland, III .... G01N 33/57484 |
| 2019/0345123 | A1 * | 11/2019 | Copland, III .......... A61K 45/06 |

FOREIGN PATENT DOCUMENTS

| WO | WO 2003/006009 | 1/2003 |
| WO | WO 2008/120759 | 10/2008 |
| WO | WO 2009/020448 | 2/2009 |
| WO | WO 2009/051581 | 4/2009 |
| WO | WO 2009/154737 | 12/2009 |
| WO | WO 2010/036357 | 4/2010 |
| WO | WO 2011/123502 | 10/2011 |
| WO | WO 2012/151451 | 11/2012 |
| WO | WO 2014/153150 | 9/2014 |
| WO | WO 2016/022955 | 2/2016 |
| WO | WO-2016022955 A1 * | 2/2016 ............. A61K 45/06 |
| WO | WO 2016/141299 | 9/2016 |
| WO | WO 2016/183326 | 11/2016 |

OTHER PUBLICATIONS

Jianli Wang, Scott Saffold, Xuetao Cao, John Krauss, Wei Chen, Eliciting T Cell Immunity Against Poorly Immunogenic Tumors by Immunization with Dendritic Cell-Tumor Fusion Vaccines, The Journal of Immunology, Nov. 15, 1998, 161 (10) 5516-5524 (Year: 1998).*

Mason P et al., SCD1 inhibition causes cancer cell death by depleting mono-unsaturated fatty acids. PLoS One. 2012;7(3):e33823. (Year: 2012).*

(Continued)

*Primary Examiner* — Hong Sang
*Assistant Examiner* — Sung Min Yoon
(74) *Attorney, Agent, or Firm* — Fish & Richardson P.C.

(57) ABSTRACT

The present application provides methods and compositions for treating cancer, for example, renal cell carcinoma, melanoma, ovarian, breast, prostate, colon, pancreatic, bladder, liver, lung, and thyroid cancer, and more particularly to using an inhibitor of a stearoyl-Coenzyme A desaturase 1 (SCD1) enzyme in combination with a checkpoint inhibitor to treat these disorders.

10 Claims, 53 Drawing Sheets

(56) References Cited

OTHER PUBLICATIONS

Le DT et al., PD-1 Blockade in Tumors with Mismatch-Repair Deficiency. N Engl J Med. Jun. 25, 2015;372(26):2509-20. (Year: 2015).*
Nanda et al., Pembrolizumab in Patients With Advanced Triple-Negative Breast Cancer: Phase Ib Keynote-012 Study, Journal of Clinical Oncology 34, No. 21 (Jul. 20, 2016) 2460-2467. (Year: 2016).*
Economopoulou P, Kotsantis I, Psyrri A. The promise of immunotherapy in head and neck squamous cell carcinoma: combinatorial immunotherapy approaches. ESMO Open. Feb. 13, 2017;1(6):e000122. doi: 10.1136/esmoopen-2016-000122. PMID: 28848660; PMCID: PMC5548974. (Year: 2017).*
U.S. Appl. No. 15/502,301, filed Feb. 7, 2017, John A. Copland III, Issued.
U.S. Appl. No. 16/422,519, filed May 24, 2019, John A. Copland III, Published.
U.S. Appl. No. 16/368,477, filed Mar. 28, 2019, John A. Copland III, Published.
Abramson, "The lipogenesis pathway as a cancer target," J. Med. Chem., 54(16):5615-38, Aug. 2011.
Ackerman and Simon, "Hypoxia, lipids, and cancer: surviving the harsh tumor microenvironment," Trends Cell Biol., 24(8):472-8, Aug. 2014.
Ahn, "An evaluation of phase I cancer clinical trial designs," Stat. Med., 17(14):1537-49, Jul. 1998.
Angelucci et al., "Stearoyl-CoA desaturase 1 and paracrine diffusible signals have a major role in the promotion of breast cancer cell migration induced by cancer-associated fibroblasts," Br. J. Cancer, 112(10):1675-86, Apr. 2015.
Aparicio et al., "Examining the utility of patient-derived xenograft mouse models," Nat. Rev. Cancer, 15(5):311-6, Apr. 2015.
Baenke et al., "Hooked on fat: the role of lipid synthesis in cancer metabolism and tumour development," Dis. Model Mech., 6(6):1353-63, Nov. 2013.
Bankaitis, "Unsaturated fatty acid-induced non-canonical autophagy: unusual? or unappreciated?" EMBO J., 34(8):978-80, Apr. 2015.
Bansal et al., "Stearoyl-CoA desaturase plays an important role in proliferation and chemoresistance in human hepatocellular carcinoma," J. Surg. Res., 186(1):29-38, Jan. 2014.
Beloribi-Djefaflia et al., "Lipid metabolic reprogramming in cancer cells," Oncogenesis, 5(1):e189, Jan. 2016.
Ben-David et al., "Selective Elimination of Human Pluripotent Stem Cells by an Oleate Synthesis Inhibitor Discovered in a High-Throughput Screen," Cell Stem Cell, 12(2):167-79, Feb. 2013.
Berge et al., "Pharmaceutical Salts", J Pharm Sci., 66(1):Jan. 1-19, 1977.
Böhm et al., "Scaffold hopping," Drug Discov Today: Technologies., 1(3):217-224, 2004.
Brown and Rudel, "Stearoyl-coenzyme A desaturase 1 inhibition and the metabolic syndrome: considerations for future drug discovery," Curr. Opin. Lipidol.. 21(3):192-7, Jun. 2010.
Cao et al., "Sphereforming cell subpopulations with cancer stem cell properties in human hepatoma cell lines," BMC Gastroenterol., 11(1):71, Jun. 2011.
Cassidy et al., "Maintaining Tumor Heterogeneity in Patient-Derived Tumor Xenografts," Cancer Res., 75(15):2963-8, Aug. 2015.
Caulfield et al., "Motion of transfer RNA from the A/T state into the A-site using docking and simulations," Proteins., 80(11):2489-2500, Nov. 2012.
Chajès et al., "Association between Serum trans-Monounsaturated Fatty Acids and Breast Cancer Risk in the E3N-EPIC Study," Am. J. Epidemiol., 167(11):1312-20, Apr. 2008.
Chajès et al., "Riboli E. Fatty-acid composition in serum phospholipids and risk of breast cancer: An incident case-control study in Sweden," Intern. J. Cancer, 83(5):585-90, Nov. 1999.
Chang et al., "KGF induces lipogenic genes through a PI3K and JNK/SREBP-1 pathway in H292 cells," J. Lipid Res., 46(12):2624-35, Dec. 2005.
Chou and Talalay, "Quantitative analysis of dose-effect relationships: the combined effects of multiple drugs or enzyme inhibitors," Adv. Enzyme Regul., 22:27-55, 1984.
Chou et al., "Analysis of combined drug effects: a new look at a very old problem," Trends in Pharmacological Sciences., 4(11):450-454, 1983.
Chou et al., "Computerized Quantitation of Synergism and Antagonism of Taxol, Topotecan, and Cisplatin Against Human Teratocarcinoma Cell Growth: a Rational Approach to Clinical Protocol Design," J. Natl. Cancer Inst., 86(20):1517-24, Oct. 1994.
Chou, "Drug Combination Studies and Their Synergy Quantification Using the Chou-Talalay Method," Cancer Res., 70(2):440-6, Jan. 2010.
Chow et al., "The Enhanced Metastatic Potential of Hepatocellular Carcinoma (HCC) Cells with Sorafenib Resistance," PLoS ONE, 8(11):e78675, Nov. 2013.
Conway et al., "Xenome—a tool for classifying reads from xenograft samples," Bioinformatics, 28(12):i172-8, Jun. 2012.
Cooper et al., "Current status of biomarker discovery in human clear cell renal cell carcinoma," J. Mol. Biomark Diagn., S2:1-10, 2012.
Copland et al., "Novel high-affinity PPARgamma agonist alone and in combination with paclitaxel inhibits human anaplastic thyroid carcinoma tumor growth via p21WAF1/CIP1," Oncogene., 25(16):2304-2317, Apr. 13, 2006.
Costello B. Navitoclax and Sorafenib Tosylate in Treating Patients with Relapsed or Refractory Solid Tumors.[http://www.cancer.gov/about-cancer/treatment/clinicaltrials/search/view?cdrid=761522&version=HealthProfessional&protocolsearchid=8215330 ]; 2014 [NCT02143401].
Currie et al., "Cellular Fatty Acid Metabolism and Cancer," Cell Metabolism, 18(2):153-61, Aug. 2013.
Database accession No. 1390035-79-6, [online] "1-Piperazinecarboxamide, 4-benzoyl-N-[2-[[(1,1-dimethylethyl)amino]carbonyl]phenyl]-," Aug. 12, 2012, Abstract Only, 1 page.
Demoulin et al., "Platelet-derived Growth Factor Stimulates Membrane Lipid Synthesis Through Activation of Phosphatidylinositol 3-Kinase and Sterol Regulatory Element-binding Proteins," J. Biol. Chem., 279(34):35392-402, Aug. 2004.
Dholaria et al., "Emerging therapeutic agents for lung cancer," Journal of hematology & oncology, 9(1):138, Dec. 2016.
Du et al., "FGFR3 Stimulates Stearoyl CoA Desaturase-1 Activity to Promote Bladder Tumor Growth," Cancer Res., 72(22):5 843-55, Nov. 2012.
Du Manoir et al., "Breast tumor PDXs are genetically plastic and correspond to a subset of aggressive cancers prone to relapse," Mol. Oncol., 8(2):431-43, Mar. 2014.
Einarsdottir et al., "Melanoma patient-derived xenografts accurately model the disease and develop fast enough to guide treatment decisions," Oncotarget, 5(20):9609-18, Oct. 2014.
Falvella et al., "Stearoyl-CoA desaturase 1 (Scd1) gene overexpression is associated with genetic predisposition to hepatocarcinogenesis in mice and rats," Carcinogenesis, 23(11): 1933-6, Nov. 2002.
Friesner et al., "Extra Precision Glide: Docking and Scoring Incorporating a Model of Hydrophobic Enclosure for Protein-Ligand Complexes," Journal of medicinal chemistry., 49(21):6177-6196, Oct. 19, 2006.
Fritz et al., "Abrogation of De novo Lipogenesis by Stearoyl-CoA Desaturase 1 Inhibition Interferes with Oncogenic Signaling and Blocks Prostate Cancer Progression in Mice," Mol. Cancer Therapy., 9(6):1740-54, Jun. 2010.
Fu et al., "Discovery of new non-steroidal FXR ligands via a virtual screening workflow based on Phase shape and induced fit docking," Bioorg Med Chem Lett., 22(22):6848-6853, Nov. 15, 2012.
Fucikova et al., "Prognostic and predictive value of DAMPs and DAMP-associated processes in cancer," Front Immunol., 6:402, Aug. 2015.
Gao et al., "High-throughput screening using patient-derived tumor xenografts to predict clinical trial drug response," Nat. Med., 21(11):1318-25, Oct. 2015.

(56) References Cited

OTHER PUBLICATIONS

GenBank® Accession No. AF097514.1 (GI No. 4808600), "Homo sapiens stearoyl-CoA desaturase (SCD) mRNA, complete cds," May 19, 1999, 2 pages.
GenBank® Accession No. O00767 (GI No. 21431730), "Acyl-CoA desaturase," Jul. 15, 1998, 11 pages.
Goldberg and Drake, "LAG-3 in Cancer Immunotherapy," Curr. Top Microbiol. Immunol., 344:269-78, Nov. 2010.
Goodman et al., "Some practical improvements in the continual reassessment method for phase I studies," Stat. Med., 14(11):1149-61, Jun. 1995.
Gu et al., Autophagyrelated prognostic signature for breast cancer. Mol. Carcinogenesis, 55(3):292-9, Mar. 2016.
Guillou et al., "The key roles of elongases and desaturases in mammalian fatty acid metabolism: Insights from transgenic mice," Prog Lipid Res., 49(2):186-199, Apr. 2010.
Guo et al., "EGFR Signaling Through an Akt-SREBP-1-Dependent, Rapamycin-Resistant Pathway Sensitizes Glioblastomas to Antilipogenic Therapy," Sci. Signal., 2(101):ra82, Dec. 2009.
Guo et al., "Therapeutic cancer vaccines: past, present, and future," Adv. Cancer Res., 119:421-75, Jan. 2013.
Halgren., "Identifying and characterizing binding sites and assessing druggability," J Chem Inf Model., 49(2):377-389, Feb. 2009.
Halgren., "New method for fast and accurate binding-site identification and analysis," Chem Biol Dru Des., 69(2):146-148, Feb. 2007.
Hanahan and Weinberg, "Hallmarks of cancer: the next generation," Cell, 144(5):646-74, Mar. 2011.
Heitjan, "Biology, Models, and the Analysis of Tumor Xenograft Experiments," Clin. Cancer Res., 17(5):949-52, Jan. 2011.
Herr et al., "Drop-off during ribosome hopping," J Mol Biol., 311(3):445-452, Aug. 17, 2001.
Hess et al., "Inhibition of StearoylCoA Desaturase Activity Blocks Cell Cycle Progression and Induces Programmed Cell Death in Lung Cancer Cells," PLoS One, 5(6):e11394, Jun. 2010.
Hetz et al., "Targeting the unfolded protein response in disease," Nat Rev Drug Discov., 12(9):703-719, Sep. 2013.
Hidalgo et al., "Patient-Derived Xenograft Models: An Emerging Platform for Translational Cancer Research," Cancer Disc., 4(9):998-1013, Sep. 2014.
Hockla et al., "PRSS3/Mesotrypsin Is a Therapeutic Target for Metastatic Prostate Cancer," Mol. Cancer Res., 10(12):1555-66, Dec. 2012.
Holland et al., "Wnt signaling in stem and cancer stem cells," Curr. Opin. Cell Biol,, 25(2):254-64., Apr. 2013.
Huang et al., "SCD1 negatively regulates autophagy-induced cell death in human hepatocellular carcinoma through inactivation of the AMPK signaling pathway," Cancer Lett., 358(2):180-90, Mar. 2015.
Huard et al., "Cellular expression and tissue distribution of the human LAG-3-encoded protein, an MHC class II ligand," Immunogenetics, 39(3):213-217, Jan. 1994.
Ide et al., "Human breast cancer tissues contain abundant phosphatidylcholine (36:1) with high stearoyl-CoA desaturase-1 expression," PLoS One, 8(4):e61204, 2013.
Igai, "Stearoyl-CoA desaturase-1: a novel key player in the mechanisms of cell proliferation, programmed cell death and transformation to cancer," 31(9):1509-15, Jul. 2010.
International Preliminary Report on Patentability in International Application No. PCT/US2018/020257 dated Sep. 12, 2019, 11 pages.
International Search Report & Written Opinion in International Application No. PCT/US2018/020257 dated May 14, 2018, 16 pages.
Izuishi et al., "Remarkable tolerance of tumor cells to nutrient deprivation: possible new biochemical target for cancer therapy," Cancer Res., 60(21):6201-7, Nov. 2000.
Janssens et al., "Emerging functions of the unfolded protein response in immunity," Nat. Immunol., 15(10):910-9, Oct. 2014.
Jemal et al., "Global cancer statistics," CA Cancer J. Clin., 61(2):69-90, Feb. 2011.
Jorgensen et al., "The OPLS [optimized potentials for liquid simulations] potential functions for proteins, energy minimizations for crystals of cyclic peptides and crambin," J Am Chern Soc., 110(6):1657-1666, Mar. 1, 1988.
Kalari et al., "MAP-RSeq: Mayo Analysis Pipeline for RNA sequencing," BMC Bioinformatics, 15(1):1-11, Jun. 2014.
Kalid et al., "Consensus Induced Fit Docking (cIFD): methodology, validation, and application to the discovery of novel Crm1 inhibitors," J Comput Aided Mol Des., 26(11): 1217-1228, Nov. 2012.
Kim et al., "Cell death and endoplasmic reticulum stress: disease relevance and therapeutic opportunities," Nat Rev Drug Discov., 7(12):1013-1030, Dec. 2008.
Kim et al., "Stearoyl CoA desaturase (SCD) facilitates proliferation of prostate cancer cells through enhancement of androgen receptor transactivation," Mol. Cells, 31(4):371-7, Apr. 2011.
Koltun et al., "Novel, potent, selective, and metabolically stable stearoyl-CoA desaturase (SCD) inhibitors," Bioorganic Medicinal Chem Lett., 19(7):2048-2052, Apr. 1, 2009.
Krieger et al., "Assignment of protonation states in proteins and ligands: combining pKa prediction with hydrogen bonding network optimization.," Methods Mol Biol., 819:405-421, 2012.
Krieger et al., "Improving physical realism, stereochemistry, and side-chain accuracy in homology modeling: Four approaches that performed well in CASP8," Proteins., 77(Suppl S9): 114-122, 2009.
Kuhajda et al., "Fatty acid synthesis: a potential selective target for antineoplastic therapy," Proc. Natl. Acad. Sci. USA, 91(14):6379-83, 1994.
Kupershmidt et al., Ontology-based meta-analysis of global collections of high-throughput public data, PLoS One., 5(9):e13066, 13 pages Sep. 2010.
Lee et al., "Nutrient-sensing nuclear receptors coordinate autophagy," Nature, 516(7529):112-5, Nov. 2014.
Lee et al., Patient-Derived Xenografts from Non-Small Cell Lung Cancer Brain Metastases Are Valuable Translational Platforms for the Development of Personalized Targeted Therapy. Clin. Cancer Res., 21(5):1172-82, Mar. 2015.
Leger et al., "Synthesis and biological activity of a potent and orally bioavailable SCD inhibitor (MF-438)," Bioorg Med Chem Lett., 20(2):499-502, Jan. 15, 2010.
Leung and Kim, "Stearoyl Co-A Desaturase 1 as a ccRCC Therapeutic Target: Death by Stress," Clin, Cancer Res., 19(12):1-3, May 2013.
Li et al., "Endocrine-Therapy-Resistant ESRI Variants Revealed by Genomic Characterization of Breast-Cancer-Derived Xenografts," Cell Reports, 4(6):1116-30, Sep. 2013.
Li et al., "SCD1 expression is dispensable for hepatocarcinogenesis induced by AKT and ras oncogenes in mice," Plos one., 8(9):e75104, Sep. 19, 2013, 12 pages.
Li et al., "Targeted hepatocellular carcinoma proapoptotic BikDD gene therapy," Oncogene, 30(15):1773-83, 2011.
Li et al., "Thiazole analog as stearoyl-CoA desaturase 1 inhibitor," Bioorg Med Chem Lett., 19(17):5214-5217, Epub Jul. 9, 2009.
Liang and Sha, "Modeling antitumor activity by using a non-linear mixed-effects model," Math, Biosci., 189(1):61-73, May 2004.
Liu et al., "Discovery of potent, selective, orally bioavailable stearoyl-CoA desaturase 1 inhibitors," J Med Chem., 50(13):3086-3100, Jun. 28, 2007.
Liu., "Stearoyl-CoA desaturase inhibitors: update on patented compounds," Expert Opin Ther Pat., 19(9):1169-1191, 2009.
Llovet et al., "Sorafenib in Advanced Hepatocellular Carcinoma," N. Engl. J. Med., 359(4):378-90, Jul. 2008.
Loving et al., "Energetic analysis of fragment docking and application to structure-based pharmacophore hypothesis generation," J computer-aided molecular design., 23(8):541-554, Aug. 2009.
Luyimbazi et al., "Rapamycin regulates stearoyl CoA desaturase 1 expression in breast cancer," Mol, Cancer Ther., 9(10):2770-84, Oct. 2010.
Marlow et al., "Detailed molecular fingerprinting of four new anaplastic thyroid carcinoma cell lines and their use for verification of RhoB as a molecular therapeutic target," J Clin Endocrinol Metab., 95(12):5338-5347, 2010.

(56) References Cited

OTHER PUBLICATIONS

Marlow et al., "FoxO3a drives proliferation in anaplastic thyroid carcinoma through transcriptional regulation of cyclin A1: a paradigm shift that impacts current therapeutic strategies," J. Cell Sci., 125(18):4253-63, Sep. 2012.

Mason et al., "SCD1 Inhibition Causes Cancer Cell Death by Depleting Mono-Unsaturated Fatty Acids," PLoS ONE, 7(3):e33823, Mar. 2012.

Mauvoisin et al., "Decreasing stearoyl-CoA desaturase-1 expression inhibits β-catenin signaling in breast cancer cells," Cancer Sci., 104(1):36-42, Jan. 2013.

MedicineNet.com (http://www.medterms.com, 2004).

Mellman et al., "Cancer immunotherapy comes of age," Nature, 480(7378):480-9, Dec. 2011.

Menendez and Lupu, "Fatty acid synthase and the lipogenic phenotype in cancer pathogenesis," Nat. Rev. Cancer, 7(10):763-77, Oct. 2007.

Minville-Walz et al., "Inhibition of Stearoyl-CoA Desaturase 1 Expression Induces CHOP-Dependent Cell Death in Human Cancer Cells," PLoS One, 5(12):e14363, Dec. 2010.

Mohamadi et al., "Macromodel-an integrated software system for modeling organic and bioorganic molecules using molecular mechanics," J Comput Chem., 11(4):440-467, May 1990.

Monsma et al., "Using a rhabdomyosarcoma patient-derived xenograft to examine precision medicine approaches and model acquired resistance," Pediatr. Blood Cance, 61(9):1570-7, Mar. 2014.

Mounier et al., "Lipogenesis in cancer progression (review)," Int. J. Oncol., 45:485-92, May 2014.

Muir et al., "Proteomic and Lipidomic Signatures of Lipid Metabolism in NASH-Associated Hepatocellular Carcinoma," Cancer Res., 73(15):4722-31, Aug. 2013.

Naugler et al., "Gender Disparity in Liver Cancer Due to Sex Differences in MyD88-Dependent IL-6 Production," Science, 317(5834):121-4, Jul. 2007.

Nelson et al., "Transcriptional changes associated with reduced spontaneous liver tumor incidence in mice chronically exposed to high dose arsenic," Toxicol., 266(1-3):6-15, Dec. 2009.

Nile and Hannoush, "Fatty acylation of Wnt proteins," Nat. Chem. Biol., 12(2):60-9, Jan. 2016.

Niso-Santano et al., "Unsaturated fatty acids induce non-canonical autophagy," EMBO J., 34(8):1025-41, Jan. 2015.

Noto et al., "Stearoyl-CoA desaturase-1 is a key factor for lung cancer-initiating cells," Cell Death Dis., 4(12):e947, Dec. 2013.

Oballa et al., "Development of a liver-targeted stearoyl-CoA desaturase (SCD) inhibitor (MK-8245) to establish a therapeutic window for the treatment of diabetes and dyslipidemia," J Med Chem., 54(14):5082-5096, Epub Jun. 28, 2011.

Oesterreich et al., "Using Mice to Treat (Wo)men: Mining Genetic Changes in Patient Xenografts to Attack Breast Cancer," Cell Reports, 4(6):1061-2, Sep. 2013.

Okuda, "Epidemiology of primary liver cancer," Primary Liver Cancer in Japan, Tobe T (ed)., Chapter 1, pp. 3-15, 1992.

O'Quigley et al., "Continual reassessment method: a practical design for phase 1 clinical trials in cancer," Biometrics, 46(1):33-48, Mar. 1990.

Pala et al., "Erythrocyte Membrane Fatty Acids and Subsequent Breast Cancer: a Prospective Italian Study," J. Natl. Cancer Institute, 93(14):1088-95, Jul. 2001.

Pala et al., "Structure-Based Virtual Screening of MT2 Melatonin Receptor: Influence of Template Choice and Structural Refinement," J Chem Inf Model., 53(4):821-835, Mar. 29, 2013.

Panaretakis et al., "Mechanisms of pre-apoptotic calreticulin exposure in immunogenic cell death," EMBO J., 28(5):578-90, Mar. 2009.

Patani and LaVoie, "Bioisosterism: A Rational Approach in Drug Design," Chem. Rev., 96(8):3147-3176, 1996.

Paton and Ntambi, "Biochemical and physiological function of stearoyl-CoA desaturase," Am. J. Physiol. Endocrinol. Metab., 297(1):E28-37, Jul. 2009.

Petrek et al., "Fatty acid composition of adipose tissue, an indication of dietary fatty acids, and breast cancer prognosis," J. Clin. Oncol., 15(4):1377-84, Apr. 1997.

Petrova et al., "TTI-621 (SIRPαFc): a CD47-blocking innate immune checkpoint inhibitor with broad antitumor activity and minimal erythrocyte binding," Clinical Cancer Research, 23(4):1068-79, Feb. 2017.

Porstmann et al., "PKB//Akt induces transcription of enzymes involved in cholesterol and fatty acid biosynthesis via activation of SREBP," Oncogene, 24(43):6465-81, Jun. 2005.

Porstmann et al., "SREBP Activity Is Regulated by mTORC1 and Contributes to Akt-Dependent Cell Growth," Cell Metab., 8(3):224-36, Sep. 2008.

Powell et al., "2-Aryl benzimidazoles: human SCD1-specific stearoyl coenzyme-A desaturase inhibitors," Bioorg Med Chem Lett., 20(22):6366-6369, Nov. 15, 2010.

Powers, "Cell Growth Control: mTOR Takes on Fat," Mol. Cell, 31(6):775-6, Sep. 2008.

Pubchem, Substance Record for SID 144964572, AKOS008653309, Available Oct. 18, 2012, retrieved on Oct. 30, 2015, Retrieved from the Internet, URL: https://pubchem.ncbi.nlm.nih.gov/substance/144964572/version/1>, 6 pages.

Rathert et al., "Transcriptional plasticity promotes primary and acquired resistance to BET inhibition.," Nature, 525(7570):543-7, Sep. 2015.

Reya and Clevers, "Wnt signalling in stem cells and cancer," Nature, 434(7035):843-50, Apr. 2005.

Rodvoid et al., "Immune modulation by ER stress and inflammation in the tumor microenvironment," Cancer Letters, 380(1):227-36, Sep. 2016.

Roemeling et al., "Aberrant lipid metabolism in anaplastic thyroid carcinoma reveals stearoyl CoA desaturase 1 as a novel therapeutic target," J. Clin. Endocrinol, Metab., 100(5): E697-E709, May 2015.

Roemeling et al., "Stearoyl-CoA Desaturase 1 Is a Novel Molecular Therapeutic Target for Clear Cell Renal Cell Carcinoma", Clin Canc Res., 19(9):2368-2380, Apr. 30, 2013.

Roongta et al., "Cancer cell dependence on unsaturated fatty acids implicates stearoyl-CoA desaturase as a target for cancer therapy," Mol Cancer Res., 9(11):1551-1561, Nov. 2011.

Rosenberg, "Raising the bar: the curative potential of human cancer immunotherapy," Sci. Transl. Med., 4(127):127ps8, Mar. 2012.

Ruddigkeit et al., "Visualization and virtual screening of the chemical universe database GDB-17," J Chem Inf Model., 53(1):56-65, Dec. 23, 2012.

Rysman et al., "De novo lipogenesis protects cancer cells from free radicals and chemotherapeutics by promoting membrane lipid saturation," Cancer Res., 70(20):8117-26, Oct. 2010.

Sampath and Ntambi, "The role of stearoyl-CoA desaturase in obesity, insulin resistance, and inflammation," Ann. N.Y Acad. Sci., 1243(1):47-53, Dec. 2011.

Sandor et al., "Virtual Fragment Docking by Glide: a Validation Study on 190 Protein-Fragment Complexes," J Chem Inf Model., 50(6):1165-1172, Jun. 2010.

Santos and Schulze, "Lipid metabolism in cancer," FEBS J., 279(15):2610-23, Aug. 2012.

Sastry et al., "Boosting Virtual Screening Enrichments with Data Fusion: Coalescing Hits from Two-Dimensional Fingerprints, Shape, and Docking," J Chem Inf Model., 53(7):1531-1542, 2013.

Sastry et al., "Rapid Shape-Based Ligand Alignment and Virtual Screening Method Based on Atom/Feature-Pair Similarities and Volume Overlap Scoring ," J Chem Inf Model., 51(10):2455-2466, Sep. 15, 2011.

Scaglia et al., "Inhibition of StearoylCoA Desaturase-1 Inactivates Acetyl-CoA Carboxylase and Impairs Proliferation in Cancer Cells: Role of AMPK," PLoS One, 4(8):e6812, Aug. 2009.

Schlaepfer et al., "Progestin modulates the lipid profile and sensitivity of breast cancer cells to docetaxel," Mol. Cell. Endocrin., 363(1-2):111-21, Aug. 2012.

Schmittgen et al., "Analyzing real-time PCR data by the comparative C(T) method," NatProtoc., 3(6): 1101-1108, 2008.

Seok et al., "Transcriptional regulation of autophagy by an FXR-CREB axis," Nature, 516(7529):108-11, Dec. 2014.

(56) References Cited

OTHER PUBLICATIONS

Siolas and Hannon, "Patient-Derived Tumor Xenografts: Transforming Clinical Samples into Mouse Models," Cancer Res., 73(17):5315-9, Sep. 2013.
Song et al., "Hypoxia-induced autophagy contributes to the chemoresistance of hepatocellular carcinoma cells," Autophagy, 5(8):1131-44, Nov. 2009.
Sorafenib Package Insert and Prescribing Information. 2010.
Sperandio et al., "MED-SuMoLig: A New Ligand-Based Screening Tool for Efficient Scaffold Hopping," J Chem Inf Model., 47(3):1097-1110, 2007.
Sun, "Classification of scaffold-hopping approaches," Drug discovery today., 17(7-8):310-324, Apr. 2012.
Tun et al., "Pathway signature of clear cell renal cell carcinoma," PLoS One, 5:e10696, May 2010.
Tusher et al., "Significance analysis of microarrays applied to the ionizing radiation response," Proc. Natl. Acad. Sci. USA, 98(9):5116-21, Apr. 2001.
Uto et al., "Discovery of novel SCD1 inhibitors: 5-Alkyl-4,5-dihydro-3H-spiro[1,5-benzoxazepine-2,4'-piperidine] analogs," Eur J Med Chem., 46(5):1892-1896, May 2011.
Uto et al., "Synthesis and evaluation of novel stearoyl-CoA desaturase 1 inhibitors: 1'-{6-[5-(pyridin-3-ylmethyl)-1,3,4-oxadiazol-2-yl]pyridazin-3-yl}-3,4-dihydrospiro[chromene-2,4'-piperidine] analogs," Eur J Med Chem., 45(11):4788-4796, Nov. 2010.
Vivoli et al., "Inhibition of Prohormone Convertases PC1/3 and PC2 by 2,5-Dideoxystreptamine Derivatives," Mol Pharmacol., 81(3):440-454, Mar. 2012.
Von Roemeling and Copland, "Targeting lipid metabolism for the treatment of anaplastic thyroid carcinoma," Expert Opin. Ther. Targets, 20(2):159-66, Sep. 2015.
Von Roemeling et al, "Aberrant Lipid Metabolism in Anaplastic Thyroid Carcinoma Reveals Stearoyl CoA Desaturase 1 as a Novel Therapeutic Target," J. Clin. Endocrinol. Metab., 100(5):E697-709, May 2015.
Von Roemeling et al., "Functional genomics identifies novel genes essential for clear cell renal cell carcinoma tumor cell proliferation and migration," Oncotarget, 5(14):5320-34, Jun. 2014.
Von Roemeling et al., "Neuronal Pentraxin 2 is a regulator of clear cell renal cell carcinoma malignancy through activation of the AMPA-selective glutamate receptor-4," Cancer Res., 75(17):4796-810, Jun. 2014.
Von Roemeling et al., "Stearoyl-CoA Desaturase 1 Is a Novel Molecular Therapeutic Target for Clear Cell Renal Cell Carcinoma," Clin. Cancer Res., 19(9):2368-80, May 2013.
Voss et al., "Discovery and pharmacological characterization of SAR707 as novel and selective small molecule inhibitor of stearoyl-CoA desaturase (SCD1)," Eur. J. Pharmacol.,. 707(1-3): 140-6, May 2013.
Walter., "The unfolded protein response: from stress pathway to homeostatic regulation," Science., 334(6059):1081-1086, Nov. 25, 2011.
Wang and Shen et al., "Activation of ATF6 and an ATF6 DNA binding site by the endoplasmic reticulum stress response," J Biol Chem., 275(35):27013-27020, Sep. 1, 2000.
Watts et al., "A Conformational Search Method for Efficient Generation of Bioactive Conformers," J Chem Inf Model., 50(4):534-546, Apr. 26, 2010.
Whittle et al., "Patient-derived xenograft models of breast cancer and their predictive power," Breast Cancer Res., 17(1):17, Feb. 2015.
Woo et al., "Innate immune recognition of cancer," Annual review of immunology, 33:445-74, Mar. 2015.
Wu and Irizarry, "Preprocessing of oligonucleotide array data," Nat. Biotechnol., 22(6):656-8, Jun. 2004.

Xin et al., "Discovery of piperidine-aryl urea-based stearoyl-CoA desaturase 1 inhibitors," Bioorg Med Chem Lett., 18(15):4298-4302, Aug. 1, 2008.
Xu et al., "Endoplasmic reticulum stress: cell life and death decisions," J Clin Invest., 115(10):2656-2664, Oct. 2005.
Yahagi et al., "Co-ordinate activation of lipogenic enzymes in hepatocellular carcinoma," European Journal of Cancer, 41(9):1316-22, Jun. 2005.
Zhang and Du, "Dysregulated lipid metabolism in cancer," World journal of biological chemistry, 3(8):167, Aug. 2012.
Zhang et al., "Positive feedback loop and synergistic effects on promoting tumorigenesis between HIF-2α and SCD1 in clear cell renal cell carcinoma," Cancer Sci., 104:416-22, Apr. 2013.
Zhang et al., "Proteomic Study Reveals That Proteins Involved in Metabolic and Detoxification Pathways Are Highly Expressed in HER-2/neu-positive Breast Cancer," Mol. Cell. Proteomics, 4(11):1686-96, Nov. 2005.
Zhang et al., "Screening of kinase inhibitors targeting BRAF for regulating autophagy based on kinase pathways," Mol. Med. Rep., 9(1):83-90, Jan. 2014.
Zhao et al., "Bayesian Hierarchical Changepoint Methods in Modeling the Tumor Growth Profiles in Xenograft Experiments," Clin. Cancer Res., 17(5):1057-64, Mar. 2011.
Zhou., "Improving threading algorithms for remote homology modeling by combining fragment and template comparisons," Proteins., 78(9):2041-2048, Jul. 2010.
Zhou., "Protein structure prediction by Pro-Sp3-TASSER," Biophys J., 96(6):2119-2127, Mar. 2009.
Zhou., "Template-based protein structure modeling using TASSER(VMT)," Proteins., 80(22);352-361, Feb. 2012.
Zureik et al., "Fatty acid proportions in cholesterol esters and risk of premature death from cancer in middle aged French men," BMJ. 311(7015):1251-4, Aug. 1995.
Chen et al., "Targeting oncogenic Myc as a strategy for cancer treatment," Signal transduction and targeted therapy, 3(1):1-7, Feb. 2018.
Ma, Kin Fai, et al. "Stearoyl-CoA Desaturase (SCD1) regulates liver tumor initiating cells through modulating ER stress," Cancer Res., 77(13):A4772, 2017. (Abstract).
Ma et al., "Stearoyl-CoA desaturase regulates sorafenib resistance via modulation of ER stress-induced differentiation," Journal of hepatology, 67(5):979-90, Nov. 2017.
Wurz et al., "Novel cancer antigens for personalized immunotherapies: latest evidence and clinical potential," Ther. Adv. Med. Oncology, 8(1):4-31, Jan. 2016.
Brown "Bioisosterism in Medicinal Chemistry", 2012, Wiley-VCH Verlag GmbH & Co. KGaA, pp. 1-14 (Year: 2012).
Koltun et al., "Orally bioavailable, liver-selective stearoyl-CoA desaturase (SCD) inhibitors," Bioorg. Med. Chem. Letters, Apr. 8, 2009, 19(11):3050-3053.
Koltun et al., "Potent, orally bioavailable, liver-selective stearoyl-CoA desaturase (SCD) inhibitors," Bioorg. Med. Chem. Letters, Jun. 13, 2009, 19(15):4070-4074.
Uto et al., "Novel and potent inhibitors of stearoyl-CoA desaturase-1. Part I: Discovery of 3-(2-hydroxyethoxy)-4-methoxy-N-[5-(3-trifluoromethylbenzyl)thiazol-2-yl]benzamide," Bioorg. Med. Chem. Letters, Jun. 2, 2009, 19(15):4151-4158.
Uto et al., "Novel and potent inhibitors of stearoyl-CoA desaturase-1. Part II: Identification of 4-ethylamino-3-(2-hydroxyethoxy)-N-[5-(3-trifluoromethylbenzyl)thiazol-2-yl]benzamide and its biological evaluation," Bioorg. Med. Chem. Letters, Jun. 6, 2009, 19(15):4159-4166.
Von Roemeling et al., "Accelerated bottom-up drug design platform enables the discovery of novel stearoyl-CoA desaturase 1 inhibitors for cancer therapy," Oncotarget, Oct. 6, 2017, 9(1):3-20.

* cited by examiner

COMPOUNDS AND METHODS FOR TREATING CANCER

CLAIM OF PRIORITY

This application is a National Stage application under 35 U.S.C. § 371 International Application No. PCT/US2018/020257, having an International Filing Date of Feb. 28, 2018, which claims the benefit of U.S. Provisional Application No. 62/645,062, filed Feb. 28, 2017. The entire contents of the foregoing are hereby incorporated by reference.

TECHNICAL FIELD

This document relates to methods and compositions for treating cancer, for example, renal cell carcinoma, melanoma, ovarian, breast, prostate, colon, pancreatic, bladder, liver, lung, and thyroid cancer, and more particularly to using one or more inhibitors of a stearoyl-Coenzyme A desaturase 1 (SCD1) enzyme in combination with one or more checkpoint inhibitors to treat these disorders.

BACKGROUND

SCD1 is an enzyme that catalyzes the de novo lipogenesis of Δ-9 monounsaturated fatty acids (MUFA) oleic acid (OA) and palmitoleic acid (PA). These MUFAs are essential for the synthesis of triglycerides, sphingolipids, ceramides, glycolipids, phospholipids, and other lipoproteins which influence membrane fluidity, membrane raft formation and receptor clustering, second messenger signaling, fatty acid oxidation, energy storage, cell division, inflammation, and a number of other biological functions. SCD1 has been implicated as pro-tumorigenic in a multitude of cancers, such as clear cell renal cell carcinoma (ccRCC).

SUMMARY

Agents that specifically target crucial metabolic enzymes utilized by cancer have been actively investigated. However, it is unclear whether inhibition of fatty acid metabolism in tumors affects their immunogenicity. The present application shows that inhibition, e.g., of stearoyl-CoA desaturase 1 (SCD1), a key enzyme involved in fatty-acid synthesis and a potential prognostic marker for human cancers, increases the immunogenic susceptibility of cells and tumors, e.g., poorly immunogenic tumors. Inhibition of SCD1 can increase both recruitment and activation of immune cells in vivo, which when combined with PD-1 blockade can result in potent and durable anti-tumor T cell responses. Inhibition of tumorigenic de novo lipogenesis represents a novel approach to enhance T cell based cancer immunotherapy such as checkpoint inhibitor therapy.

In a first general aspect, the present application provides a method of treating cancer in a subject, the method comprising administering to the subject a therapeutically effective amount of an inhibitor of de novo lipogenesis, or a pharmaceutically acceptable salt thereof, and a therapeutically effective amount of a checkpoint inhibitor, or a pharmaceutically acceptable salt thereof.

In some embodiments, the checkpoint inhibitor is a programmed cell death protein-1 (PD-1) inhibitor.

In some embodiments, the checkpoint inhibitor is an inhibitor of programmed death-ligand-1 (PD-L1) or programmed death-ligand-2 (PD-L2).

In some embodiments, the checkpoint inhibitor is an inhibitor of cytotoxic T-lymphocyte-associated protein-4 (CTLA-4).

In some embodiments, the checkpoint inhibitor is an inhibitor of T-cell immunoglobulin and mucin-domain containing-3 (TIM-3).

In some embodiments, the checkpoint inhibitor is an antibody.

In some embodiments, the antibody is monoclonal.

In some embodiments, the checkpoint inhibitor is pembrolizumab.

In some embodiments, the checkpoint inhibitor is nivolumab.

In some embodiments, the checkpoint inhibitor is atezolizumab.

In some embodiments, the checkpoint inhibitor is ipilimumab.

In some embodiments, the checkpoint inhibitor is TSR-022.

In some embodiments, the inhibitor of de novo lipogenesis is administered with at least two checkpoint inhibitors.

In some embodiments, the at least two checkpoint inhibitors are selected from the group consisting of: pembrolizumab, nivolumab, atezolizumab, ipilimumab, and TSR-022.

In some embodiments, the inhibitor of de novo lipogenesis is administered with at least three checkpoint inhibitors.

In some embodiments, the at least three checkpoint inhibitors are selected from the group consisting of: pembrolizumab, nivolumab, atezolizumab, ipilimumab, and TSR-022.

In some embodiments, the inhibitor of de novo lipogenesis, or a pharmaceutically acceptable salt thereof, and the checkpoint inhibitor, or a pharmaceutically acceptable salt thereof, are admixed prior to administration.

In some embodiments, the inhibitor of de novo lipogenesis, or a pharmaceutically acceptable salt thereof, and the checkpoint inhibitor, or a pharmaceutically acceptable salt thereof, are administered concurrently.

In some embodiments, the inhibitor of de novo lipogenesis, or a pharmaceutically acceptable salt thereof, and the checkpoint inhibitor, or a pharmaceutically acceptable salt thereof, are administered sequentially.

In some embodiments, the inhibitor of de novo lipogenesis, or a pharmaceutically acceptable salt thereof, is administered prior to the administration of the checkpoint inhibitor, or a pharmaceutically acceptable salt thereof.

In some embodiments, the checkpoint inhibitor, or a pharmaceutically acceptable salt thereof, is administered prior to the administration of the inhibitor of de novo lipogenesis, or a pharmaceutically acceptable salt thereof.

In some embodiments, the inhibitor of de novo lipogenesis, or a pharmaceutically acceptable salt thereof, is administered orally.

In some embodiments, the checkpoint inhibitor, or a pharmaceutically acceptable salt thereof, is administered intravenously.

In some embodiments, the inhibitor of de novo lipogenesis, or a pharmaceutically acceptable salt thereof, is administered in an amount from about 200 mg/kg to about 250 mg/kg.

In some embodiments, the checkpoint inhibitor, or a pharmaceutically acceptable salt thereof, is administered in an amount from about 1 mg/kg to about 15 mg/kg.

In some embodiments, the molar ratio of the inhibitor of de novo lipogenesis, or a pharmaceutically acceptable salt thereof, to the checkpoint inhibitor, or a pharmaceutically acceptable salt thereof, is from about 150:1 to about 1:3.

In some embodiments, the cancer is selected from the group consisting of: a kidney cancer, a liver cancer, a breast cancer, a lung cancer, a pancreatic cancer, a bladder cancer, a colon cancer, a melanoma, a thyroid cancer, an ovarian cancer, and a prostate cancer.

In some embodiments, the cancer is breast cancer.

In some embodiments, the breast cancer is HER2-positive breast cancer.

In some embodiments, the cancer is clear cell renal cell carcinoma (ccRCC).

In some embodiments, the cancer is a kidney cancer.

In some embodiments, the cancer is a bladder cancer.

In some embodiments, the bladder cancer is selected from the group consisting of: transitional cell carcinoma, urothelial carcinoma, papillary carcinoma, flat carcinoma, squamous cell carcinoma, adenocarcinoma, small-cell carcinoma, and sarcoma.

In some embodiments, the bladder cancer is a transitional cell carcinoma.

In some embodiments, the cancer is a thyroid cancer.

In some embodiments, the cancer is a liver cancer.

In some embodiments, the liver cancer is hepatobiliary carcinoma (HCC).

In some embodiments, the cancer is a lung cancer.

In some embodiments, the lung cancer is non-small cell lung cancer (NSCLC).

In some embodiments, the cancer is a solid tumor.

In a second general aspect, the present application provides a method of increasing the immunogenic susceptibility of a cell, the method comprising: i) selecting a poorly immunogenic cell; and ii) contacting the cell with an effective amount of an inhibitor of de novo lipogenesis, or a pharmaceutically acceptable salt thereof.

In some embodiments, the cell is a cancer cell.

In some embodiments, the cancer is selected from the group consisting of: a kidney cancer, a liver cancer, a breast cancer, a lung cancer, a pancreatic cancer, a bladder cancer, a colon cancer, a melanoma, a thyroid cancer, an ovarian cancer, and a prostate cancer.

In some embodiments, the cancer is breast cancer.

In some embodiments, the breast cancer is HER2-positive breast cancer.

In some embodiments, the cancer is clear cell renal cell carcinoma (ccRCC).

In some embodiments, the cancer is a kidney cancer.

In some embodiments, the cancer is a bladder cancer.

In some embodiments, the bladder cancer is selected from the group consisting of: transitional cell carcinoma, urothelial carcinoma, papillary carcinoma, flat carcinoma, squamous cell carcinoma, adenocarcinoma, small-cell carcinoma, and sarcoma.

In some embodiments, the bladder cancer is a transitional cell carcinoma.

In some embodiments, the cancer is a thyroid cancer.

In some embodiments, the cancer is a liver cancer.

In some embodiments, the liver cancer is hepatobiliary carcinoma (HCC).

In some embodiments, the cancer is a solid tumor.

In some embodiments, the contacting is in vitro.

In some embodiments, the contacting is in vivo.

In some embodiments, the cell becomes susceptible to cell lysis induced by an immune cell.

In some embodiments, the immune cell is a T lymphocyte.

In some embodiments, the T lymphocyte is CD4+ T-cell.

In some embodiments, the T lymphocyte is CD8+ T-cell.

In a third general aspect, the present application provides method of increasing the immunogenic susceptibility of a tumor in a subject, the method comprising: i) selecting a subject having a poorly immunogenic tumor; and ii) administering to the subject a therapeutically effective amount of an inhibitor of de novo lipogenesis, or a pharmaceutically acceptable salt thereof.

In some embodiments, the tumor is cancerous.

The method of claim 62, wherein the tumor is selected from the group consisting of: a kidney cancer, a liver cancer, a breast cancer, a lung cancer, a pancreatic cancer, a bladder cancer, a colon cancer, a melanoma, a thyroid cancer, an ovarian cancer, and a prostate cancer.

In some embodiments, the tumor is breast cancer.

In some embodiments, the breast cancer is HER2-positive breast cancer.

In some embodiments, the tumor is clear cell renal cell carcinoma (ccRCC).

In some embodiments, the tumor is a kidney cancer.

In some embodiments, the tumor is a bladder cancer.

In some embodiments, the bladder cancer is selected from the group consisting of: transitional cell carcinoma, urothelial carcinoma, papillary carcinoma, flat carcinoma, squamous cell carcinoma, adenocarcinoma, small-cell carcinoma, and sarcoma.

In some embodiments, the bladder cancer is a transitional cell carcinoma.

In some embodiments, the tumor is a thyroid cancer.

In some embodiments, the tumor is a liver cancer.

In some embodiments, the liver cancer is hepatobiliary carcinoma (HCC).

In some embodiments, the tumor is solid.

In some embodiments, the subject is a mammal.

In some embodiments, the subject is a human.

In some embodiments, the inhibitor of de novo lipogenesis is administered orally.

In some embodiments, the inhibitor of de novo lipogenesis is administered in an amount from about 200 mg/kg to about 250 mg/kg.

In some embodiments, the cells of the tumor become susceptible to cell lysis induced by an immune cell.

In some embodiments, the immune cell is a T lymphocyte.

In some embodiments, the T lymphocyte is CD4+ T-cell.

In some embodiments, the T lymphocyte is CD8+ T-cell.

In some embodiments, increasing the immunogenic susceptibility of the tumor sensitizes the tumor for immunotherapy or a checkpoint inhibitor therapy.

Implementations of the first, second, and third general aspects may include one or more of the following features.

In some embodiments, the inhibitor of de novo lipogenesis is the inhibitor of fatty-acid synthesis.

In some embodiments, the fatty acid is a Δ-9 monounsaturated fatty acid (MUFA).

In some embodiments, the MUFA is oleic acid (OA).

In some embodiments, the MUFA is palmitoleic acid (PA).

In some embodiments, the inhibitor of de novo lipogenesis is the inhibitor of stearoyl-CoA desaturase 1 (SCD1).

In some embodiments, the inhibitor of de novo lipogenesis is a compound of Formula (I):

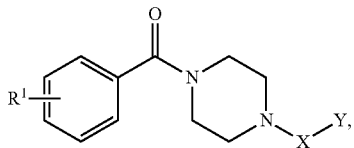
(I)

or a pharmaceutically acceptable salt thereof,
wherein:
$R^1$ is an unsubstituted $C_{1-6}$alkyl or $C_{1-6}$haloalkyl;
X is

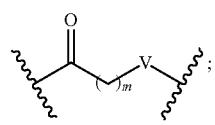

Y is selected from the group consisting of:

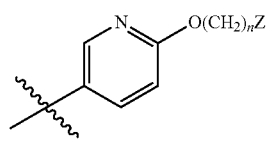 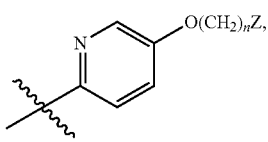

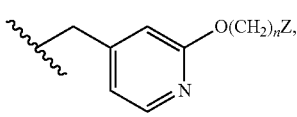

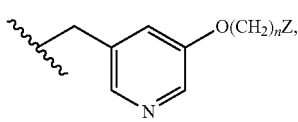

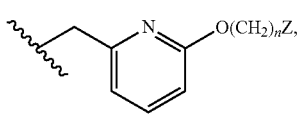

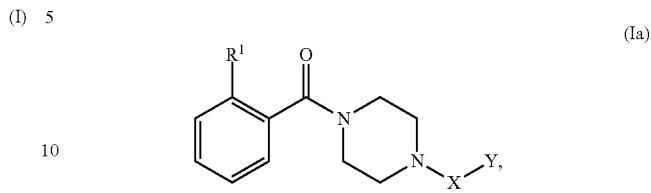

m is 0 or 1;
n is 0, 1, or 2;
V is $NR^4$ or O;
$R^2$, $R^3$, and $R^4$ are each independently H or an unsubstituted $C_{1-6}$alkyl; and
Z is an unsubstituted aryl.

In some embodiments, the compound according to Formula (I) has the structure of Formula (Ia):

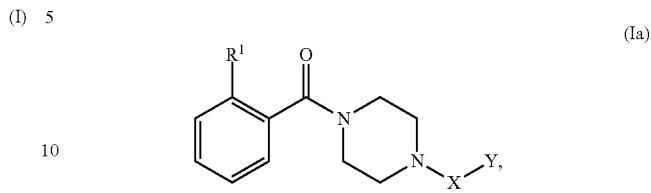
(Ia)

or a pharmaceutically acceptable salt thereof.
In some embodiments, $R^1$ is $CF_3$.
In some embodiments, m is 0.
In some embodiments, V is NH.
In some embodiments, Y is

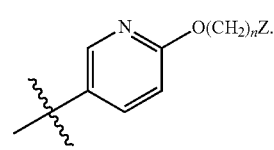

In some embodiments, Y is

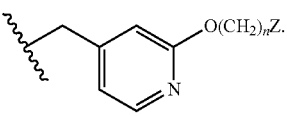

In some embodiments, m is 1.
In some embodiments, V is O.
In some embodiments, Y is

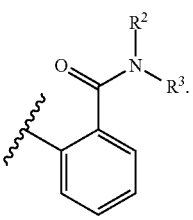

In some embodiments, $R^2$ is H; and $R^3$ is $CH_3$.
In some embodiments, Y is

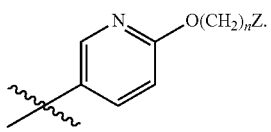

In some embodiments, n is 1.
In some embodiments, Z is phenyl.

In some embodiments, the compound according to Formula (I) is selected from the group consisting of:

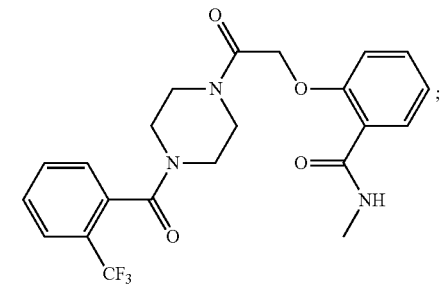

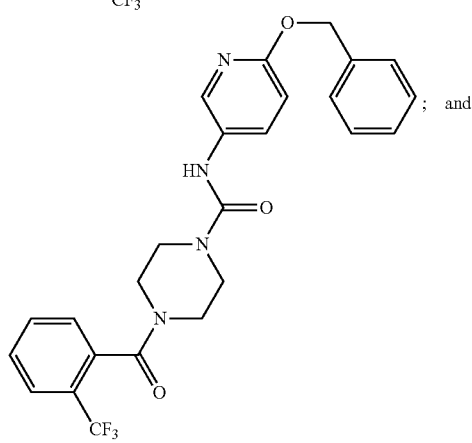

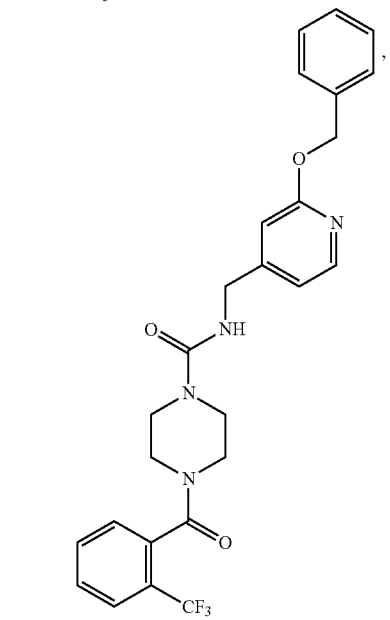

or a pharmaceutically acceptable salt thereof.

In some embodiments, the inhibitor of de novo lipogenesis is a compound of Formula (II):

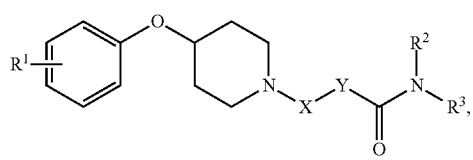

(II)

or a pharmaceutically acceptable salt thereof, wherein
R$^1$ is halo;
X is —(C=O)NR$^4$—;
Y is

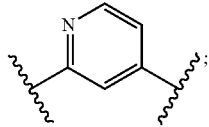 [SMILES: *c1ccnc(*)c1]

and
R$^2$, R$^3$, and R$^4$ are each independently H or an unsubstituted C$_{1-6}$alkyl.

In some embodiments, the compound according to Formula (II) has the structure of Formula (IIa):

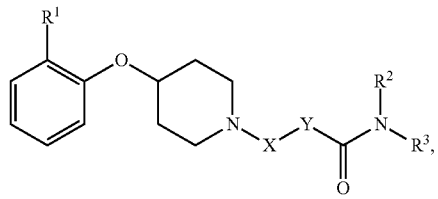

(IIa)

or a pharmaceutically acceptable salt thereof.
In some embodiments, R$^1$ is Cl.
In some embodiments, R$^4$ is H.
In some embodiments, R$^2$ is H; and R$^3$ is CH$_3$.
In some embodiments, the compound according to Formula (II) is

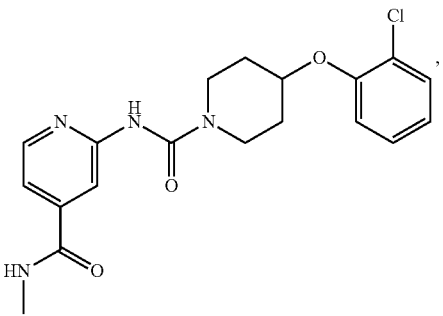 [SMILES: CNC(=O)c1ccnc(NC(=O)N2CCC(Oc3ccccc3Cl)CC2)c1 ; ","]

or a pharmaceutically acceptable salt thereof.

In some embodiments, the method of treating cancer in a subject comprises administering to the subject a therapeutically effective amount of:

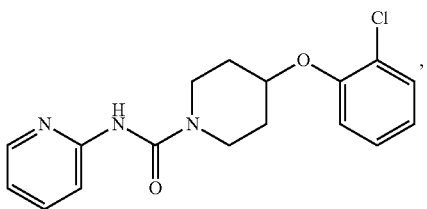

or a pharmaceutically acceptable salt thereof, and a therapeutically effective amount of a PD-1 inhibitor, or a pharmaceutically acceptable salt thereof.

In some embodiments, the PD-1 inhibitor is pembrolizumab or nivolumab.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DETAILED DESCRIPTION

Figure 1A:
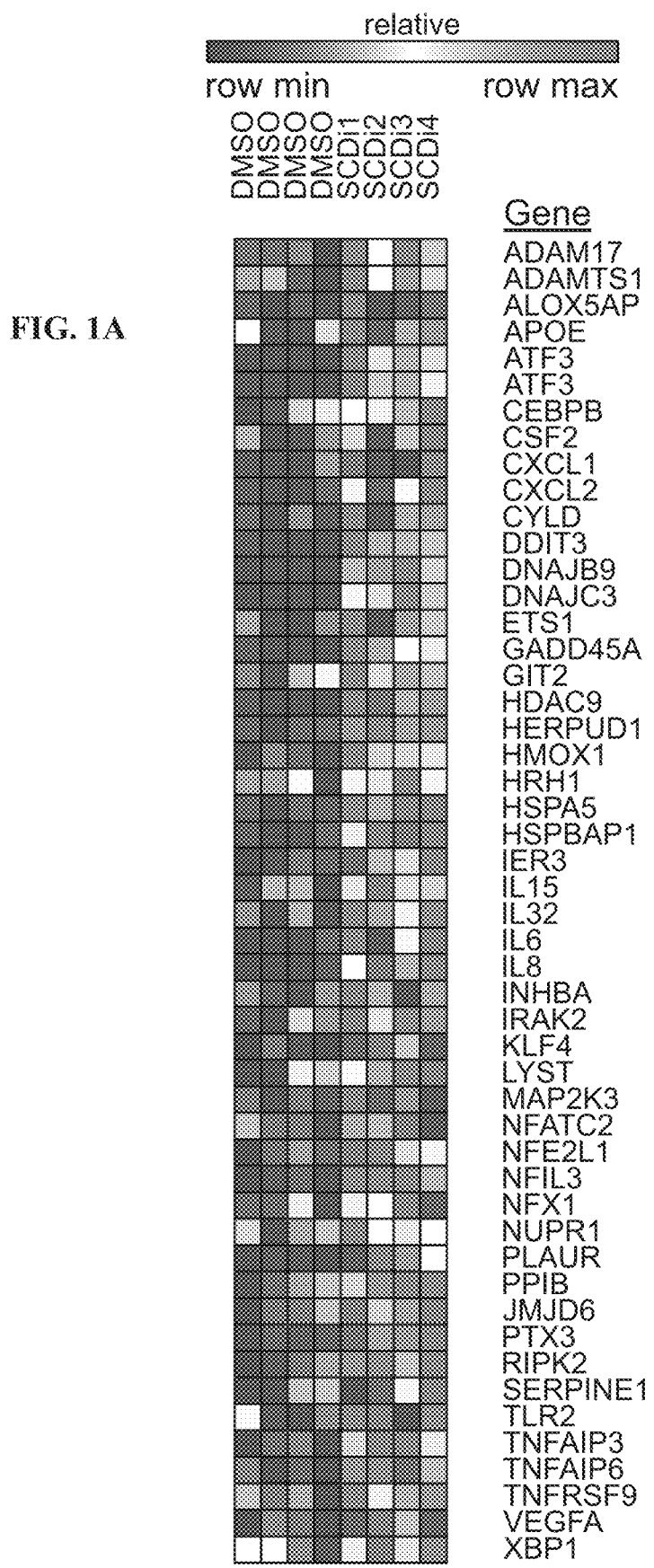
FIG. 1A shows gene array and ancillary pathway signature analysis of SCD1 inhibitor treated ccRCC cells.

Recent advances in cancer immunotherapy indicate that host resensitization to tumor presence can impart long-term survival benefits even in patients with end-stage disease (1,2). Positive results have been observed in patients treated with checkpoint inhibitors such as antibody mediated anti-PD-1 blockade. Efficacy of this class of drugs, however, is limited to tumors considered to be immunogenic, exhibiting evidence of spontaneous T cell priming and immune cell infiltration (3). For poorly immunogenic tumors, existing platforms such as adoptive cell transfer or tumor vaccination aimed to achieve host resensitization suffer from low potency and inability to generate long-term immune memory (4).

While de novo lipogenesis is a normal physiological process, most normal tissues rely on exogenous uptake of free fatty acids (FA) from the bloodstream (5) including those with high proliferative capacity such as hematopoietic cells and intestinal epithelia (6). Contrary to this, many aggressive cancers demonstrate increased fatty acid metabolism, establishing this phenomenon as a hallmark of oncogenesis (7,8). As such, targeting constituents of lipid biosynthesis has become a focus for developing new anti-cancer therapies. SCD1 is an enzyme that catalyzes the de novo lipogenesis of Δ-9 monounsaturated fatty acids (MUFA) oleic acid (OA) and palmitoleic acid (PA), influencing a number of cellular processes (9,10). Targeting SCD1 enzymatic activity induces apoptosis in a variety of aggressive tumor models including kidney, liver, breast, lung, thyroid, and colon cancers (11-16).

The present disclosure describes that inhibition of de novo lipogenesis using, e.g., SCD1 inhibitors, primes the tumor immune landscape towards a pro-inflammatory phenotype and enhances the therapeutic benefit of checkpoint inhibitors such as anti-PD-1 agents.

In one general aspect, the present application provides a method of increasing the immunogenic susceptibility of a cell. In some embodiments, a cell with increased immunogenic susceptibility is able to provoke a pro-inflammatory or immune response in vitro or in vivo, such that the cell is detected and neutralized by the immune system of the cell's host. In some embodiments, the neutralization comprises lysis of the cell, for example, by a cytolytic protein such as perforin, which is expressed by the immune cells of the immune system of the host. The immune system may be an innate or an adaptive immune system. Suitable examples of immune cells include natural killer (NK) cells, myeloid-derived suppressor cells (MDSC), red blood cells (RBC), thymocytes, megakaryocytes, innate lymphoid cells (ILC), granulocytes, B lymphocytes (B cells) and T lymphocytes (T cells). In some embodiments, the T-cell may be a natural killer T (NKT) cell, gamma delta T cell, regulatory T Cell (Treg), or helper T (Th) cell. In some embodiments, the T cell is a CD4+ T lymphocyte of a CD8+ T lymphocyte. In some embodiments, the immune cell comprises a checkpoint protein receptor, which suppresses the immune cell's inflammatory activity and protects the cells native to the host from autoimmunity. For example, when the checkpoint protein receptor binds to a checkpoint receptor ligand on the surface of the host's native cell (or a cancer cell), it can act as an "off-switch" that keeps the immune cell (e.g., T cell) from attacking the native cell (or a cancer cell). Some immune cells need a checkpoint protein to be activated to start an immune response, for example, when the checkpoint protein is dissociated from its ligand. In some embodiments, the checkpoint protein is a programmed cell death protein-1 (PD-1), cytotoxic T-lymphocyte-associated protein-4 (CTLA-4), or a T-cell immunoglobulin and mucin-domain containing-3 (TIM-3). In some embodiments, the checkpoint protein ligand is a programmed death-ligand-1 (PD-L1) or a programmed death-ligand-2 (PD-L2). In some embodiments, the checkpoint protein is LAG-3 (CD223) which is a cell surface molecule expressed on activated T cells (See, e.g., Huard et al. *Immunogenetics* 39:213-217, 1994; Goldberg et al. *Curr Top Microbiol Immunol.* 2011, 344, 269-78).

In some embodiments, the method of increasing immunogenic susceptibility of a cell comprises contacting the cell with an effective amount of an inhibitor of de novo lipogenesis, or a pharmaceutically acceptable salt thereof. The contacting may occur in vitro (e.g., in a culture medium), or in vivo (e.g., by administering the inhibitor of de novo lipogenesis to the host of the cell). In some embodiments, prior to contacting the cell with the inhibitor of the de novo lipogenesis, the method comprises selecting a poorly immunogenic cell (e.g., identifying a cell in need of increasing its immunogenic susceptibility). For example, the cell does not provoke a pro-inflammatory or immune response and may not be neutralized by an immune cell. In one example, a poorly immunogenic cell comprises checkpoint protein ligand (e.g., PD-L1) which binds with the checkpoint protein receptor on the surface of the immune cell and "turns off" the immune response. In some embodiments, contacting the cell with the inhibitor of the de novo lipogenesis induces endoplasmic reticulum (ER) stress, which may provoke an adaptive immune response through the emission of immunostimulatory signals, or damage-associated molecular patterns (DAMPs) such as heat shock proteins, or translocation of calreticulin (CRT) to the plasma membrane of the cell. In some embodiments, the ER stress leads to an increase in the immunogenicity of the cell.

In some embodiments, the cell is a cancer cell. Exemplary embodiments of cancer cells are described herein.

Inhibitors of De Novo Lipogenesis

In some embodiments, the inhibitor of de novo lipogenesis is an inhibitor of fatty-acid synthesis. In some embodiments, the inhibition of fatty acid synthesis subsequently inhibits the intracellular synthesis of triglycerides, sphingolipids, glycolipids, phospholipids, lipoproteins and/or other fatty-acid containing molecules that influence membrane fluidity, membrane raft formation and receptor clustering, second messenger signaling, fatty acid oxidation, energy storage, cell division, inflammation, and a number of other biological functions. In some embodiments, the inhibitor of de novo lipogenesis inhibits the synthesis of unsaturated fatty acids. In some aspects of these embodiments, the inhibitor of de novo lipogenesis inhibits the synthesis of monounsaturated fatty acids, such as a Δ-9 monounsaturated fatty acid (MUFA). In some embodiments, the inhibitor of de novo lipogenesis inhibits the synthesis of oleic acid (OA) and/or palmitoleic acid (PA). In some embodiments, the inhibitor of de novo lipogenesis is an inhibitor of stearoyl-CoA desaturase 1 (SCD1).

In some embodiments, the inhibitor of stearoyl-CoA desaturase 1 (SCD1) is a compound according to Formula (I):

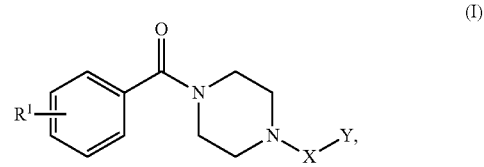

or a pharmaceutically acceptable salt thereof, wherein:
R¹ is an unsubstituted $C_{1-6}$alkyl or $C_{1-6}$haloalkyl;
X is

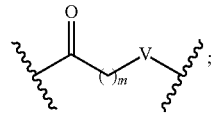

Y is selected from:

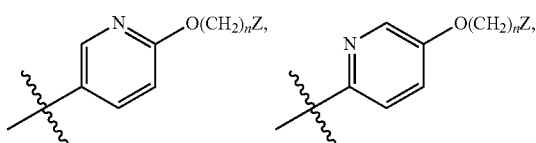

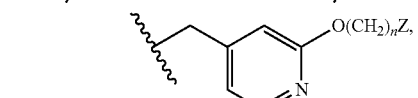

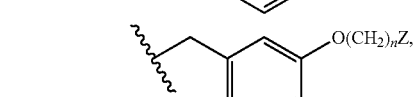

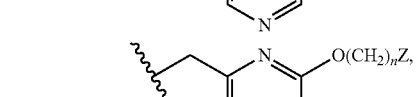

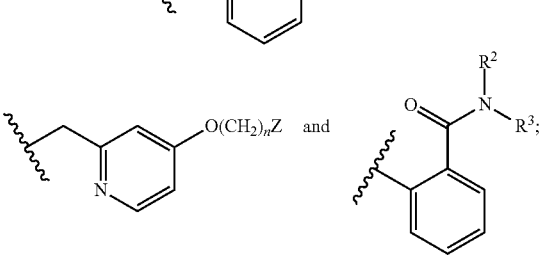

m is 0 or 1;
n is 0, 1, or 2;
V is $NR^4$ or O;
$R^2$, $R^3$, and $R^4$ are each independently H or an unsubstituted $C_{1-6}$alkyl; and
Z is an unsubstituted aryl.

In some embodiments, the compound according to Formula (I) has the structure of Formula (Ia):

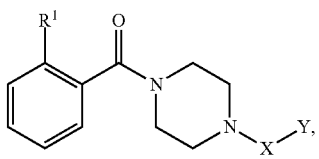
(Ia)

or a pharmaceutically acceptable salt thereof.

In some embodiments, V is $NR^4$. In some embodiments, V is NH. In some embodiments, V is O.

In some embodiments, X is

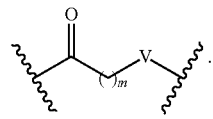

In some embodiments, Y is

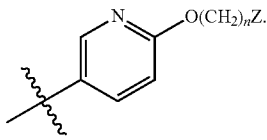

In some embodiments, Y is

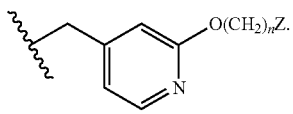

In some embodiments, Y is

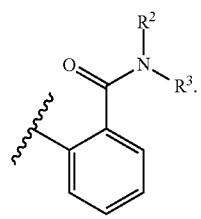

In some embodiments, Z is selected from the group consisting of: phenyl and naphthyl. For example, Z can be phenyl.

In some embodiments, m is 0. In some embodiments, m is 1.

In some embodiments, n is 0. In some embodiments, n is 1. In some embodiments, n is 2.

In some embodiments, $R^1$ is an unsubstituted $C_{1-6}$alkyl. In some embodiments, $R^1$ is an unsubstituted $C_{1-3}$alkyl. For example, $R^1$ can be $CH_3$. In some embodiments, $R^1$ is a $C_{1-6}$haloalkyl. In some embodiments, $R^1$ is a $C_{1-3}$haloalkyl. For example, $R^1$ can be $CF_3$.

In some embodiments, $R^2$ is an unsubstituted $C_{1-6}$alkyl. For example $R^2$ can be $CH_3$. In some embodiments, $R^2$ is H.

In some embodiments, $R^3$ is an unsubstituted $C_{1-6}$alkyl. For example $R^3$ can be $CH_3$. In some embodiments, $R^3$ is H.

In some embodiments, $R^4$ is an unsubstituted $C_{1-6}$alkyl. For example $R^4$ can be $CH_3$. In some embodiments, $R^4$ is H.

In some embodiments, $R^2$ is H; and $R^3$ is $CH_3$.

Non-limiting examples of a compound according to Formula (I) and/or Formula (Ia) include:

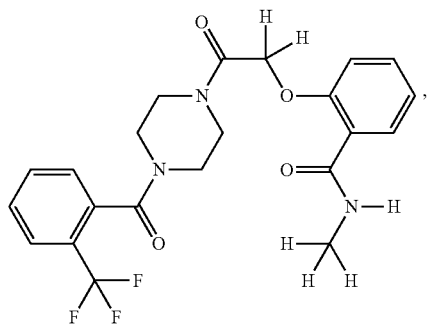
SSI-1

N-Methyl-2-(2-oxo-2-{4-[2-(trifluoromethyl)benzoyl]piperazin-1-yl}ethoxy)benzamide;

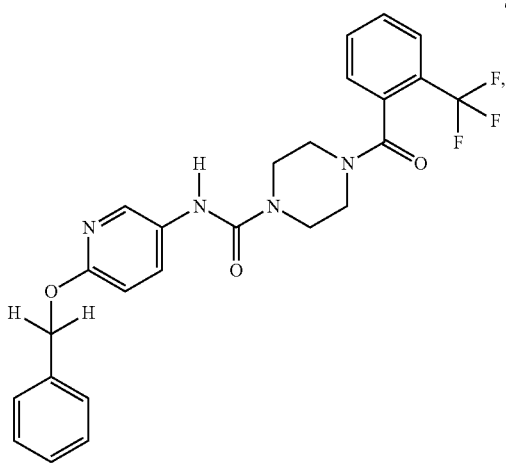

2-(benzyloxy)-5-{[hydroxy({4-[2-(trifluoromethyl)benzoyl]piperazin-1-yl})methyl]amino}-1,2-dihydropyridin-2-ylium-1-ide; and

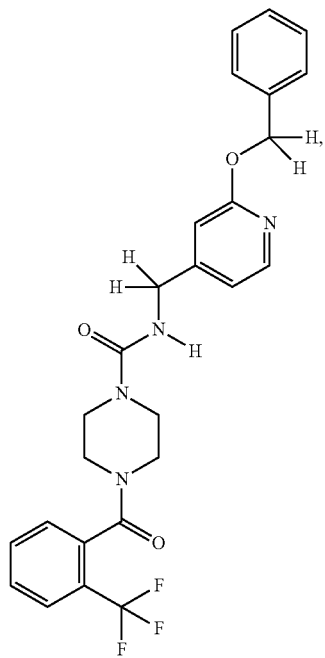

2-(benzyloxy)-4-({[hydroxy({4-[2-(trifluoromethyl)benzoyl]piperazin-1-yl})methyl]azanidyl}methyl)-1,2-dihydropyridin-2-ylium-1-ide, or a pharmaceutically acceptable salt thereof.

In some embodiments, the inhibitor of stearoyl-CoA desaturase 1 (SCD1) is a compound according to Formula (II):

(II)

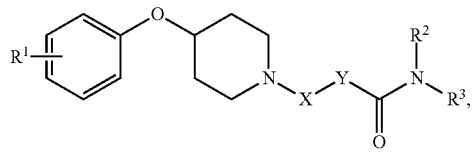

or pharmaceutically acceptable salt thereof, wherein
$R^1$ is halo;
X is —(C=O)NR$^4$—;
Y is

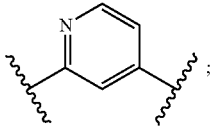 [SMILES: *c1ccnc(*)c1]

$R^2$, $R^3$, and $R^4$ are each independently H or an unsubstituted $C_{1-6}$alkyl.

In some embodiments, a compound according to Formula (II) has the structure of Formula (IIa):

(IIa)

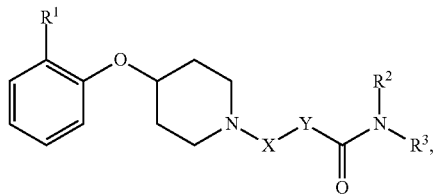

or pharmaceutically acceptable salt thereof.
In some embodiments, X is —(C=O)NR$^4$—.
In some embodiments, Y is

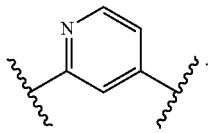 [SMILES: *c1ccnc(*)c1]

In some embodiments, $R^1$ is Cl. In some embodiments, $R^1$ is F.

In some embodiments, $R^2$ is an unsubstituted $C_{1-6}$alkyl. For example $R^2$ can be CH$_3$. In some embodiments, $R^2$ is H.

In some embodiments, $R^3$ is an unsubstituted $C_{1-6}$alkyl. For example $R^3$ can be CH$_3$. In some embodiments, $R^3$ is H.

In some embodiments, $R^4$ is an unsubstituted $C_{1-6}$alkyl. For example $R^4$ can be CH$_3$. In some embodiments, $R^4$ is H.

In some embodiments, $R^2$ is H; and $R^3$ is CH$_3$.

Non-limiting examples of a compound according to Formula (II) and/or Formula (IIa) include:

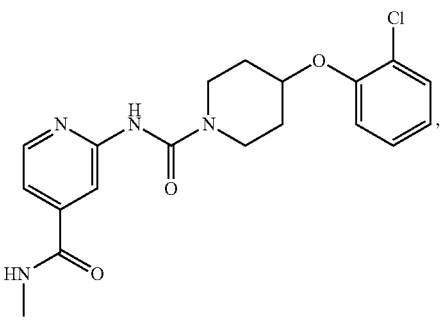

2-{[4-(2-Chlorophenoxy)piperidine-1-carbonyl]amino}-N-methylpyridine-4-carboxamide,
or pharmaceutically acceptable salt thereof.

In some embodiments, the inhibitor of stearoyl-CoA desaturase 1 (SCD1) is:

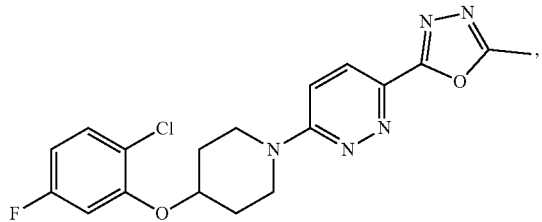 [SMILES: Cc1nnc(-c2ccc(N3CCC(Oc4cc(F)ccc4Cl)CC3)nn2)o1]

or pharmaceutically acceptable salt thereof.

In some embodiments, the inhibitor of stearoyl-CoA desaturase 1 (SCD1) is any one of the compounds described for example, in PCT application publication No. WO 2016/141299, US publication No. 2013/0096181, or U.S. Pat. No. 9,233,102, all of which are incorporated herein by reference in their entirety.

In some embodiments, the inhibitor of de novo lipogenesis is a fatty acid synthase (FASN) inhibitor (e.g., TVB-2640, fasnall, C 75, G 28UCM, GSK 2194069, Orlistat). The FASN inhibitor may inhibit the thioesterase domain of fatty acid synthase. In some embodiments, the inhibitor of de novo lipogenesis is carboxylester lipase inhibitor. In some embodiments, the inhibitor of de novo lipogenesis is inhibitor of pyruvate dehydrogenase (PDH). In some embodiments, the inhibitor of de novo lipogenesis is inhibitor of acetyl-CoA carboxylase. In some embodiments, the inhibitor of de novo lipogenesis is inhibitor of ATP-citrate lyase.

In another general aspect, the present application provides a method of increasing the immunogenic susceptibility of a tumor in a subject. In some embodiments, the method comprises administering to the subject a therapeutically effective amount of an inhibitor of de novo lipogenesis, or a pharmaceutically acceptable salt thereof (e.g., any one of inhibitors of de novo lipogenesis described herein). In some embodiments, the method comprises selecting a subject having a poorly immunogenic tumor.

In some embodiments, administration of the inhibitor of de novo lipogenesis to the subject results in increased recruitment of a pro-inflammatory antigen presenting cell (APC) into the tumor microenvironment. Suitable examples of APCs are macrophages (MP) and/or dendritic cells (DC). In some embodiments, administration of the inhibitor of de novo lipogenesis to the subject increases the number of intra-tumor DCs. In some embodiments, administration of the inhibitor of de novo lipogenesis to the subject results in an increase in the number of tumor-associated leukocytes in the subject of at least about 5%, about 10%, about 15%, about 20%, or about 25%. In some embodiments, antigen presenting cell activation augments infiltration and activation of the immune cells, such as T lymphocytes. In some embodiments, administration of the inhibitor of de novo lipogenesis to the subject results in production of cytolytic proteins such as perforin. For example, cytolytic proteins are produced by the immune cells responsible for tumor cell lysis during immunogenic cell death. In some embodiments, the immune cell is any one of the immune cells described herein, such as T lymphocytes (e.g., CD4+ or CD8+ T cells). In some embodiments, administration of the inhibitor of de novo lipogenesis to the subject sensitizes the tumor for an immunotherapy or a checkpoint inhibitor therapy.

In another general aspect, the present application provides a method of treating cancer (e.g., any one of cancers described herein) in a subject, the method comprising administering to the subject a therapeutically effective amount of an inhibitor of de novo lipogenesis (e.g., any one of the inhibitors described herein), or a pharmaceutically acceptable salt thereof, and a therapeutically effective amount of a checkpoint inhibitor (e.g., any one of checkpoint inhibitors described herein), or a pharmaceutically acceptable salt thereof. In some embodiments, the subject is in need of the treatment (e.g., the subject is diagnosed with, or identified as having, a cancer). In some embodiments, the method comprises selecting the subject for the combination treatment, for example, by determining that the cancer is poorly immunogenic, using any of the methods and/or kits known in the art for analysis of tumor immunogenic susceptibility.

In some embodiments, the cancer is characterized in that the cancer cells express a cell-surface checkpoint protein ligand (e.g., PD-L1). The ligand may bind with the checkpoint protein receptor (e.g., PD-1) on the surface of an immune cell. In some embodiments, this binding leads to inactivation of the immune cell, and the cancer cell remains intact (e.g., the cancer cell grows and proliferates despite attack by the immune cell). In some embodiments, administration of an inhibitor of de novo lipogenesis to the subject induces and/or upregulates expression of the checkpoint protein ligands in the cancer cells of the subject. In other embodiments, administration of an inhibitor of de novo lipogenesis to the subject does not change the levels of expression of the checkpoint protein ligands in the cancer cells of the subject.

In some embodiments, a checkpoint inhibitor blocks the binding between the checkpoint protein receptor of an immune cell and the checkpoint protein ligand of the cancer cell, thus activating the immune cell ("turning on the switch"). In some embodiments, administering a checkpoint inhibitor results in immunogenic death of the cancer cells.

In some embodiments, the cancer is associated with overexpression of an SCD1 protein, a SCD1 enzyme (e.g., "a SCD1-associated cancer") (see, e.g., von Roemeling, C. A. et al. *J. Clin. Endocrinol. Metab.* (May 2015) 100(5): E697-E709). The term "SCD1-associated cancer" as used herein refers to cancers associated with or having a dysregulation of a SCD1 protein (SCD1 enzyme), or expression or activity or level of the same.

In some embodiment, the method comprises administering one or more (e.g., one, two, three, four, or more) of the inhibitors of de novo lipogenesis; and administering one or more (e.g., one, two, three, four, or more) of the checkpoint inhibitors. In some embodiments, the inhibitor of de novo lipogenesis is administered with at least two checkpoint inhibitors. In some embodiments, the inhibitor of de novo lipogenesis is administered with at least three checkpoint inhibitors.

In some embodiments, the inhibitor of de novo lipogenesis and the checkpoint inhibitor are admixed prior to administration (e.g., the inhibitor of de novo lipogenesis and the checkpoint inhibitor are administered in a pharmaceutical composition) as described herein. In some embodiments, the inhibitor of de novo lipogenesis and the checkpoint inhibitor are administered concurrently. For example, the inhibitor of de novo lipogenesis is administered orally (e.g., in a tablet or capsule); and the checkpoint inhibitor is simultaneously administered intravenously. In some embodiments, the inhibitor of de novo lipogenesis and the checkpoint inhibitor are administered sequentially, e.g., one of the therapeutic agents is administered prior to administration of the other therapeutic agent. For example, the inhibitor of de novo lipogenesis may be administered orally (e.g., in a tablet or capsule) for a period of time (e.g. 1-10 days) prior to intravenous administration of the checkpoint inhibitor (e.g., one every three months). In some embodiments, a method of treating cancer in a subject comprises administering to the subject SSI-4, or a pharmaceutically acceptable salt thereof, and an anti-PD-1 antibody, or a pharmaceutically acceptable salt thereof Checkpoint Inhibitors In some embodiments, the checkpoint inhibitor is a small-molecule drug. Small molecule drugs are low molecular weight organic compounds (typically about 2000 daltons or less). In some embodiments, the molecular weight of the drug molecule is in the range from about 200 to about 2000, from about 200 to about 1800, from about 200 to about 1600, from about 200 to about 1400, from about 200 to about 1200, from about 200 to about 1000, from about 200 to about 800, from about 200 to about 600 daltons, from about 300 to about 2000, from about 300 to about 1800, from about 300 to about 1600, from about 300 to about 1400, from about 300 to about 1200, from about 300 to about 1000, from about 300 to about 800, and/or from about 300 to about 600 daltons.

In some embodiments, the checkpoint inhibitor is a therapeutic protein or a peptide, such as an antibody, a hormone, a transmembrane protein, a growth factor, an enzyme, or a structural protein. In some embodiments, the checkpoint inhibitor is a biomolecule having a molecular weight of 200 daltons or more produced by living organisms or cells, including large polymeric molecules such as polypeptides, proteins, glycoproteins, polysaccharides, polynucleotides and nucleic acids, or analogs or derivatives of such molecules.

In some embodiments, the checkpoint inhibitor is an antibody, such as a monoclonal or a polyclonal antibody.

In some embodiments, the checkpoint inhibitor is selected form the group consisting of: a programmed cell death protein-1 (PD-1) inhibitor, an inhibitor of programmed death-ligand-1 (PD-L1) or programmed death-ligand-2 (PD-L2), an inhibitor of cytotoxic T-lymphocyte-associated protein-4 (CTLA-4), an inhibitor of Lymphocyte-activation gene 3 (LAG-3), an inhibitor of luster of Differentiation 47 (CD47), an inhibitor of Signal regulatory protein α (SIRP α) (e.g., TTI-621, OSE-172), and an inhibitor of T-cell immunoglobulin and mucin-domain containing-3 (TIM-3). In some embodiments, the checkpoint inhibitor is a dual inhibitor of LAG-3 and PD-1 (e.g., MGD013). In some embodiments, the checkpoint inhibitor is selected form the group consisting of: an anti-PD-1 antibody (e.g., pembrolizumab, nivolumab), an anti-PD-L1 antibody (e.g., atezolizumab), an anti-PD-L2 antibody, an anti-CTLA-4 antibody (e.g., ipilimumab), and an anti-TIM-3 antibody (e.g., TSR-022). In some embodiments, the checkpoint inhibitor is selected form the group consisting of: PD-1 inhibitor, PD-L1 inhibitor, PD-L2 inhibitor, TIM-1 inhibitor, TIM-3 inhibitor, LAG-3 inhibitor, CTLA-4 inhibitor, CD-47 inhibitor, SIRPα inhibitor, and VISTA inhibitor. In some embodiments, the checkpoint inhibitor is selected form the group consisting of: pembrolizumab, nivolumab, atezolizumab, ipilimumab, and TSR-022. In some embodiments, the checkpoint inhibitor is selected form the group consisting of: pembrolizumab, nivolumab, atezolizumab, ipilimumab, TSR-022, MGD013, TTI-621, OSE-172 and CA-170. In some embodiments, the method comprises administering to the subject at least two of: pembrolizumab, nivolumab, atezolizumab, ipilimumab, and TSR-022. In some embodiments, the method comprises administering to the subject at least two of: pembrolizumab, nivolumab, atezolizumab, ipilimumab, TSR-022, TTI-621, OSE-172 and CA-170. In some embodiments, the method comprises administering to the subject at least three of: pembrolizumab, nivolumab, atezolizumab, ipilimumab, and TSR-022. In some embodiments, the method comprises administering to the subject at least three of: pembrolizumab, nivolumab, atezolizumab, ipilimumab, TSR-022, MGD013, TTI-621, OSE-172 and CA-170. In some embodiments, the method comprises administering to the subject pembrolizumab and nivolumab. In some embodiments, the method comprises administering to the subject pembrolizumab, nivolumab, atezolizumab, and ipilimumab. In some embodiments, the method comprises administering to the subject pembrolizumab, nivolumab, atezolizumab, ipilimumab, and TSR-022. In some embodiments, the method comprises administering to the subject pembrolizumab, nivolumab, atezolizumab, ipilimumab, TSR-022, MGD-013, TTI-621, OSE-172 and CA-170. In some embodiments, the checkpoint inhibitor is an antibody and is administered to the subject intravenously. In some embodiments, the checkpoint inhibitor is an antibody and is administered to the subject orally. In some embodiments, the checkpoint inhibitor is a small-molecule drug that is administered to the subject orally (e.g., CA-170). In some embodiments, when at least two checkpoint inhibitors are administered to the subject, at least one checkpoint inhibitor is administered orally, and at least one checkpoint inhibitor is administered intravenously. In some embodiments, all checkpoint inhibitors are administered intravenously.

In some embodiments, the checkpoint inhibitor is any one of checkpoint inhibitors described in Petrova et al., TTI-621 (SIRPαFc): A CD47-Blocking Innate Immune Checkpoint Inhibitor with Broad Anti-Tumor Activity and Minimal Erythrocyte Binding, Clinical Cancer Research, 2016 (DOI: 10.1158/1078-0432.CCR-16-1700). In some embodiments, the checkpoint inhibitor is inhibitor of CD47 (receptor) or SIRPalpha (ligand). In some embodiments, the checkpoint inhibitor is TTI-621, that binds to and neutralizes CD47, produced by Trillium Therapeutics Inc; or OSE-172, antagonist of SIRPα, produced by OSE Immunotherapeutics. In some embodiments, the checkpoint inhibitor is an inhibitor of LAG-3 (CD223) (e.g., MGD013, a dual inhibitor of LAG-3 and PD-1, manufactured by MacroGenics). In some embodiments, the checkpoint inhibitor is V-domain Immunoglobulin Suppressor of T-cell Activation (VISTA) antagonist (e.g., CA-170 manufactured by Curtis Inc). In some embodiments, the checkpoint inhibitor selectively targets and inhibit both PD-L1 and VISTA (e.g., CA-170). In some embodiments, the checkpoint inhibitor is PD-L1/VISTA antagonist.

In some embodiments, an inhibitor of de novo lipogenesis (e.g., SCD1 inhibitor such as SSI-4) modulates tumor immunity and is administered with an anti-PD-1 antibody and an anti-LAG3 antibody. In some embodiments, an inhibitor of de novo lipogenesis (e.g., SSI-4) modulates tumor immunity and synergizes with a checkpoint inhibitor (e.g., anti-PD-1 antibody).

Cancer Cells

In some embodiments, the cancer is selected from the group consisting of: a kidney cancer, a liver cancer, a breast cancer, a lung cancer, a pancreatic cancer, a bladder cancer, a colon cancer, a melanoma, a thyroid cancer, an ovarian cancer, and a prostate cancer. The cancer may be, for example, any one of the following cancers:

breast cancers, including, for example ER+ breast cancer, ER− breast cancer, her2− breast cancer, her2+ breast cancer, stromal tumors such as fibroadenomas, phyllodes tumors, and sarcomas, and epithelial tumors such as large duct papillomas; carcinomas of the breast including in situ (non-invasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative (ER–), progesterone receptor negative, and her2 negative (her2–). In some embodiments, the breast cancer may have a high risk Oncotype score;

hematopoietic cancers, including, for example, leukemia (acute lymphocytic leukemia (ALL), acute lyelogenous leukemia (AML), chronic lymphocytic leukemia (CLL), chronic myelogenous leukemia (CML), hairy cell leukemia), mature B cell neoplasms (small lymphocytic lymphoma, B cell prolymphocytic leukemia, lymphoplasmacytic lymphoma (such as Waldenström's macroglobulinemia), splenic marginal zone lymphoma, plasma cell myeloma, plasmacytoma, monoclonal immunoglobulin deposition diseases, heavy chain diseases, extranodal marginal zone B cell lymphoma (MALT lymphoma), nodal marginal zone B cell lymphoma (NMZL), follicular lymphoma, mantle cell lymphoma, diffuse B cell lymphoma, diffuse large B cell lymphoma (DLBCL), mediastinal (thymic) large B cell lymphoma, intravascular large B cell lymphoma, primary effusion lymphoma and Burkitt lymphoma/leukemia), mature T cell and natural killer (NK) cell neoplasms (T cell prolymphocytic leukemia, T cell large granular lymphocytic leukemia, aggressive NK cell leukemia, adult T cell leukemia/lymphoma, extranodal NK/T cell lymphoma, enteropathy-type T cell lymphoma, hepatosplenic T cell lymphoma, blastic NK cell lymphoma, mycosis fungoides (Sezary syndrome), primary cutaneous anaplastic large cell lymphoma, lymphomatoid papulosis, angioimmunoblastic T cell lymphoma, unspecified peripheral T cell lymphoma and anaplastic large cell lymphoma), Hodgkin lymphoma (nodular sclerosis, mixed celluarity, lymphocyte-rich, lymphocyte depleted or not depleted, nodular lymphocyte-predominant), myeloma (multiple myeloma, indolent myeloma, smoldering myeloma), chronic myeloproliferative disease, myelodysplastic/myeloproliferative disease, myelodysplastic syndromes, immunodeficiency-associated lymphoproliferative disorders, histiocytic and dendritic cell neoplasms, mastocytosis, chondrosarcoma, Ewing sarcoma, fibrosarcoma, malignant giant cell tumor, and myeloma bone disease;

lung cancers, including, for example, bronchogenic carcinoma, e.g., squamous cell, undifferentiated small cell, non-small cell lung cancer (NSCLC), undifferentiated large cell, and adenocarcinoma; alveolar and bronchiolar carcinoma; bronchial adenoma; sarcoma; lymphoma; chondromatous hamartoma; and mesothelioma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; hepatobiliary carcinoma (HCC), and hemangioma;

kidney (renal) cancers, including, for example, clear cell renal cell carcinoma (ccRCC), papillary renal cell carcinoma, chromophobe renal cell carcinoma, collecting duct renal cell carcinoma, unclassified renal cell carcinoma, transitional cell carcinoma, and renal sarcoma;

bladder cancers, including, for example, transitional cell carcinoma, urothelial carcinoma, papillary carcinoma, flat carcinoma, squamous cell carcinoma, adenocarcinoma, small-cell carcinoma, and sarcoma;

gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, epithelial cancer, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis;

thyroid cancers, including, for example, papillary thyroid cancer, follicular thyroid cancer, anaplastic thyroid carcinoma, and medullary thyroid cancer; and adrenal gland cancers, including, for example, neuroblastoma.

In some embodiments, the cancer is a solid tumor.

Additional Anticancer Agents

In some embodiments, the method of treating cancer in a subject further comprises administering to the subject at least one additional therapeutic agent. In some embodiments, the additional therapeutic agent is a pain relief agent (e.g., a nonsteroidal anti-inflammatory drug such as celecoxib or rofecoxib), an antinausea agent, or an additional anticancer agent (e.g., paclitaxel, docetaxel, doxorubicin, daunorubicin, epirubicin, fluorouracil, melphalan, cis-platin, carboplatin, cyclophosphamide, mitomycin, methotrexate, mitoxantrone, vinblastine, vincristine, ifosfamide, teniposide, etoposide, bleomycin, leucovorin, taxol, herceptin, avastin, cytarabine, dactinomycin, interferon alpha, streptozocin, prednisolone, irinotecan, sulindac, 5-fluorouracil, capecitabine, oxaliplatin/5 FU, abiraterone, letrozole, 5-aza/romidepsin, or procarbazine). In certain embodiments, the anticancer agent is paclitaxel or docetaxel. In other embodiments, the anticancer agent is cisplatin or irinotecan. In some embodiments, the method of treating cancer in a subject further comprises administering to the subject a cell carcinoma treatment. Examples of additional optional renal cell carcinoma treatments include, without limitation, treatment with Nexavar®, Sutent®, Torisel®, Afinitor® (everolimus), axitinib, pazopanib, levatinib, interleukin-2, and combinations thereof. In some embodiments, the method of treating cancer in a subject further comprises administering to the subject a proteasome inhibitor. Exemplary proteasome inhibitors include lactacystin, bortezomib, dislfiram, salinosporamide A, carfilzomib, ONX0912, CEP-18770, MLN9708, epoxomicin, and MG132). Non-limiting examples of proteasome inhibitors include marizomib (NPI- 0052), bortezomib (Velcade®), and carfilzomib (Kyprolis®). Other suitable proteasome inhibitors can be found in U.S. Pat. Nos. 8,431,571; 8,357,683; 8,088,741; 8,080,576; 8,080,545; 7,691,852; 7,687,456; 7,531,526; 7,109,323; 6,699,835; 6,548,668; 6,297,217; 6,066,730, and published PCT applications WO 2011/123502; WO 2010/036357; WO 2009/154737; WO 2009/051581; WO 2009/020448, each of which is incorporated by reference in its entirety. In some embodiments, the combination of a compound provided herein (e.g., SSI-4) and a proteasome inhibitor have a synergistic effect on the treatment of the cancer. In some embodiments, the method of treating cancer in a subject further comprises administering to the subject one or more multikinase inhibitors (e.g., tyrosine kinase inhibitors, RAF kinase inhibitors, serine/threonine kinase inhibitors). In some embodiments, the multikinase inhibitor is sorafenib. In some embodiments, the combination of a compound provided herein (e.g., SSI-4) and sorafenib have a synergistic effect on the treatment of the cancer. In some embodiments, the method of treating cancer in a subject further comprises administering to the subject an inhibitor of mammalian target of rapamycin (mTor). Non-limiting examples of mTor inhibitors include: sirolimus (RAPAMUNE®), temsirolimus (CCI-779), everolimus (RAD001), ridaforolimus (AP-23573). In some embodiments, the method of treating cancer in a subject further comprises administering to the subject pacliltaxel and/or platin (cisplatin, carboplatin, or oxaliplatin) for the treatment of ovarian cancer.

In some embodiments, the following standard of care drugs can be combined with an inhibitor of de novo lipogenesis and a checkpoint inhibitor for the following cancers: Lung—paclitaxel, nivolumab, ceritinib, afatinib; Colon—capecitabine; Breast; Metastatic breast—capecitabine, paclitaxel, and/or gemcitabine; Hormonally responsive breast—aromatase inhibitors such as letrazole and/or antiestrogens such as tamoxifen; HER2 positive—Her2 inhibitors such as trastuzumab; palbociclib, ado-trastuzumab emtansine; Melanoma—temozolomide, and/or BRAF inhibitors, pembrolizumab, nivolumab, pomalidomide, dabrafenib; Prostate—androgen receptor inhibitors such as abiraterone; Bladder—gemcitabine and/or paclitaxel; Thyroid—paclitaxel, cisplatin, a proteasome inhibitor, sorafenib, lenvatinib; Pancreatic—gemcitabine; Liver—sorafenib; Mantle cell lymphoma—bortezomib; Multiple myeloma—panobinostat; Relapsed and/or refractory—carfilzomib, bortezomib and/or an immunomodulatory agent such as dexamethasone.

Pharmaceutically Acceptable Salts

In some embodiments, the present application provides a pharmaceutically acceptable salt of any one of the compounds disclosed herein (e.g., an inhibitor of de novo lipogenesis compound, a checkpoint inhibitor compound, or an additional therapeutic agent). In some embodiments, a salt of any one of the compounds disclosed herein is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds disclosed herein include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds disclosed herein include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

Compositions, Formulations, Dosages, Routes of Administration

In some embodiments, the present application provides pharmaceutical compositions comprising an inhibitor of de novo lipogenesis, or a pharmaceutically acceptable salt thereof; and a pharmaceutically acceptable carrier.

In some embodiments, the present application provides pharmaceutical compositions comprising a checkpoint inhibitor, or a pharmaceutically acceptable salt thereof; and a pharmaceutically acceptable carrier.

In some embodiments, the present application provides pharmaceutical compositions comprising an inhibitor of de novo lipogenesis, or a pharmaceutically acceptable salt thereof; a checkpoint inhibitor, or a pharmaceutically acceptable salt thereof, and a pharmaceutically acceptable carrier.

The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

If required, the solubility and bioavailability of the compounds of the present application in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of the present application optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502, all of which are hereby incorporated by reference in their entireties.

The pharmaceutical compositions of the present application include those suitable for oral, rectal, nasal, topical (including buccal and sublingual), vaginal, parenteral, or intraperitoneal (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Solutions or suspensions used for parenteral, intravenous, intradermal, intraocular or subcutaneous application can include the following components: a sterile diluent such as water for injection, saline solution (e.g., 0.9% saline solution), dextrose solution (e.g., 5%) dextrose solution), fixed oils, polyethylene glycols (e.g., PEG400), glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, an inhibitor of de novo lipogenesis is administered orally. Compositions of the present application suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets. In some embodiments, a checkpoint inhibitor is administered intravenously (e.g., by injection or infusion).

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of the present application may be administered in the form of suppositories for rectal administration. These compositions can be prepared by mixing a compound with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031.

Topical administration of the pharmaceutical compositions of the present application is especially useful when the desired treatment involves areas or organs readily accessible by topical application.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

In the pharmaceutical compositions of the present application, an inhibitor of de novo lipogenesis or a checkpoint inhibitor is present in an effective amount (e.g., a therapeutically effective amount).

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

In some embodiments, a therapeutically effective amount of an inhibitor of de novo lipogenesis is from about 10 to about 1000 mg/m$^2$, from about 20 to about 900 mg/m$^2$, from about 30 to about 800 mg/m$^2$, from about 40 to about 700 mg/m$^2$, from about 50 to about 800 mg/m$^2$, from about 50 to about 150 mg/m$^2$, from about 60 to about 600 mg/m$^2$, from about 70 to about 500 mg/m$^2$, or from about 100 to about 500 mg/m$^2$. 50-150 mg/m$^2$ In some embodiments, a therapeutically effective amount of an inhibitor of de novo lipogenesis is from about 5 to about 300 mg/kg, from about 10 mg/kg to about 250 mg/kg, from about 10 mg/kg to about 200 mg/kg, or from about 20 mg/kg to about 150 mg/kg. In some embodiments, a therapeutically effective amount of an inhibitor of de novo lipogenesis is from about 50 mg/kg to about 500 mg/kg, from about 50 mg/kg to about 400 mg/kg, from about 50 mg/kg to about 300 mg/kg, from about 90 mg/kg to about 280 mg/kg, from about 100 mg/kg to about 250 mg/kg, from about 130 mg/kg to about 230 mg/kg, from about 150 mg/kg to about 200 mg/kg, or from about 200 mg/kg to about 250 mg/kg. Exemplary doses include about 1 mg/kg, about 5 mg/kg, about 10 mg/kg, about 25 mg/kg, about 50 mg/kg, about 75 mg/kg, about 100 mg/kg, about 125 mg/kg, about 150 mg/kg, about 180 mg/kg, about 200 mg/kg, about 225 mg/kg, about 250 mg/kg, about 275 mg/kg, about 300 mg/kg, or about 350 mg/kg. Any of these doses may be administered once daily, twice daily or three times daily, or once a week, once a month or once every three months. In some embodiments, an inhibitor of de novo lipogenesis is administered orally once daily by a tablet or capsule.

In some embodiments, a therapeutically effective amount of a checkpoint inhibitor is from about 1 to about 15 mg/m$^2$, or from about 1 to about 15 mg/m$^2$. In some embodiments, a therapeutically effective amount of a checkpoint inhibitor is from about 10 µg/dose to about 1000 µg/dose, from about 20 µg/dose to about 800 g/dose, from about 30 µg/dose to about 600 µg/dose, from about 40 µg/dose to about 500 µg/dose, from about 50 µg/dose to about 400 µg/dose, from about 60 µg/dose to about 300 µg/dose, from about 70 µg/dose to about 200 µg/dose, or from about 80 µg/dose to about 120 µg/dose.

In some embodiments, a therapeutically effective amount of a checkpoint inhibitor is from about 0.05 mg/kg to about 100 mg/kg, from about 0.1 mg/kg to about 75 mg/kg, from about 0.2 mg/kg to about 50 mg/kg, from about 0.5 mg/kg to about 40 mg/kg, from about 0.5 mg/kg to about 30 mg/kg, from about 0.5 mg/kg to about 20 mg/kg, from about 0.5 mg/kg to about 10 mg/kg, from about 1 mg/kg to about 10 mg/kg, from about 1 mg/kg to about 15 mg/kg, from about 0.5 mg/kg to about 5 mg/kg, or from about 1 mg/kg to about 5 mg/kg. Exemplary doses include about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg. Any of these doses may be administered once daily, twice daily or three times daily, or once a week, once a month, or once every three months.

In some embodiments, a method of treating cancer in a subject comprises administering to the subject from about 100 mg/kg to about 250 mg/kg of an inhibitor of de novo lipogenesis, or a pharmaceutically acceptable salt thereof, and from about 1 mg/kg to about 10 mg/kg a checkpoint inhibitor, or a pharmaceutically acceptable salt thereof. In some embodiments, a method of treating cancer in a subject comprises administering to the subject from about 130 mg/kg to about 230 mg/kg of an inhibitor of de novo lipogenesis, or a pharmaceutically acceptable salt thereof, and from about 0.5 mg/kg to about 5 mg/kg a checkpoint inhibitor, or a pharmaceutically acceptable salt thereof. In some embodiments, a method of treating cancer in a subject comprises administering to the subject from about 200 mg/kg to about 250 mg/kg of an inhibitor of de novo lipogenesis, or a pharmaceutically acceptable salt thereof, and from about 1 mg/kg to about 15 mg/kg a checkpoint inhibitor, or a pharmaceutically acceptable salt thereof. In some aspects of the aforementioned embodiments, the inhibitor of de novo lipogenesis is administered orally (e.g., as a tablet or capsule), and the checkpoint inhibitor is administered intravenously (e.g, by infusion).

In some embodiments, an inhibitor of de novo lipogenesis and a checkpoint inhibitor are administered such that the molar ratio of the inhibitor of de novo lipogenesis, or a pharmaceutically acceptable salt thereof, to the checkpoint inhibitor, or a pharmaceutically acceptable salt thereof, is from about 1000:1 to about 1:50, from about 900:1 to about 1:40, from about 800:1 to about 1:30, from about 700:1 to about 1:20, from about 500:1 to about 1:10, from about 200:1 to about 1:5, or from about 150:1 to about 1:3. In some embodiments, an inhibitor of de novo lipogenesis and a checkpoint inhibitor are administered such that the molar ratio of the inhibitor of de novo lipogenesis, or a pharmaceutically acceptable salt thereof, to the checkpoint inhibitor, or a pharmaceutically acceptable salt thereof, is from about 3:1 to about 1:3, or from about 2:1 to about 1:2. In some aspects of these embodiments, the molar ratio is about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10.

In some embodiments, a method of treating cancer in a subject comprises administering to the subject SSI-4, or a pharmaceutically acceptable salt thereof, and an anti-PD-1 antibody, or a pharmaceutically acceptable salt thereof. In some aspects of these embodiments, SSI-4, or a pharmaceutically acceptable salt thereof, is administered in an amount from about 130 mg/kg to about 230 mg/kg; and an anti-PD-1 antibody, or a pharmaceutically acceptable salt thereof, is administered in an amount from about 0.5 mg/kg to about 5 mg/kg. In other aspects of these embodiments, SSI-4, or a pharmaceutically acceptable salt thereof, is administered in an amount from about 200 mg/kg to about 250 mg/kg; and an anti-PD-1 antibody, or a pharmaceutically acceptable salt thereof, is administered in an amount from about 1 mg/kg to about 15 mg/kg. In further aspects of these embodiments, the anti-PD-1 antibody is pembrolizumab or nivolumab. In yet further aspects of these embodiments, SSI-4, or a pharmaceutically acceptable salt thereof, is administered orally (e.g., as a tablet or capsule), and the anti-PD-1 antibody is administered intravenously (e.g, by infusion).

Kits

The present invention also includes pharmaceutical kits useful, for example, in the treatment of cancer, which include one or more containers containing an inhibitor of de novo lipogenesis, a checkpoint inhibitor, or a pharmaceutical composition comprising same. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Definitions

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans.

As used herein, the phrase "effective amount" or "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

The term, "compound", as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g., hydrates and solvates).

The term "halo" refers to fluoro, chloro, bromo or iodo.

The term "alkyl" refers to a straight or branched chain alkyl group, having from 1-20 carbon atoms. The alkyl is unsubstituted unless otherwise indicated. Illustrative of the alkyl group include the methyl, ethyl, propyl, isopropyl, butyl, isobutyl, sec-butyl, t-butyl, pentyl, 3-methylbutyl, 2,2-dimethylpropyl, 1,1-dimethylpropyl, hexyl, 1-methylpentyl, 4-methylpentyl, heptyl, 1-methylhexyl, 2-methylhexyl, 5-methylhexyl, 3-ethylpentyl, octyl, 2-methylheptyl, 6-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2-methylheptyl, 3,3-diethylhexyl, undecyl, 2-methyldecyl, 9-methyldecyl, 4-ethylnonyl, 3,5-dimethylnonyl, 3-propyloctyl, 5-ethyl-4-methyloctyl, 1-pentylhexyl, dodecyl, 1-methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl, 6-propylundecyl, 4-butyldecyl, 2-pentylnonyl, pentadecyl, 13-methyltetradecyl, 10-ethyltridecyl, 7-propyldodecyl, 5-ethyl-3-methyldodecyl, 4-pentyldecyl, 1-hexylnonyl, hexadecyl, 14-methylpentadecyl, 6-ethyltetradecyl, 4-propyltridecyl, 2-butyldodecyl, heptadecyl, 15-methylhexadecyl, 7-ethylpentadecyl, 3-propyltetradecyl, 5-pentyldodecyl, octadecyl, 16-methylheptadecyl, 5-propylpentadecyl, nonadecyl, 17-methyloctadecyl, 4-ethylheptadecyl, icosyl, 18-methylnonadecyl, 3-ethyloctadecyl, henicosyl, docosinyl, tricosinyl, tetracosinyl and pentacosinyl groups.

The term "$C_{x-y}$ alkyl" refers to an alkyl group between x and y carbon atoms in size. For example, $C_{1-8}$ alkyl refers to an alkyl of 1 to 8 carbon atoms.

The term "aryl" as used herein includes 5-, 6-, and 7-membered unsubstituted single-ring aromatic groups in which each atom of the ring is carbon. The term "aryl" also includes polycyclic ring systems having two cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. The aryl group may be optionally substituted where indicated. Aryl groups include benzene, naphthalene, tetralin, and the like.

The term "haloalkyl" refers to an alkyl group that is substituted with one or more (e.g., 1, 2, 3, 4, or 5) halo substituents. The group is otherwise unsubstituted unless as indicated. Examples include chloroethyl, chloromethyl, difluoromethyl, trifluoromethyl, and the like.

REFERENCES

1. Mellman I, Coukos G, Dranoff G. Cancer immunotherapy comes of age. Nature 2011; 480:480-9.
2. Rosenberg S A. Raising the bar: the curative potential of human cancer mmunotherapy. Sci Transl Med 2012; 4:127ps8.

3. Woo S R, Corrales L, Gajewski T F. Innate immune recognition of cancer. Annu Rev Immunol 2015; 33:445-74.
4. Guo C, Manjili M H, Subjeck J R, Sarkar D, Fisher P B, Wang X Y Therapeutic cancer vaccines: past, present, and future. Adv Cancer Res 2013; 119:421-75.
5. Baenke F, Peck B, Miess H, Schulze A. Hooked on fat: the role of lipid synthesis in cancer metabolism and tumour development. Dis Model Mech 2013; 6:1353-63.
6. Abramson H N. The lipogenesis pathway as a cancer target. J Med Chem 2011; 54:5615-38.
7. Beloribi-Djefaflia S, Vasseur S, Guillaumond F. Lipid metabolic reprogramming in cancer cells. Oncogenesis 2016; 5:e189.
8. Hanahan D, Weinberg R A. Hallmarks of cancer: the next generation. Cell 2011; 144:646-74.
9. Zhang F, Du G. Dysregulated lipid metabolism in cancer. World J Biol Chem 2012; 3:167-74.
10. Santos C R, Schulze A. Lipid metabolism in cancer. FEBS J 2012; 279:2610-23.
11. von Roemeling C A, Marlow L A, Pinkerton A B, et al. Aberrant lipid metabolism in anaplastic thyroid carcinoma reveals stearoyl CoA desaturase 1 as a novel therapeutic target. J Clin Endocrinol Metab 2015; 100: E697-709.
12. von Roemeling C A, Marlow L A, Wei J J, et al. Stearoyl-CoA desaturase 1 is a novel molecular therapeutic target for clear cell renal cell carcinoma. Clin Cancer Res 2013; 19:2368-80.
13. Yahagi N, Shimano H, Hasegawa K, et al. Co-ordinate activation of lipogenic enzymes in hepatocellular carcinoma. Eur J Cancer 2005; 41:1316-22.
14. Roongta U V, Pabalan J G, Wang X, et al. Cancer cell dependence on unsaturated fatty acids implicates stearoyl-CoA desaturase as a target for cancer therapy. Mol Cancer Res 2011; 9:1551-61.
15. Ide Y, Waki M, Hayasaka T, et al. Human breast cancer tissues contain abundant phosphatidylcholine (36 ratio 1) with high stearoyl-CoA desaturase-1 expression. PLoS One 2013; 8:e61204.
16. Noto A, Raffa S, De Vitis C, et al. Stearoyl-CoA desaturase-1 is a key factor for lung cancer-initiating cells. Cell Death Dis 2013; 4:e947.
17. Fucikova J, Moserova I, Urbanova L, et al. Prognostic and Predictive Value of DAMPs and DAMP-Associated Processes in Cancer. Front Immunol 2015; 6:402.
18. Janssens S, Pulendran B, Lambrecht B N. Emerging functions of the unfolded protein response in immunity. Nat Immunol 2014; 15:910-9.
19. Rodvold J J, Mahadevan N R, Zanetti M. Immune modulation by E R stress and inflammation in the tumor microenvironment. Cancer Lett 2016; 380:227-36.
20. Panaretakis T, Kepp O, Brockmeier U, et al. Mechanisms of pre-apoptotic calreticulin exposure in immunogenic cell death. EMBO J 2009; 28:578-90.

EXAMPLES

Figure 1B:
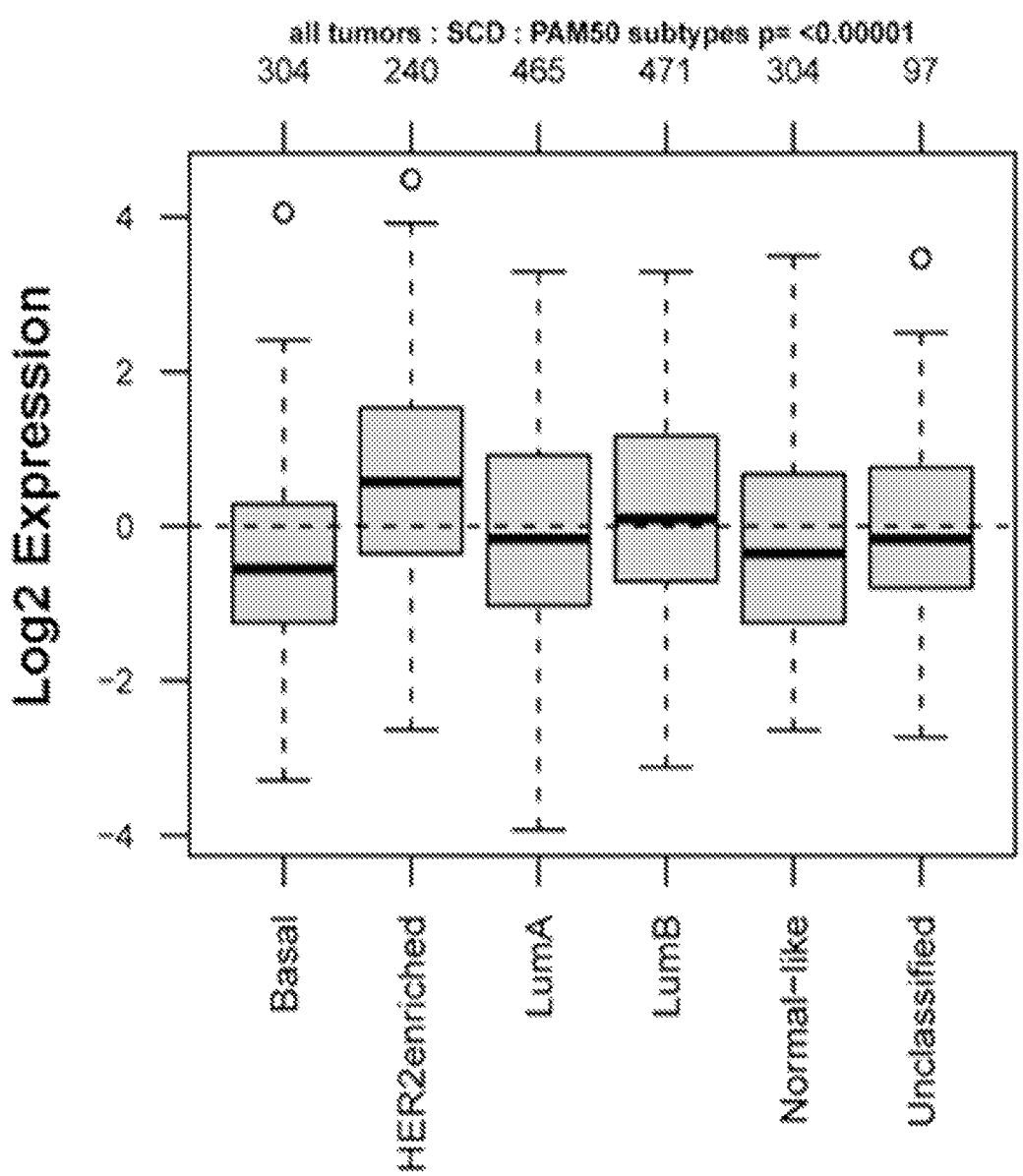
FIG. 1B shows maximal SCD1 over-expression in HER2 enriched breast cancer.
Figure 1C:
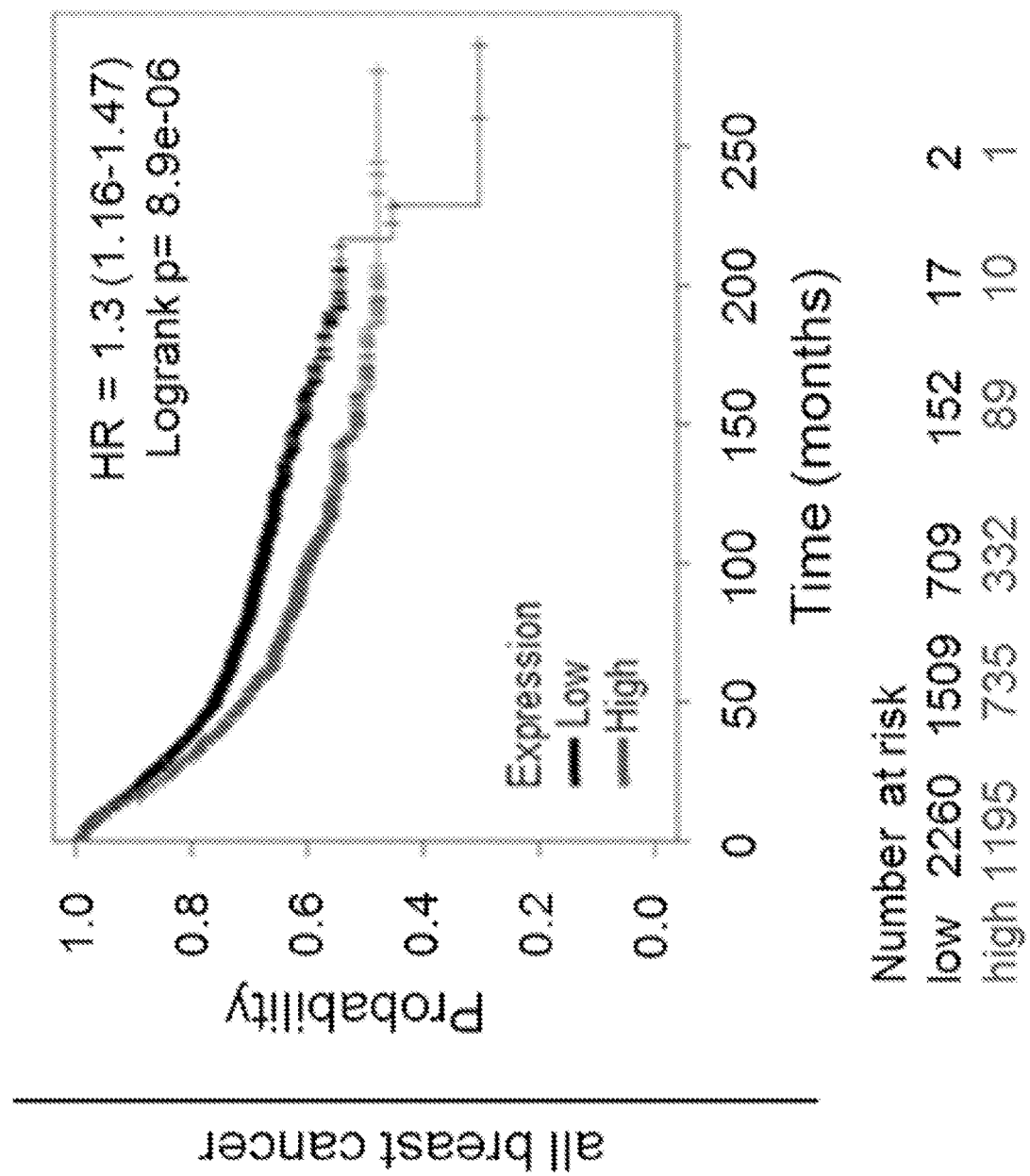
FIG. 1C shows that elevated SCD1 mRNA expression correlates with reduced overall survival in all breast cancer patients.
Figure 1D:
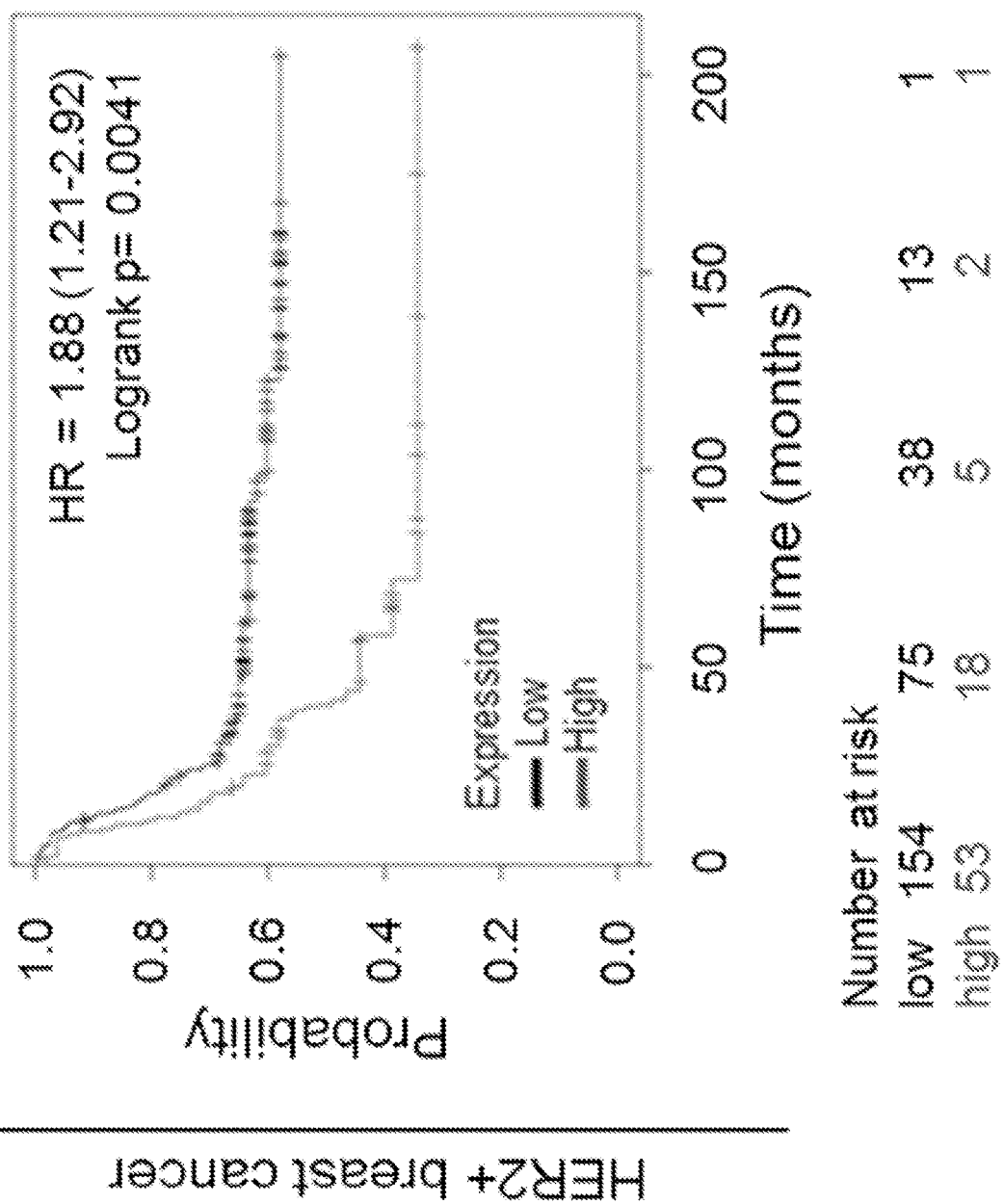
FIG. 1D shows that elevated SCD1 mRNA expression correlates with reduced overall survival in Her2-enriched breast cancer patients.
Figures 2A, 2B:
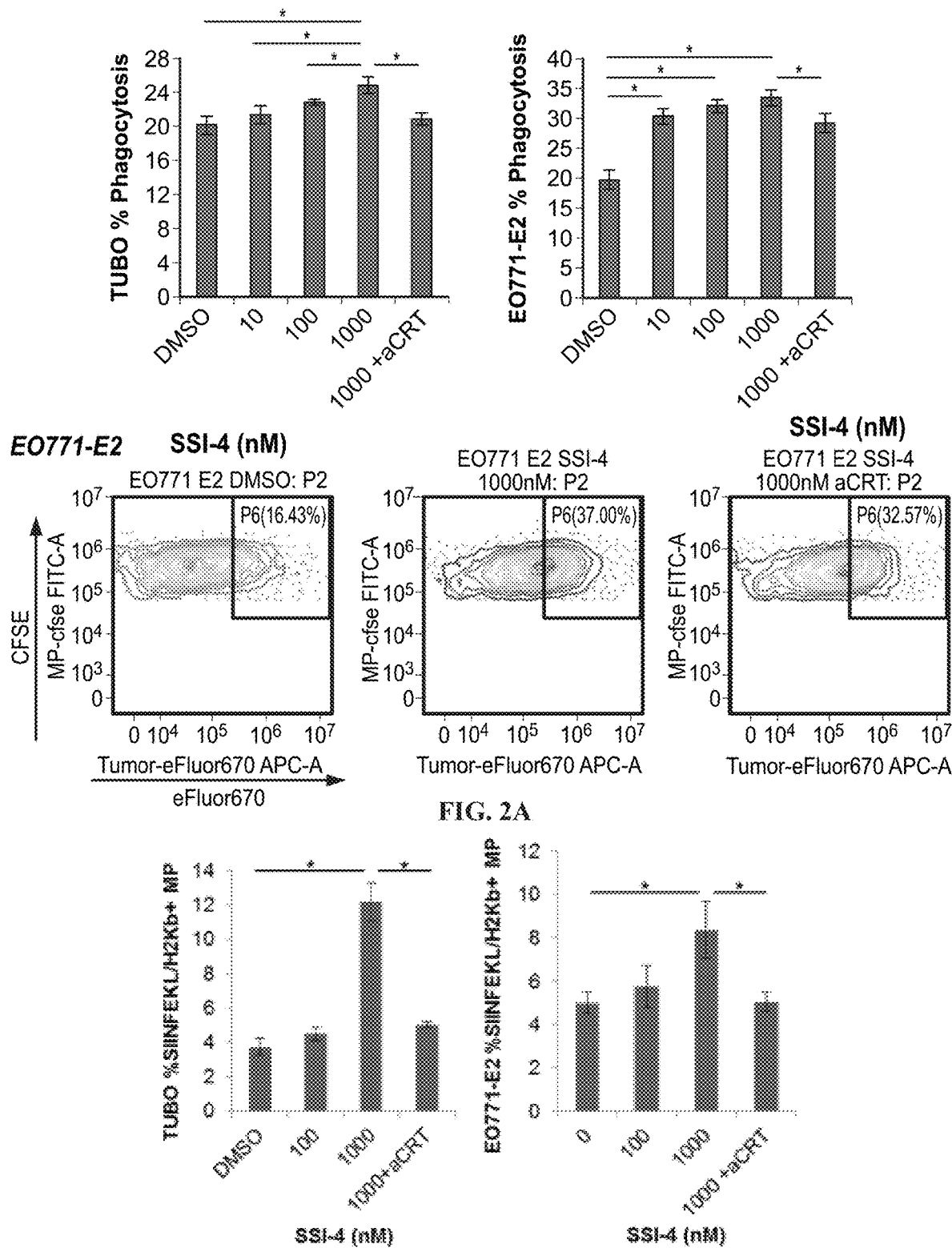
FIG. 2A shows that SSI-4 (1000 nM) induced the highest level of phagocytosis in both TUBO and E0771-E2 cells (5 and 13%, respectively), and this effect is reversed in with adjuvant CRT neutralization.
FIG. 2B shows that SSI-4 treatment (1000 nM) significantly enhanced antigen presentation in both TUBO (8.5%) and E0771-E2 (5%) cells, and that this effect was inhibited with adjuvant CRT neutralization.
Figure 2C:
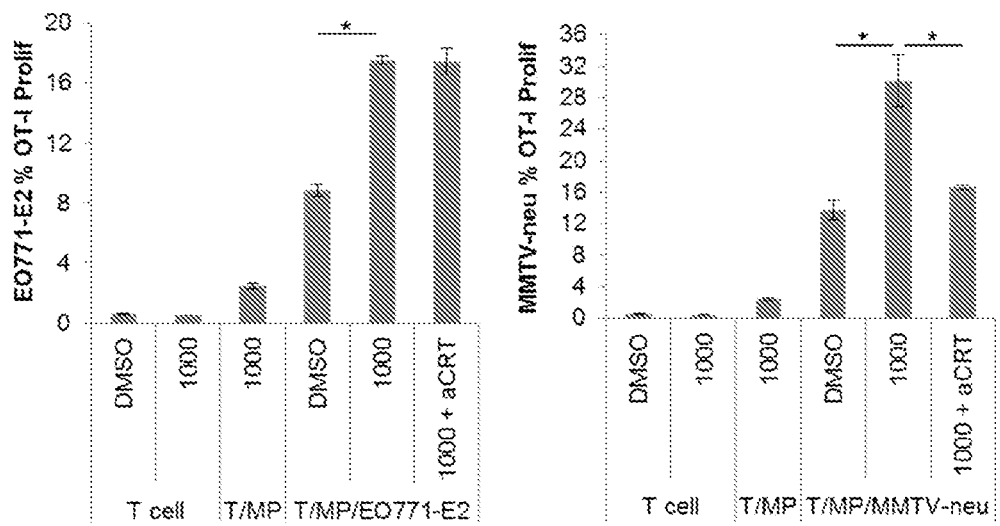
FIG. 2C shows that SSI-4 treatment (1000 nM) significantly enhanced OT-I CD8 T cell proliferation in both E0771-E2 and MMTV-neu cells, and that this effect was inhibited with adjuvant CRT neutralization in MMTV-neu cells. This effect was dependent on the co-presence of macrophages (MP), T cells (T) and tumor cells.
Figure 2D:
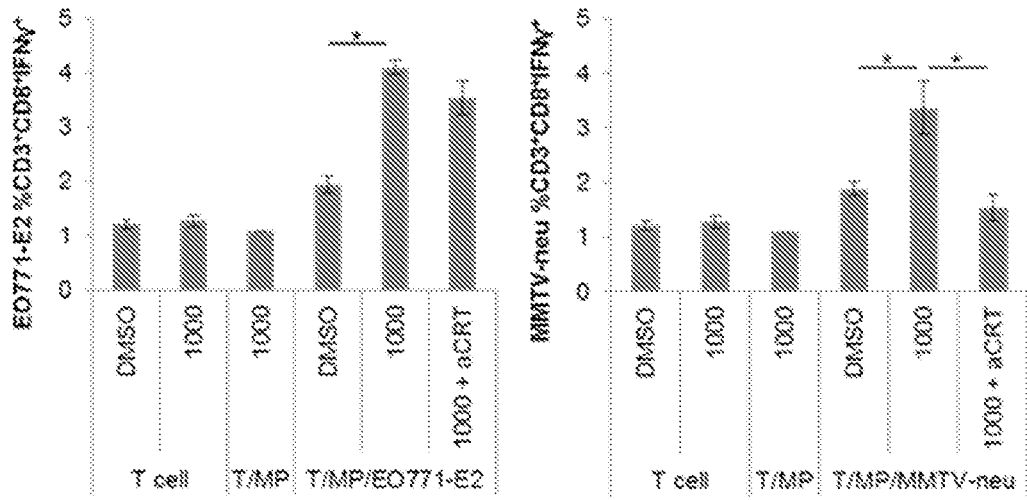
FIG. 2D shows that SSI-4 treatment (1000 nM) significantly enhanced interferon gamma (IFN$\gamma$) production in OT-I CD8 T cells in both E0771-E2 and MMTV-neu cells, and that this effect was inhibited with adjuvant CRT neutralization in MMTV-neu cells. This effect was dependent on the co-presence of macrophages (MP), T cells (T) and tumor cells.

Example 1—SCD1 is Correlated with Poor Patient Outcomes in HER2-Positive Breast Cancer The effects of SCD1 inhibition in clear cell renal cell carcinoma (ccRCC) were investigated. Gene array and ancillary pathway signature analysis of SCD1 inhibitor treated ccRCC cells revealed profound alterations in acute phase inflammatory signaling (FIG. 1a), suggestive that this compound may influence tumor cell inflammatory reprogramming. SCD1 inhibitors could behave as immunosensitizing agents in cancer. To determine the effects of SSI-4 in tumor immunity, an appropriate immune-competent model of carcinogenesis was identified. SCD1 mRNA expression is increased in breast cancer. The online platform Gene expression-based Outcome for Breast cancer Online (GOBO) for SCD1 expression among different subtypes of breast cancer was searched and maximal SCD1 over-expression in HER2 enriched breast cancer was determined (FIG. 1b). Using this platform patient samples were stratified by subtype and the relationship between patient overall survival and SCD1 expression was examined. While high SCD1 expression is correlated with a mild decrease in patient overall survival (OS) in all breast cancer (FIG. 2c), HER2-enriched patients with elevated SCD1 expression had a marked decrease in OS as compared to SCD1-low patients (FIG. 2d). In the following examples, the role of SSI-4 mediated tumor immunogenicity in HER2-enriched breast cancer was shown using 4 murine tumor models: TUBO, E0771-E2, N202, and MMTV-neu.

Example 2—SSI-4 Induces Translocation of Calreticulin to the Plasma Membrane

Figure 1E:
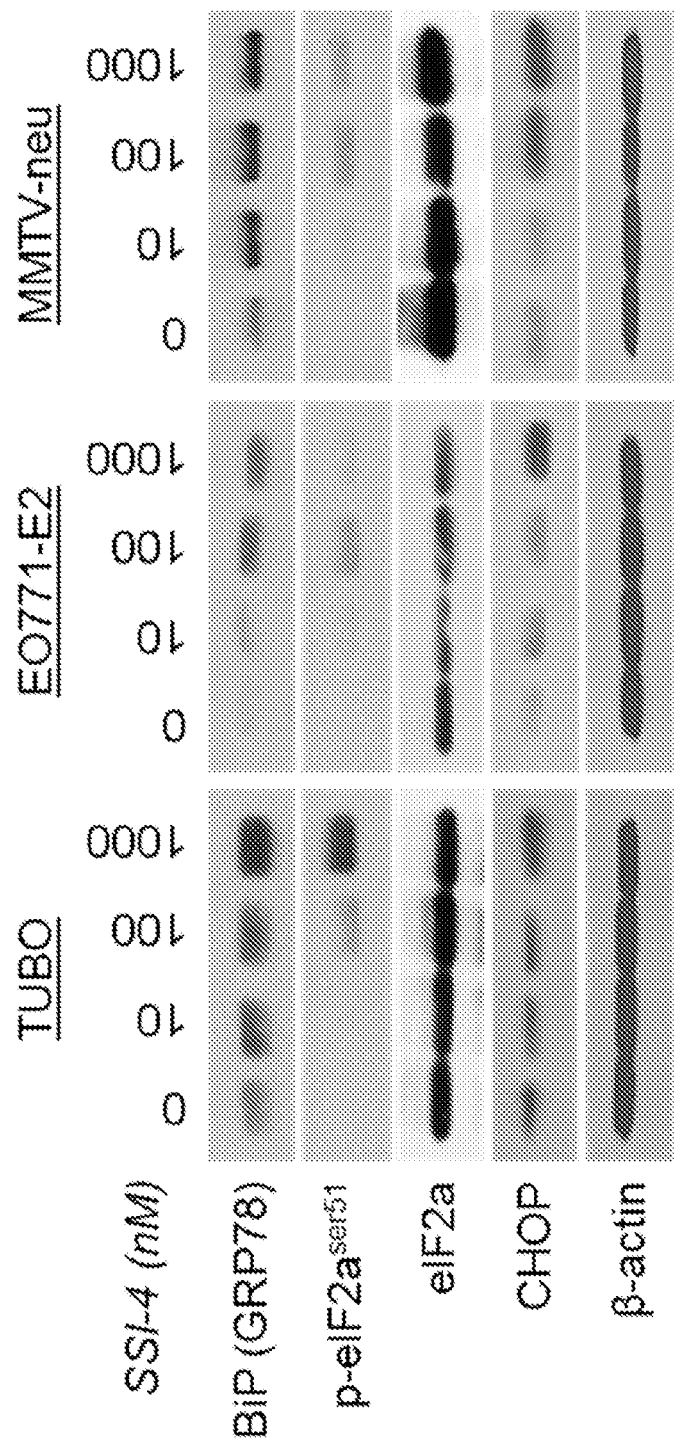
FIG. 1E shows increased levels of endoplasmic reticulum stress response factors including binding immunoglobulin protein (BiP, GRP78), total phosphorylated eukaryotic translation initiation factor 2A (eIF2A) at serine51 and DNA damage inducible transcript 3 (CHOP, DDIT3) in TUBO, E0771-E2, and MMTV-neu tumor cells.
Figure 1F:
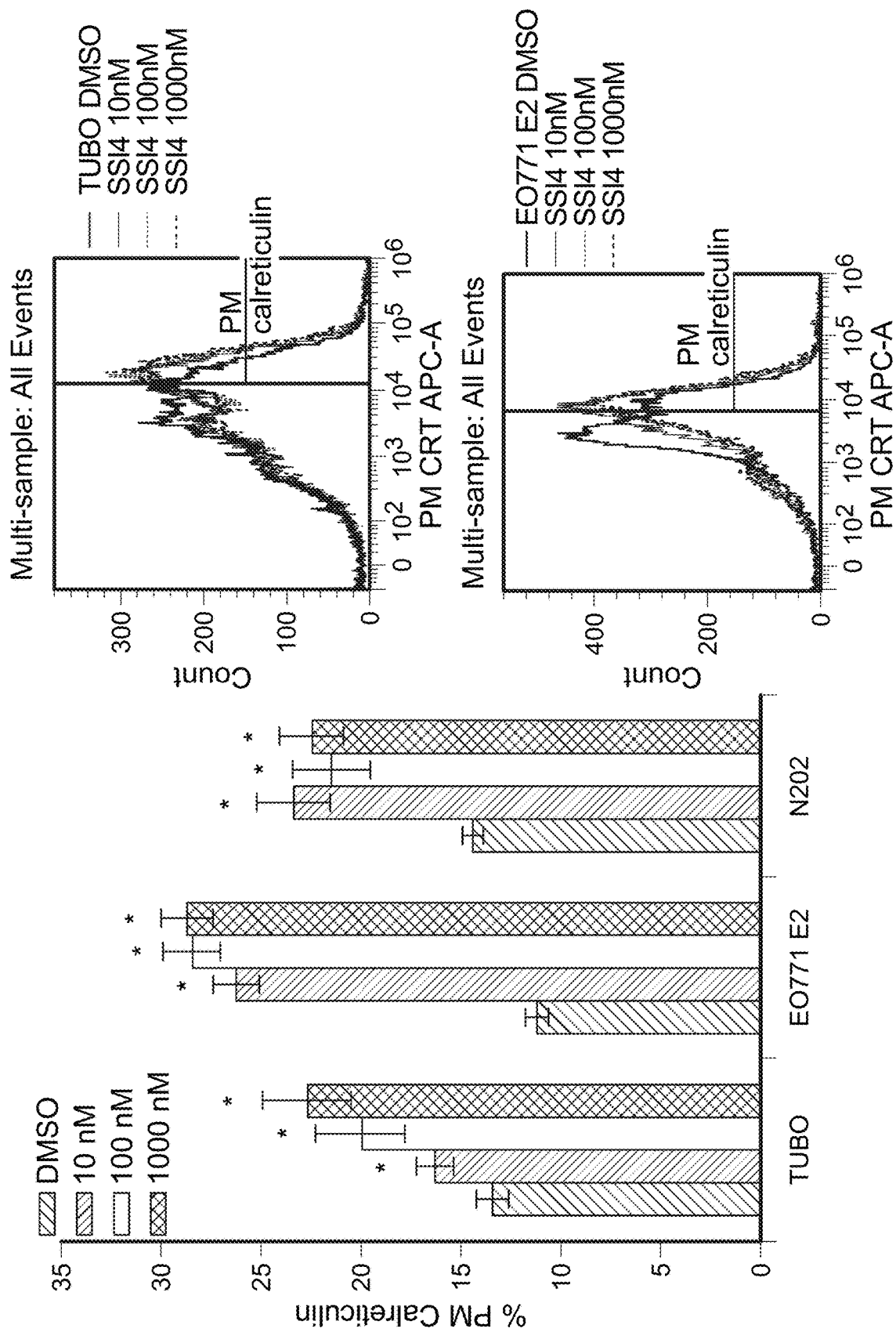
FIG. 1F shows results of flow cytometry on live tumor cells following a 48 hour treatment with SSI-4 at 10 nM, demonstrating that SSI-4 induces plasma membrane translocation of calreticulin, a known immunogenic cell death inducer.

SSI-4 induces ER stress in tumor cells. Treatment of TUBO, E0771-E2, and N202 tumor cells with SSI-4 (10-1000 nM) resulted in activation of ER stress as shown by increased levels of phosphorylated eukaryotic translation initiation factor 2 alpha (eIF2α) at serine51 and DNA damage inducible transcript 3 (CHOP, DDIT3) (FIG. 1e). ER stress can provoke a therapeutically relevant adaptive immune response against malignant cells through the emission of immunostimulatory signals, or damage-associated molecular patterns (DAMPs) such as heat shock proteins and translocation of calreticulin (CRT) to the plasma membrane (17). In particular, phosphorylation of eIF2a has been reported to mediate CRT translocation (20) which is correlated with the induction of immunogenic cell death (ICD) and favorable disease outcome in a variety of malignancies (17). SSI-4 potently upregulates plasma membrane expression of CRT at doses as low as 10 nM, as measured by flow cytometry on live tumor cells following a 48 hour treatment (FIG. 1f).

Example 3—SSI-4 Treatment Instigates Adaptive Immunity In Vitro

CRT behaves as a pro-phagocytic signal. The effect of SSI-4 treatment on tumor cell phagocytosis by bone marrow-derived macrophages (BMDM) in vitro was determined. SSI-4 (1000 nM) induced the highest level of phagocytosis in both TUBO and E0771-E2 cells (5 and 13%, respectively) (FIG. 2a). Neutralization of CRT using a blocking antibody was able to significantly abrogate this effect in both cell models, suggesting that SSI-4 mediated phagocytosis is due in part to CRT translocation (FIG. 2a). Downstream activation of T lymphocytes is dependent on the successful maturation and presentation of antigen by antigen-presenting cells such as macrophages (Woo 2015). SSI-4 driven activation of BMDMs in vitro was evaluated by measuring antigen presentation of chicken ovalbumin (cOva) by MHC class I receptors on BMDM after co-culturing them with cOva-expressing tumor cells. SSI-4 treatment (100 nM) significantly enhanced antigen presentation in both TUBO (8.5%) and E0771-E2 (5%) cells, and this effect was inhibited with adjuvant CRT neutralization (FIG. 2b). CD8+ T lymphocyte activation was evaluated in vitro using splenic T cells derived from OT-I transgenic mice which recognize ovalbumin residues 257-264 in the context of H2Kb. Proliferation and interferon gamma (IFNγ) production was measured in T lymphocytes co-cultured with both cOva-expressing tumor cells and BMDM treated with SSI-4. In addition, in order to evaluate whether the effects of SSI-4 on T lymphocyte activation were direct or mediated through a tumor-specific mechanism, concurrent analysis in SSI-4 treated T lymphocytes alone and T lymphocytes co-cultured with BMDM only was performed. SSI-4 (1000 nM) was able to potently induce CD8+ T lymphocyte proliferation as well as IFNγ production in both E0771-E2 and MMTV-neu triple cultures (FIG. 2c-d). CRT neutralization was able to abrogate these effects in MMTV-neu cells, while a mild (n.s.) decrease in IFNγ production was observed in E0771-E2 cells (FIG. 2c-d). SSI-4 driven CRT translocation is a contributor to these results. No significant changes in T lymphocyte proliferation or IFNγ production were observed in alone or T lymphocyte-BMDM co-cultures, e.g., activation occurs in a tumor-specific antigen-mediated manner (FIG. 2c-d).

Example 4—SSI-4 Demonstrates Anti-Tumor Activity in Immune-Competent Mice

Figure 3A:
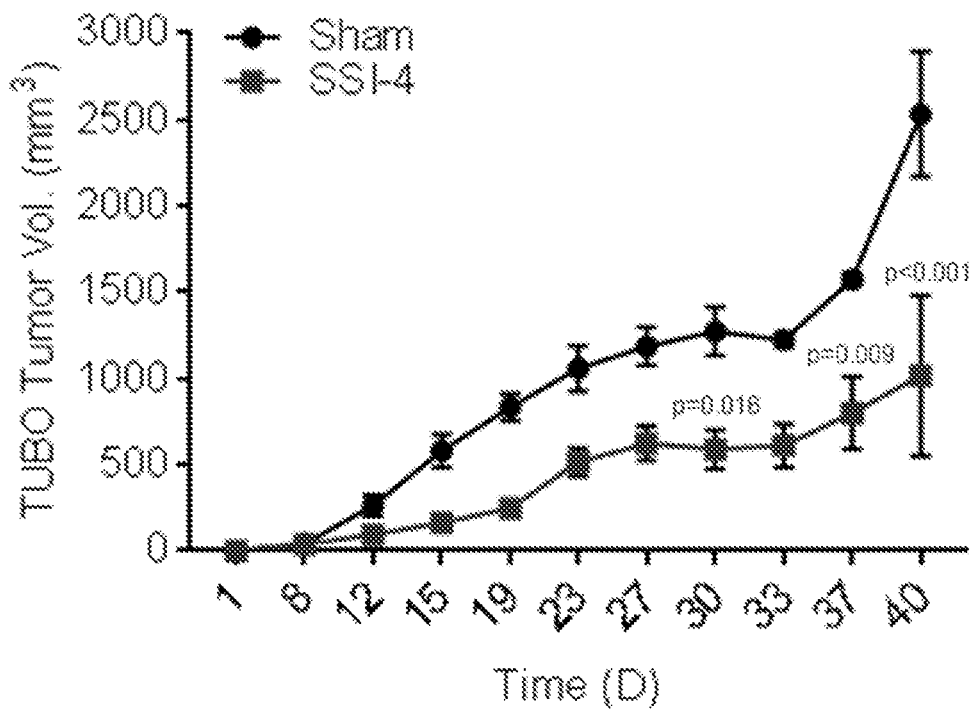
FIG. 3A shows that SSI-4 treated animals demonstrated slower tumor progression, with markedly smaller tumor sizes recorded at 30 days after onset of therapy when control animals reached endpoint.
Figure 3B:
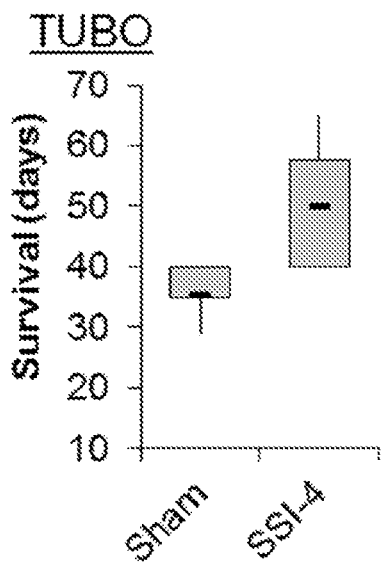
FIG. 3B shows an appreciable increase in overall survival in SSI-4 treated mice.
Figure 3C:
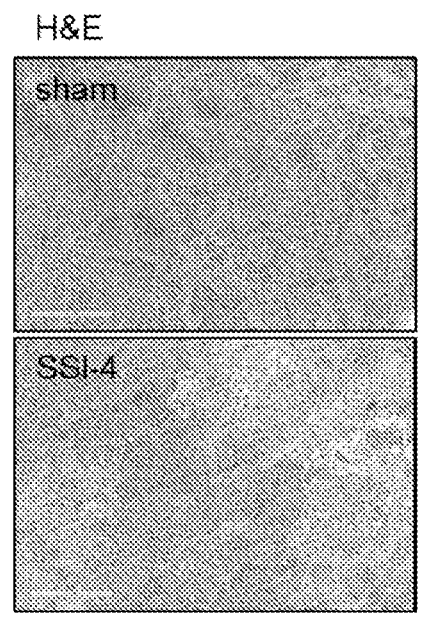
FIG. 3C shows that H&E staining of tumor sections did not reveal conspicuous changes in overall tissue morphology between sham and SSI-4 treatment groups.
Figure 3D:
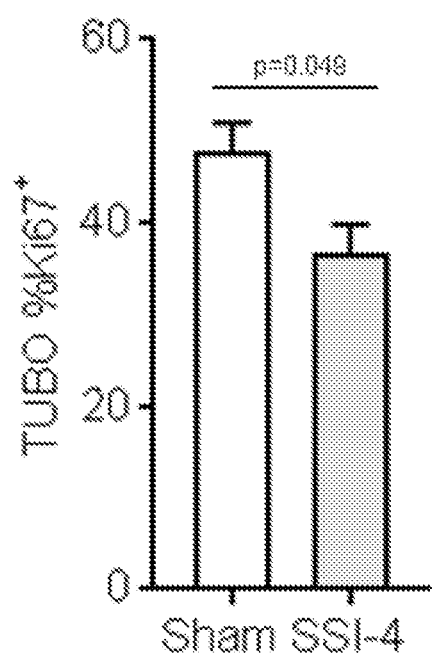
FIG. 3D shows a significant decrease in Ki-67 protein staining, indicative of decreased tumor proliferation was noted in the SSI-4 group. (%+nuclei=47.7±6.4 for sham, %+nuclei=36.7±6.2 for SSI-4).
Figure 3D:
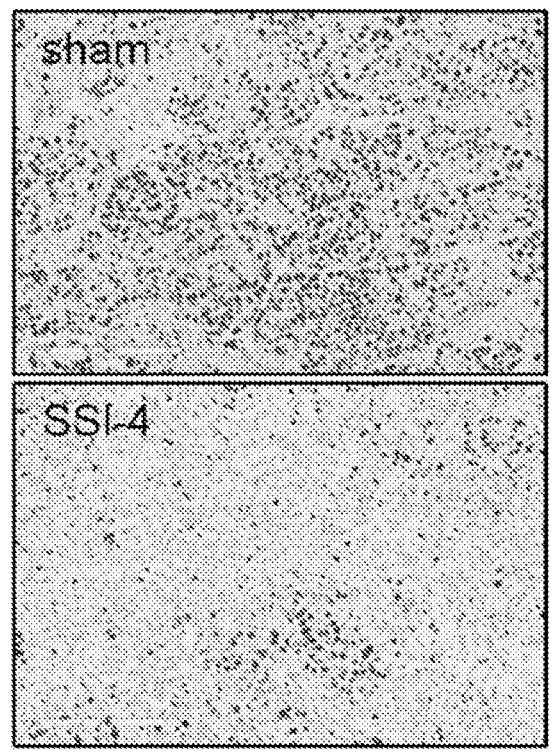
Figure 3E:
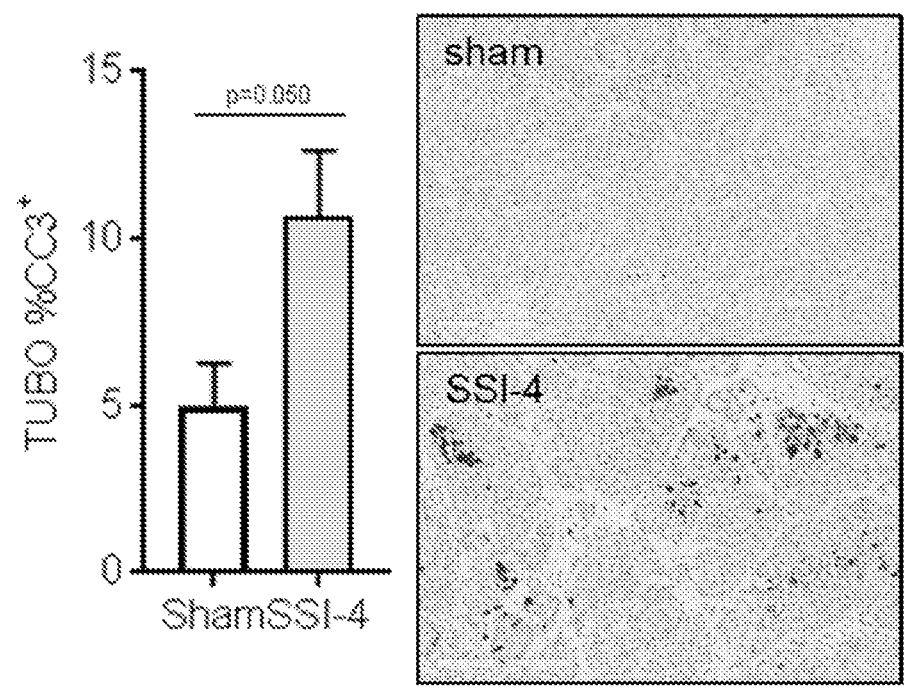
FIG. 3E shows a significant increase in cleaved caspase 3 (CC3) staining, indicative of enhanced tumor apoptosis was noted in the SSI-4 group. (H=4.9±2.6 for sham, H=10.7±3.9 for SSI-4).

SSI-4 mediated immunomodulation in vivo was evaluated. TUBO cells were injected orthotopically into the mammary fat pad of BALB/c mice. Animals received either sham or SSI-4 (180 mg/kg) orally (continuous) when tumor burden reached 50-100 mm$^3$. SSI-4 treated animals demonstrated slower tumor progression, with markedly smaller tumor sizes recorded at 30 days after onset of therapy when control animals reached endpoint (FIG. 3a). An appreciable increase in overall survival was seen in SSI-4 treated mice (FIG. 3b). Tumor tissue was harvested 14 days after treatment onset for analysis. H&E staining of tumor sections did not reveal conspicuous changes in overall tissue morphology between sham and SSI-4 treatment groups (FIG. 3c), however a significant reduction in the proliferative capacity of SSI-4 treated tumors was recorded via decreased nuclear Ki67 staining (FIG. 3c). In addition, a significant increase in cleaved caspase 3 (CC3) staining, indicative of enhanced tumor apoptosis was noted in the SSI-4 group (FIG. 3d).

Figure 3F:
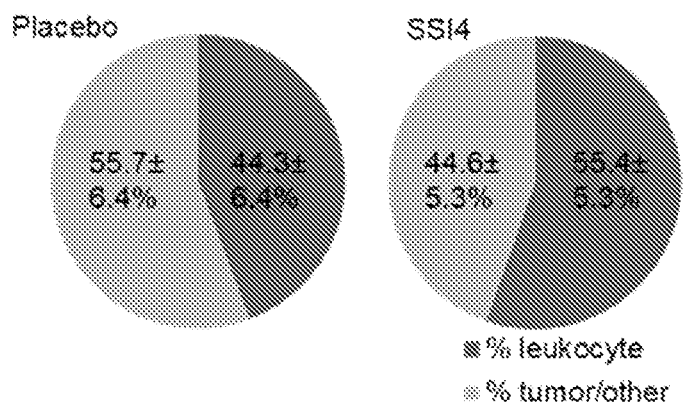
FIG. 3F shows 10% increase in the number of tumor-associated leukocytes within SSI-4 treated animals.
Figure 3G:
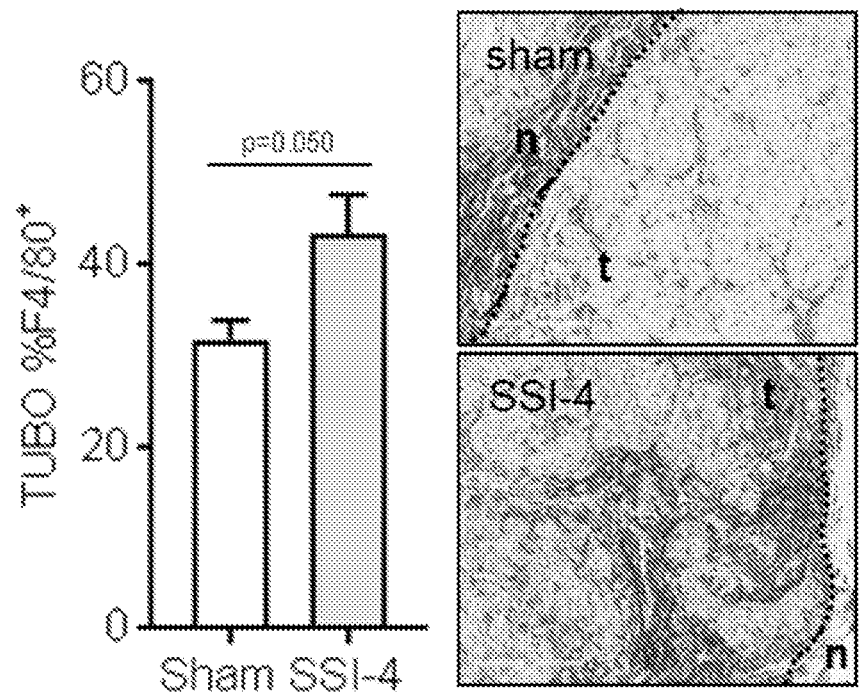
FIG. 3G shows that SSI-4 treated tumors demonstrated increased intra-tumor penetration of macrophages, identified by positive F4/80 IHC staining. (% pop.=31.7±4.1, % pop.=43.3±8.6).
Figure 3H:
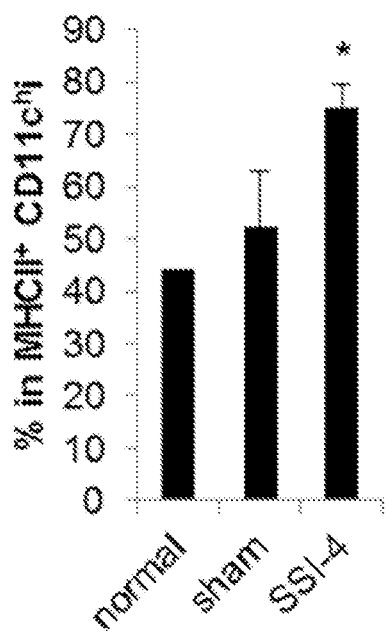
FIG. 3H shows a significant increase in the number of intra-tumor dendritic cells within SSI-4 treated tumors as compared to both control treated tumors, and normal mammary tissue from non-tumor bearing mice.
Figure 3I:
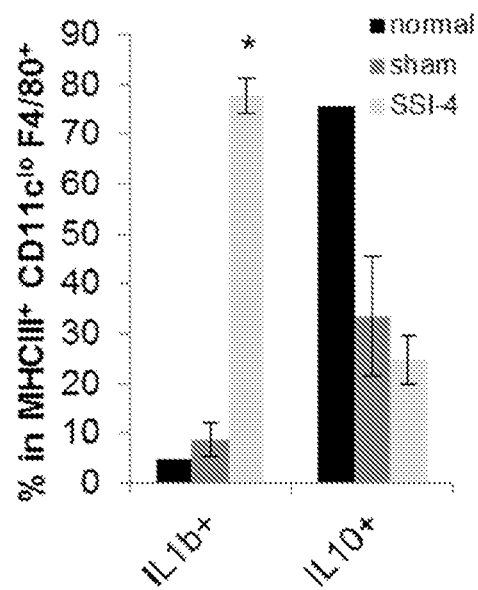
FIG. 3I shows that macrophages isolated from SSI-4 treated tumors demonstrate increased expression of pro-inflammatory cytokines, and decreased expression of immunosuppressive cytokines as compared to control treated tumors, and normal mammary tissue from non-tumor bearing mice.

Example 5—SSI-4 Treatment Enhances Immunogenicity of Poorly-Immunogenic Breast Cancer As SSI-4 treatment of tumor cells enhances the antigen presenting capabilities of APCs in vitro, tumor-associated recruitment of professional phagocytes in vivo including macrophages (MP) and dendritic cells (DC) was evaluated. The ratio of tumor leukocyte recruitment by comparing the ratio of cluster of differentiation 45 antigen (CD45) positive to negative cells sorted from dissociated tumor tissue within control and SSI-4 treated mice was determined. Results indicated a 10% increase in the number of tumor-associated leukocytes within SSI-4 treated animals (FIG. 3f). Next, tumor sections were stained for F4/80, a macrophage (MP) marker. SSI-4 treated tumors demonstrated expanded expression of MPs, as well as increased intra-tumor penetration of these cells toward the tumor core (FIG. 3g). To determine intra-tumor dendritic cell infiltration, tumors were dissociated and analyzed via flow cytometry for DCs based on CD45$^+$MHCII$^+$CD11c$^{hi}$ expression. A significant increase in the number of intra-tumor DCs within SSI-4 treated animals as compared to both control treated tumors and normal, non-tumor bearing mice (FIG. 3h) was observed. As tumor-associated macrophage (TAM) cells can be correlated with either a tumor-suppressive or pro-inflammatory phenotype, we sorted this population identified by MHCII$^+$CD11c$^{lo}$F4/80$^+$ based on the polarization markers interleukin-1β (IL-1β) and IL-10, comparing the expression profiles from both treatment groups as well as mammary tissue extracted from non-tumor bearing mice. While no changes were observed between sham and SSI-4 treated TAM for IL-10, an immunosuppressive cytokine, a significant increase in IL-1β, a cytokine produced by mature macrophages and indicative of pro-inflammatory activation, was observed in response to SSI-4 treatment (FIG. 3i). These data support that SSI-4 promotes the recruitment of pro-inflammatory antigen presenting cells (APCs) into the tumor microenvironment in vivo.

Figure 4A:
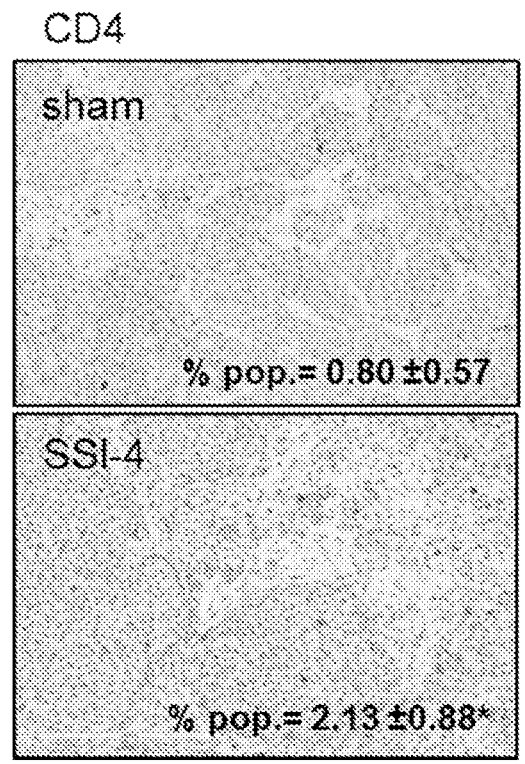
FIG. 4A shows an increase in the number of CD4+ tumor-infiltrating populations in SSI-4 treated tumors.
Figure 4B:
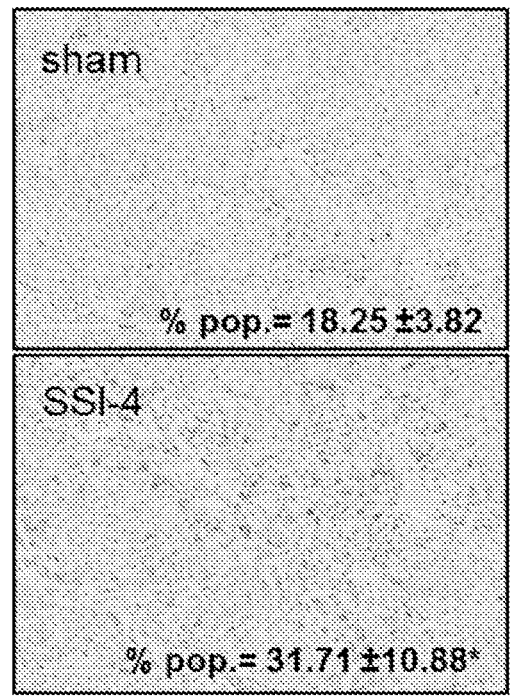
FIG. 4B shows an increase in the number of CD8+ tumor-infiltrating populations in SSI-4 treated tumors.
Figure 4C:
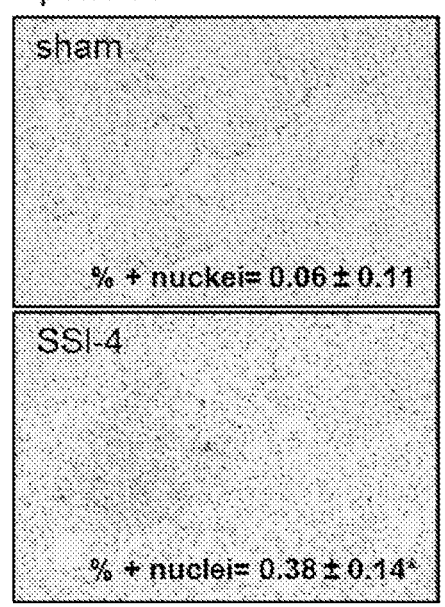
FIG. 4C shows an increase in perforin in SSI-4 treated tumors.
Figure 4D:
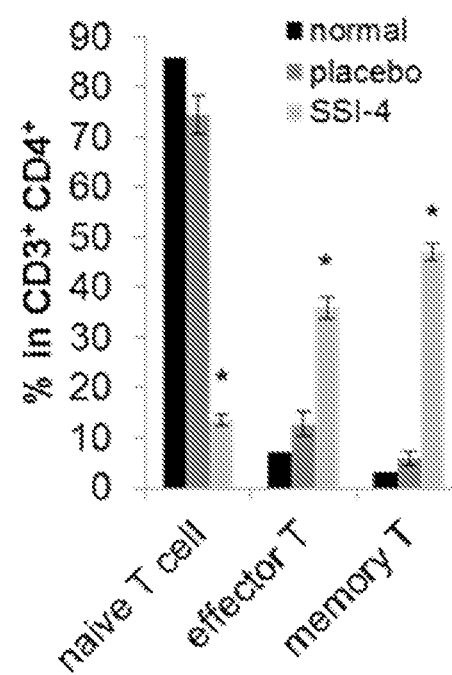
FIG. 4D shows that SSI-4 treatment produced a robust induction of memory and effector T-cells among CD4 positive T cell populations.
Figure 4E:
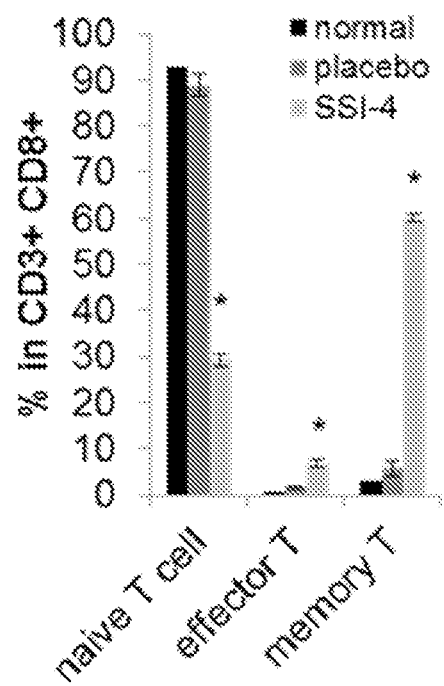
FIG. 4E shows that SSI-4 treatment produced a robust induction of memory and effector T-cells among CD8 positive T cell populations.
Figure 4F:
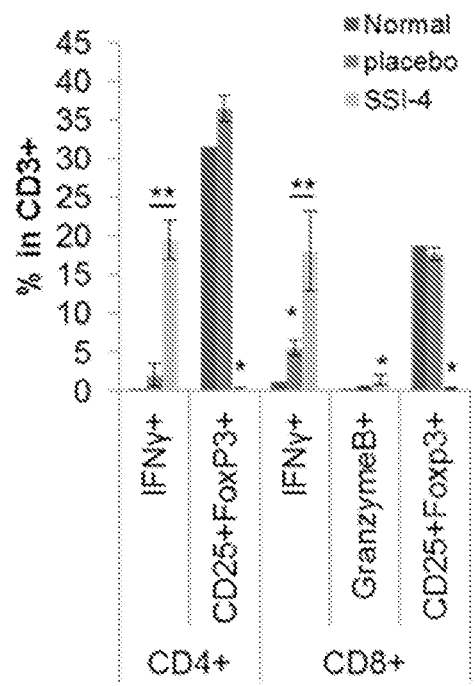
FIG. 4F shows that effector CD4 and CD8 T lymphocytes identified by IFN$\gamma$ was markedly increased in both CD4 and CD8+ T cell populations from SSI-4 treated tumors. SSI-4 also significantly reduced the number of intra-tumor CD4+ T regulatory cells identified by dual CD25 and FoxP3 expression.

SSI-4 mediated APC activation could augment T lymphocyte infiltration and activation. IHC analysis of tumor sections for T lymphocyte distribution revealed a significant increase in the number of both CD4+ and CD8+ tumor-infiltrating populations (FIG. 4a-b). A significant increase in perforin, a cytolytic protein produced by activated cytotoxic T lymphocytes responsible for tumor cell lysis during ICD, was observed in SSI-4 treated tumors (FIG. 4c). The maturation status of T lymphocytes from CD3+ cells isolated from the spleen of treated animals by comparing the ratio of CD44 to CD62L expression in either CD4 or CD8 T-cells was examined. SSI-4 treatment produced a robust induction of memory and effector T-cells among both CD4 and CD8 positive populations; along with a concomitant decrease in naïve T-cell numbers (FIG. 4d-e). The activation status of T lymphocytes isolated from digested tumors was also assessed. The number of effector CD4 and CD8 T lymphocytes identified by IFNγ, a cytokine predominantly produced by activated cytotoxic lymphocytes, was markedly increased in both CD4 and CD8+ populations with SSI-4 (FIG. 4f). Granzyme B-positive CD8 T-cells were also enriched in SSI-4 treated tumors (FIG. 4f), another marker for activated CD8+ T lymphocytes. In parallel, SSI-4 treatment corresponded with a profound decrease in the number of CD4 and CD8 positive intra-tumor regulatory T lymphocytes (T$_{reg}$), characterized by dual CD25 and FoxP3 expression (FIG. 4f). Collectively, these data indicate that SSI-4 is able to bolster intratumor TIL recruitment and maturation, and promoting ICD in HER2 positive breast cancer cells.

Example 6—SSI-4 Augments PD-1 Blockade Mediated Anti-Tumor T Cell Immunity

Materials and methods: The checkpoint inhibitor used was a mouse anti-PD-1 that was purchased from BioXCell (catalog #BE0146). The checkpoint inhibitor was administered at 100 μg/dose (5 mg/kg) by intraperitoneal (IP) injection.

Figure 4G:
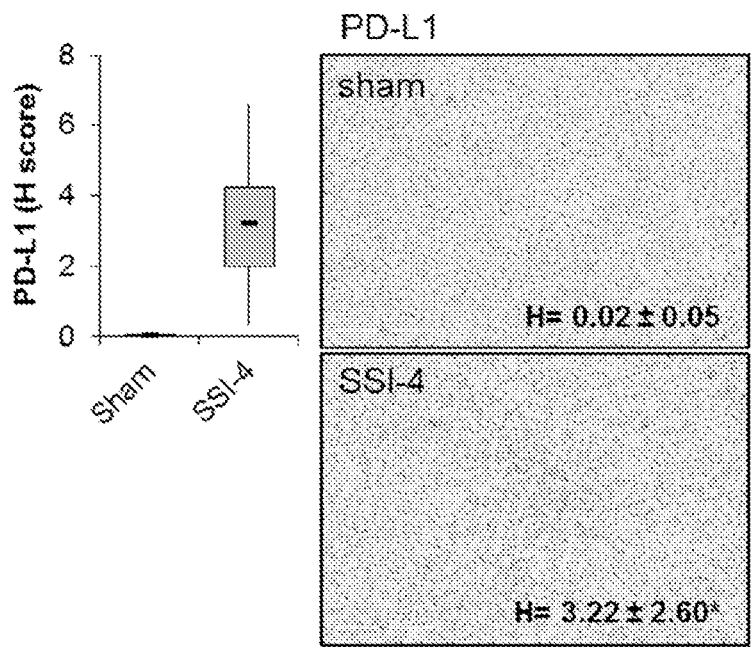
FIG. 4G shows that SSI-4 treatment induces programmed death ligand-1 (PD-L1) expression in TUBO tumor bearing mice.
Figure 5A:
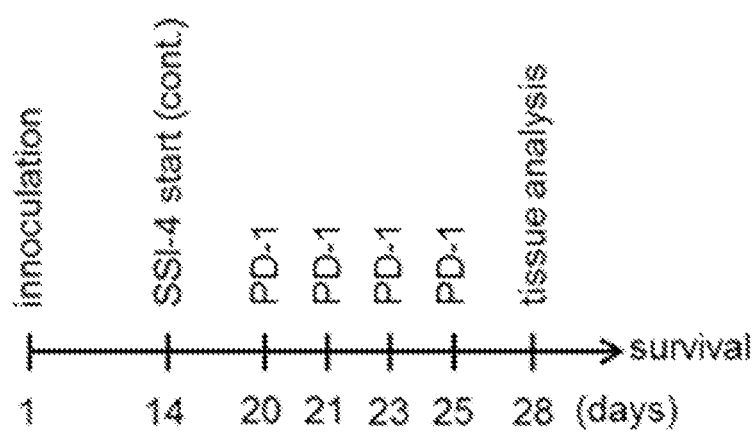
FIG. 5A Is an example treatment schedule for mice receiving combination therapy including SSI-4 and PD-1 checkpoint blockade.
Figure 5B:
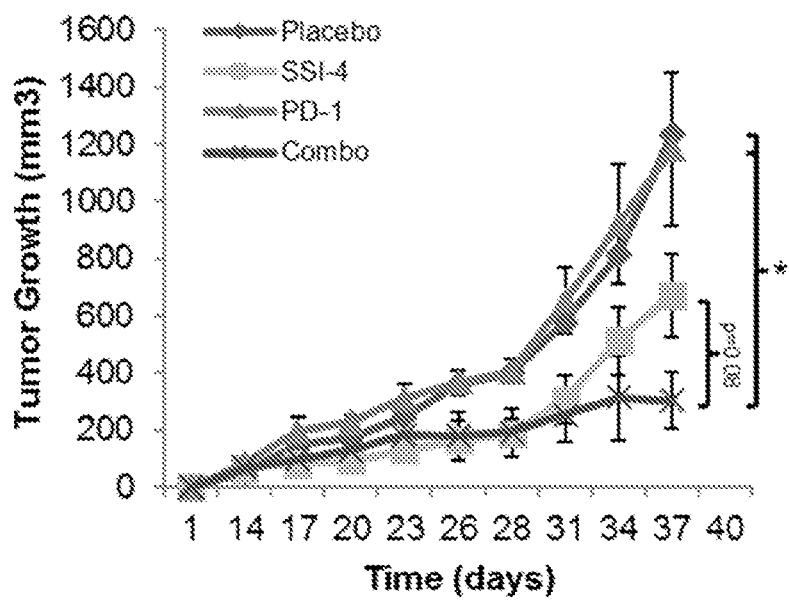
FIGS. 5B-5C show that E0771-E2 tumors do not respond to monotherapeutic PD-1 blockade; combination of PD-1 blockade with SSI-4 produced a more durable anti-tumor response (5B); median survival in the combination group increased by approximately 45% compared to both placebo and PD-1 alone, and 20% as compared to SSI-4 monotherapy.
Figure 5C:
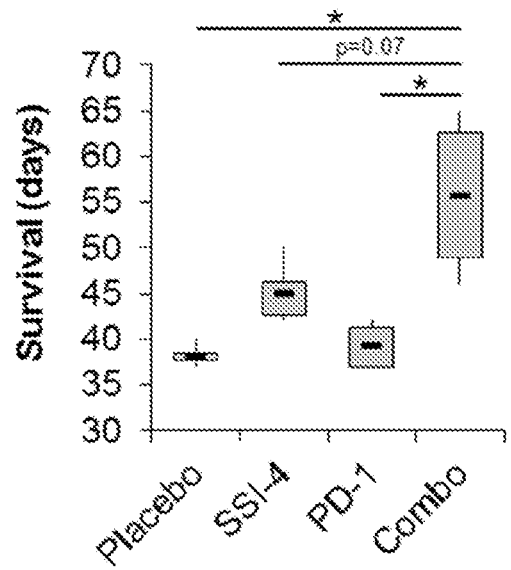
Figure 5D:
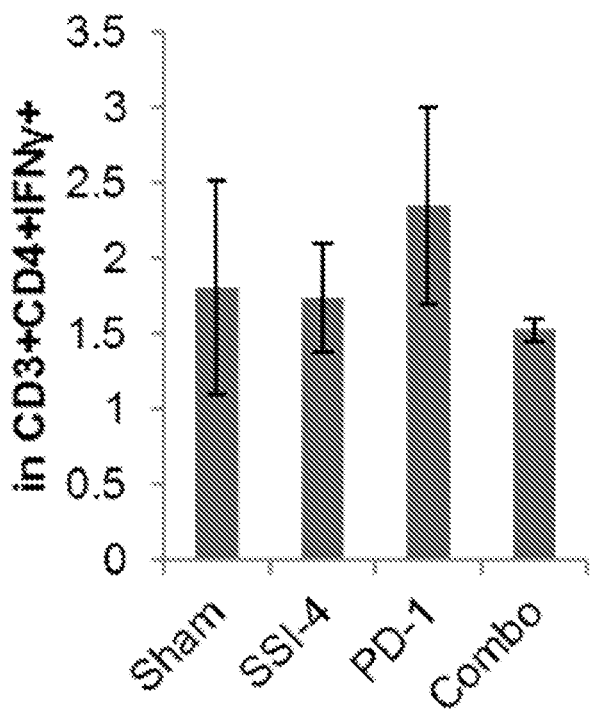
FIGS. 5D-5E show an increase in effector CD8+ cytotoxic T lymphocytes in response to SSI-4 and combination therapy.
Figure 5E:
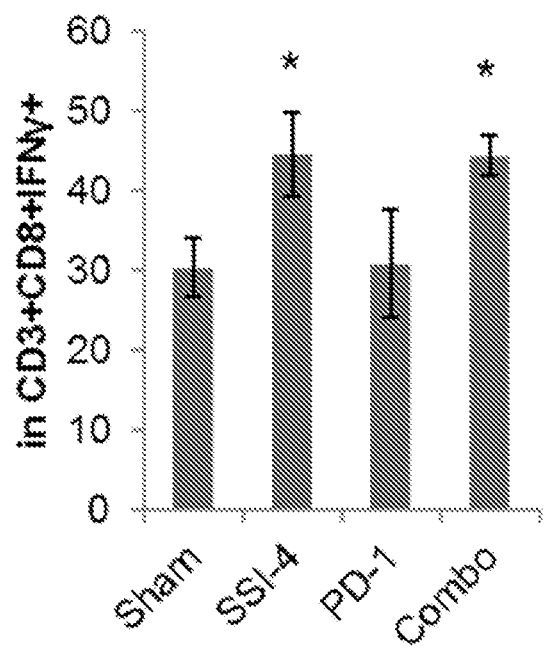
Figure 5F:
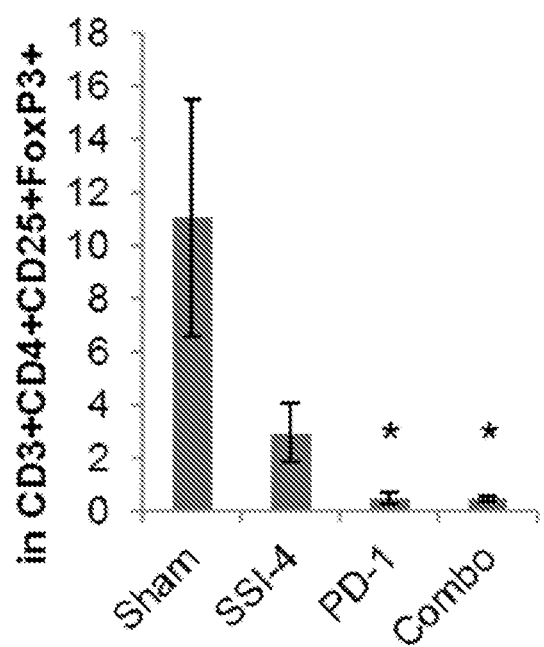
FIG. 5F shows that PD-1 monotherapy and combination therapy had a deleterious effect on the intratumor population of T regulatory cells.
Figure 5G:
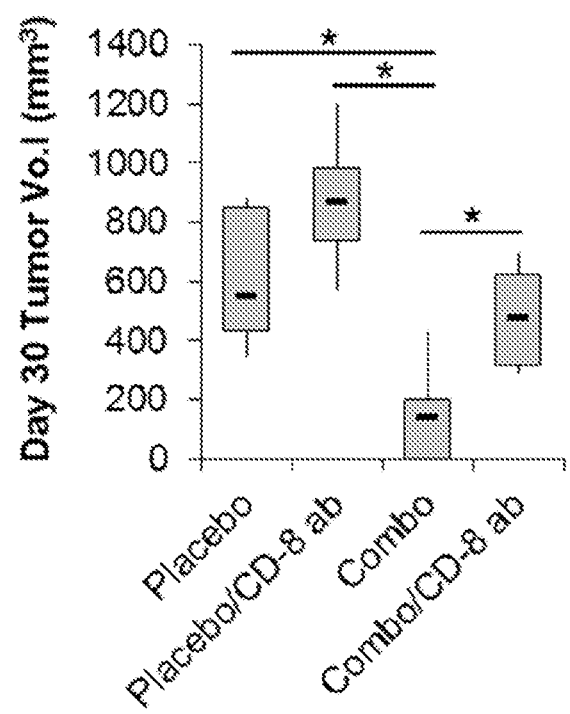
FIG. 5G shows that depletion of CD8 T lymphocytes rescued the anti-tumor activity of the combination treatment.
Figure 5H:
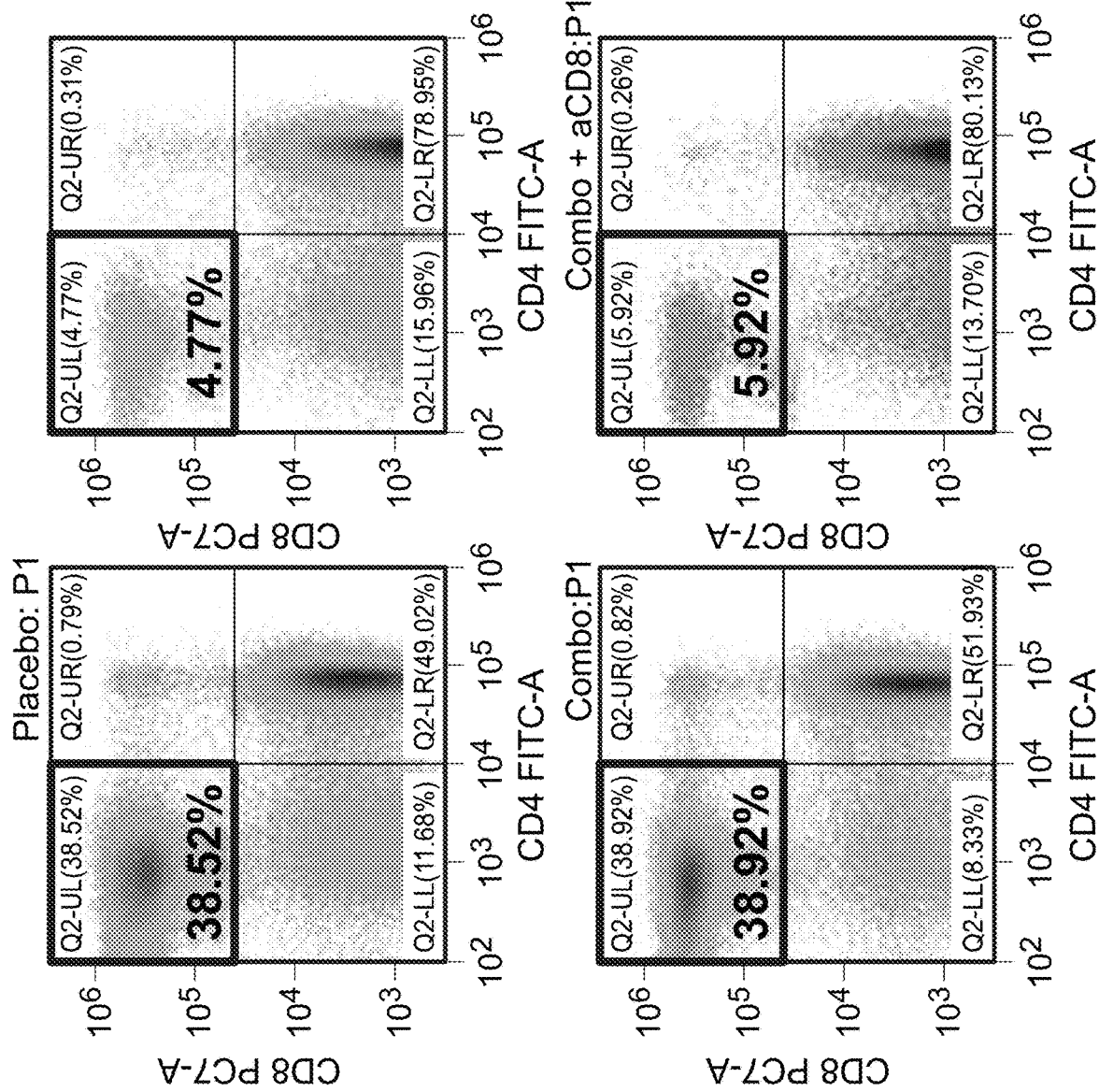
FIG. 5H shows splenic depletion of CD8 T-cells in animals receiving CD-8 blockade.

As tumor progression invariably occurred in SSI-4 treated mice, possible mechanisms of resistance were explored. Tumor-mediated upregulation of immunosuppressive checkpoints promotes T lymphocyte anergism, thus enhancing tumor resistance to immunotherapy (Woo 2015). IHC analysis of tumor sections revealed that SSI-4 treatment induces programmed death ligand-1 (PD-L1) expression in TUBO tumor bearing mice (FIG. 4g). To negate the effects of PD-L1 upregulation, the combination of PD-1 antibody-mediated blockade, the receptor for PD-L1, and SSI-4, was tested. In E0771-E2 tumor bearing mice, anti-PD-1 therapy produced no survival benefit, and tumor burden was comparable to placebo, demonstrating that these tumors do not respond to monotherapeutic PD-1 blockade (FIG. 5b-c). The combination of PD-1 blockade with SSI-4 produced a more durable anti-tumor response as compared to both monotherapies and control treated animals, as evidenced by decreased tumor burden in this group once the placebo group reached endpoint parameters (FIG. 5b). Median survival in the combination group increased by approximately 45% compared to both placebo and PD-1 alone, and 20% as compared to SSI-4 monotherapy (FIG. 5c). Tumor dissociation and isolation and characterization of T-lymphocytes revealed a significant increase in effector CD8+ cytotoxic T lymphocytes in response to SSI-4 and combination therapy (FIG. 5d-e), suggesting that these cells may play more of a prominent role in mediating anti-tumor responsiveness of the treatment. PD-1 monotherapy and combination therapy also appeared to have a deleterious effect on the intratumor population of T regulatory cells, which are known to contribute to tumor resistance to immunotherapy (FIG. 5f). To determine whether the anti-tumor effect observed was dependent on the activity of cytotoxic CD8-positive T lymphocytes, combination treatment was repeated in Balb/c mice bearing TUBO tumors in the presence of CD8-blocking antibody. Depletion of CD8 T lymphocytes rescued the anti-tumor activity of the combination treatment (FIG. 5g). Successful splenic depletion of CD8 T-cells in animals receiving CD-8 blockade (FIG. 5h) was confirmed.

Figure 6A:
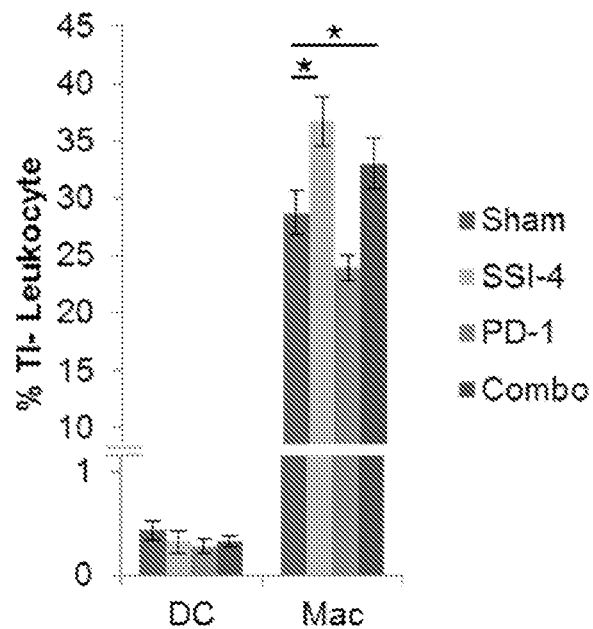
FIG. 6A shows that macrophages are the predominant resident leukocyte in studied tumors, and both SSI-4 and combination therapy increased intratumor infiltration of macrophages by approximately 8% and 5%, respectively.
Figure 6B:
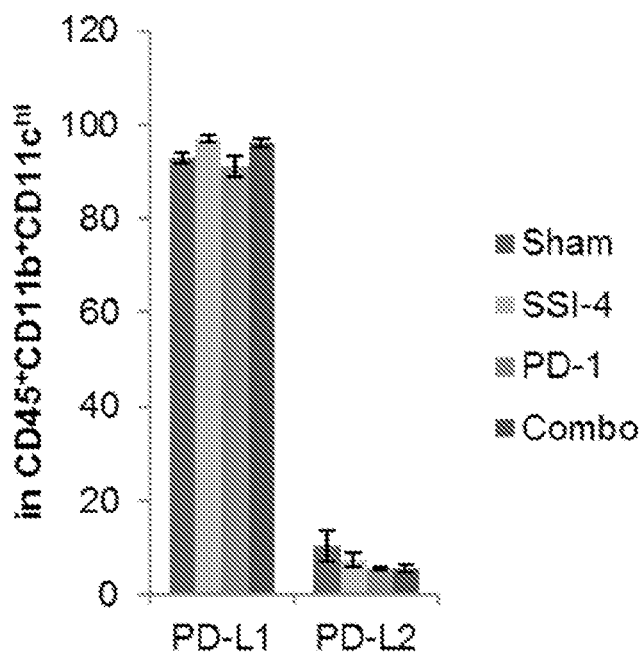
FIG. 6B shows that no significant changes in the protein expression of the checkpoints PD-L1 or PD-L2 were observed in dendritic cells.
Figure 6C:
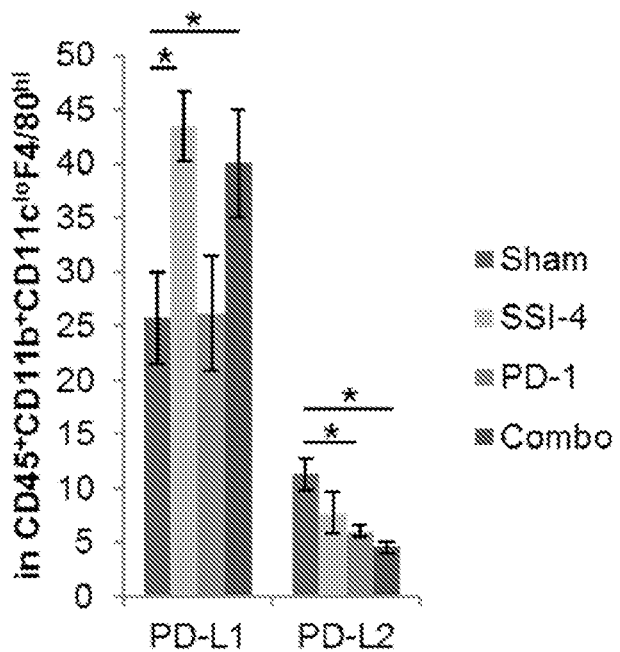
FIG. 6C shows that macrophages showed increased PD-L1 in response to both SSI-4 and combination therapy.
Figure 6D:
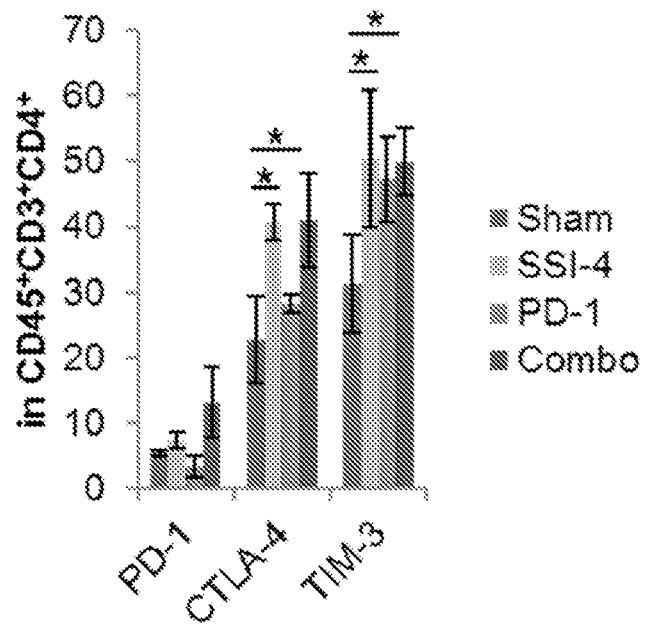
FIGS. 6D-6E show that T lymphocytes demonstrate upregulation of protein expression of various checkpoints in response to therapy, including CTLA-4 and TIM3.
Figure 6E:
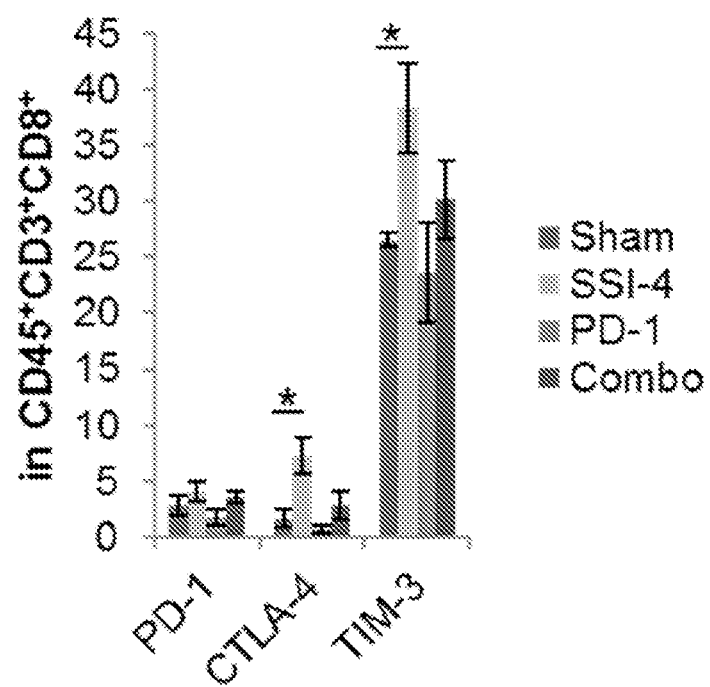
Figure 7:
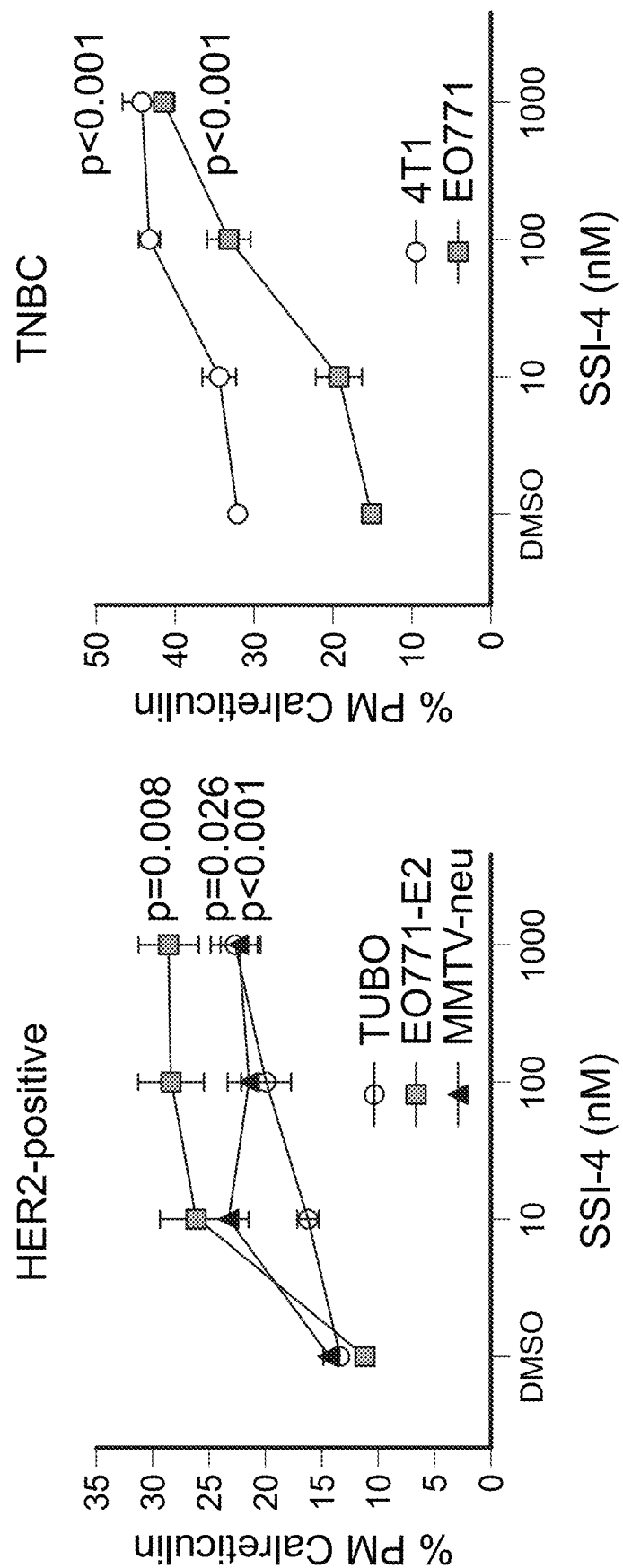
FIG. 7 shows results of flow cytometry on live tumor cells (HER2-positive and TNBC breast cancer) following a 48 hour treatment with SSI-4 (10-1000 nM), demonstrating that SSI-4 induces plasma membrane translocation of calreticulin, a known immunogenic cell death inducer. Significance shown for 1000 nM dose (anova).
Figure 8:
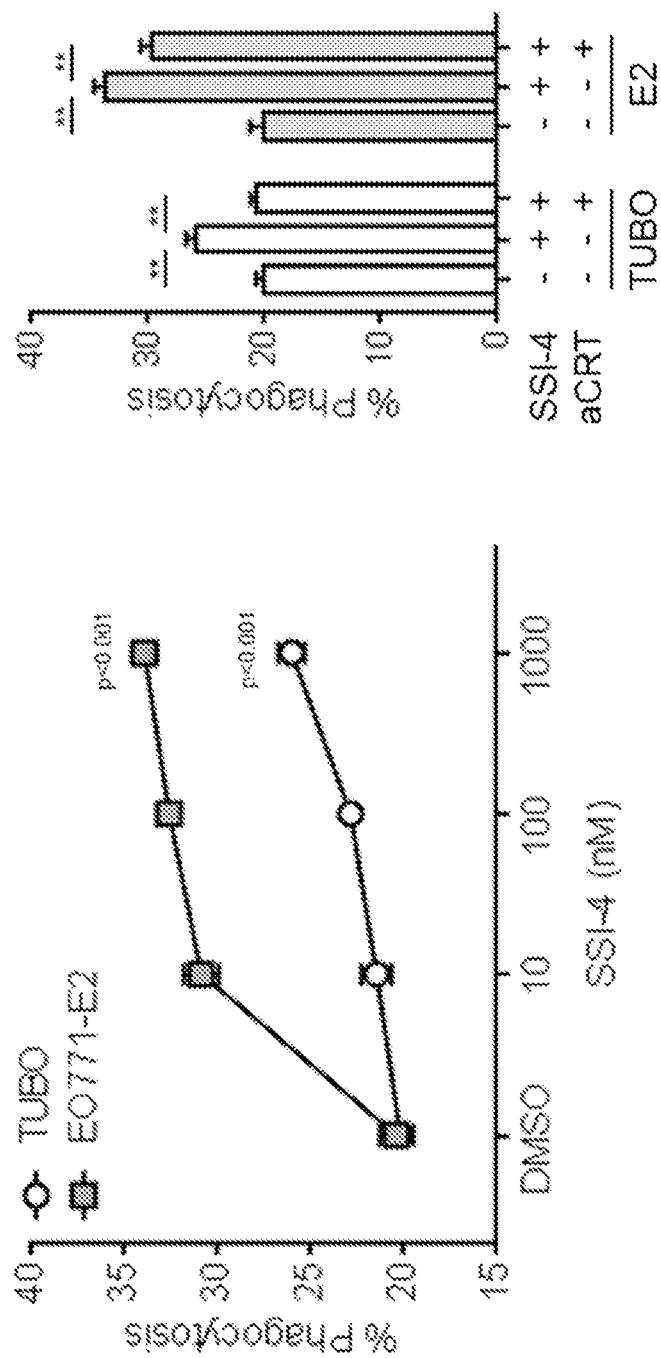
FIG. 8 shows that SSI-4 (1000 nM) induced the highest level of phagocytosis of both TUBO and E0771-E2 HER2-positive breast cancer cells (5 and 13%, respectively), and this effect is reversed in with adjuvant CRT neutralization.
Figure 9:
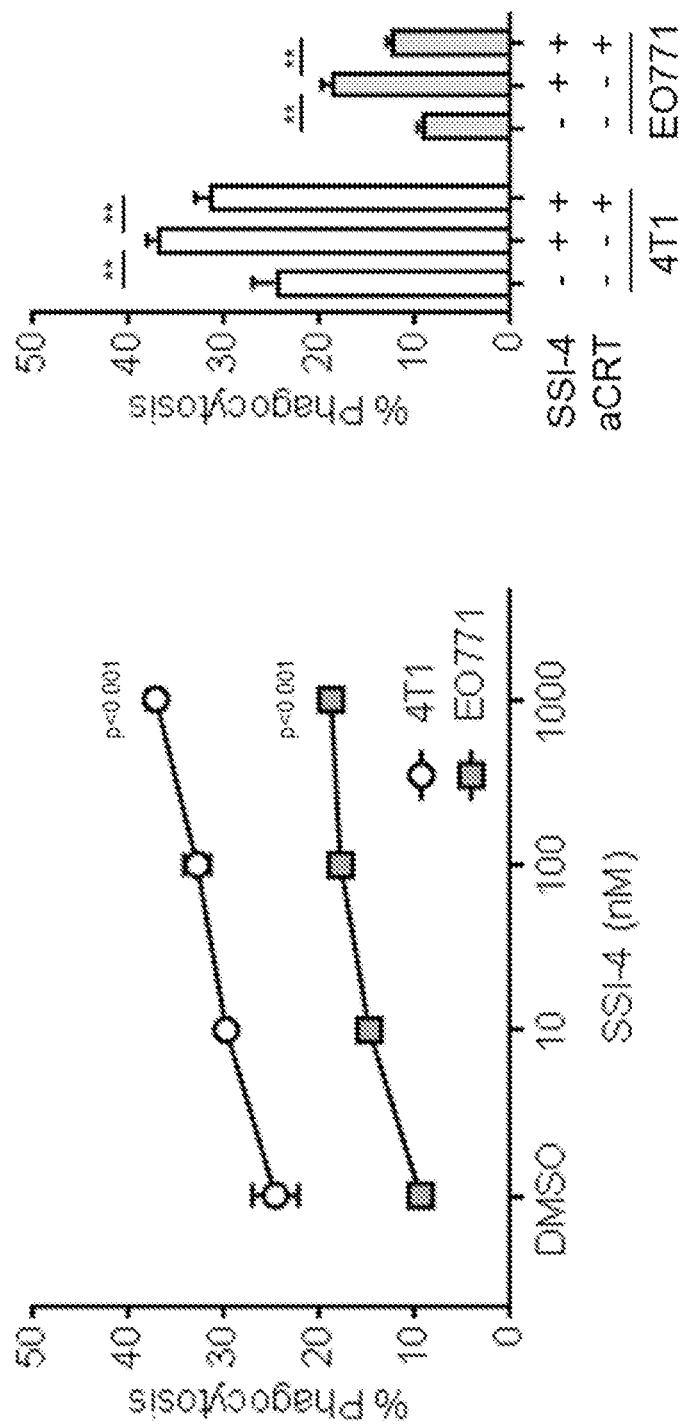
FIG. 9 shows that SSI-4 (1000 nM) induced the highest level of phagocytosis of both 4T1 and E0771 TNBC breast cancer cells (12.5 and 9.4%, respectively), and this effect is reversed in with adjuvant CRT neutralization.
Figure 10:
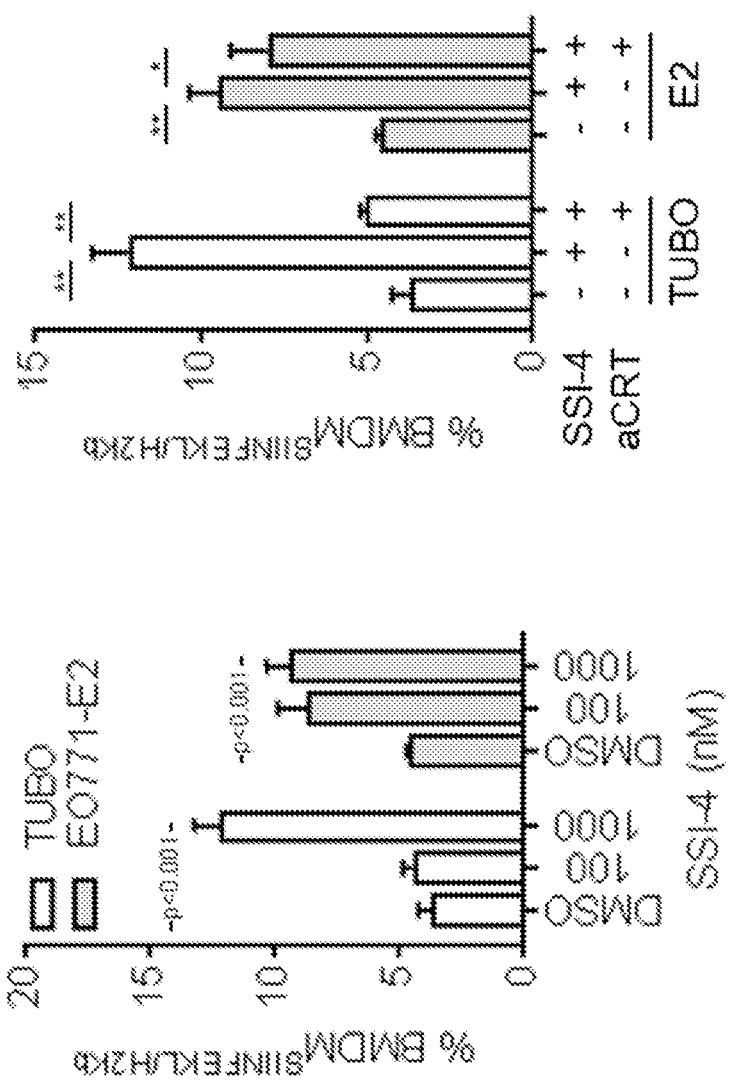
FIG. 10 shows that SSI-4 treatment (1000 nM) significantly enhanced antigen presentation in both TUBO (8.5%) and E0771-E2 (5%) cells, and that this effect was inhibited with adjuvant CRT neutralization.
Figure 11:
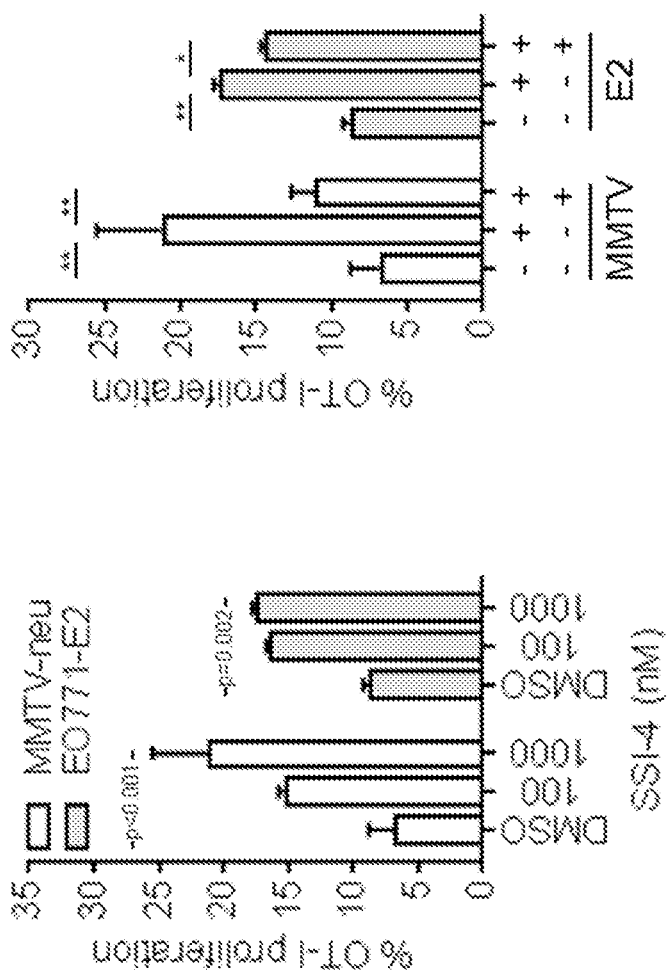
FIG. 11 shows that SSI-4 treatment (1000 nM) significantly enhanced OT-I CD8 T cell proliferation in both E0771-E2 and MMTV-neu cells, and that this effect was inhibited with adjuvant CRT neutralization.
Figure 12:
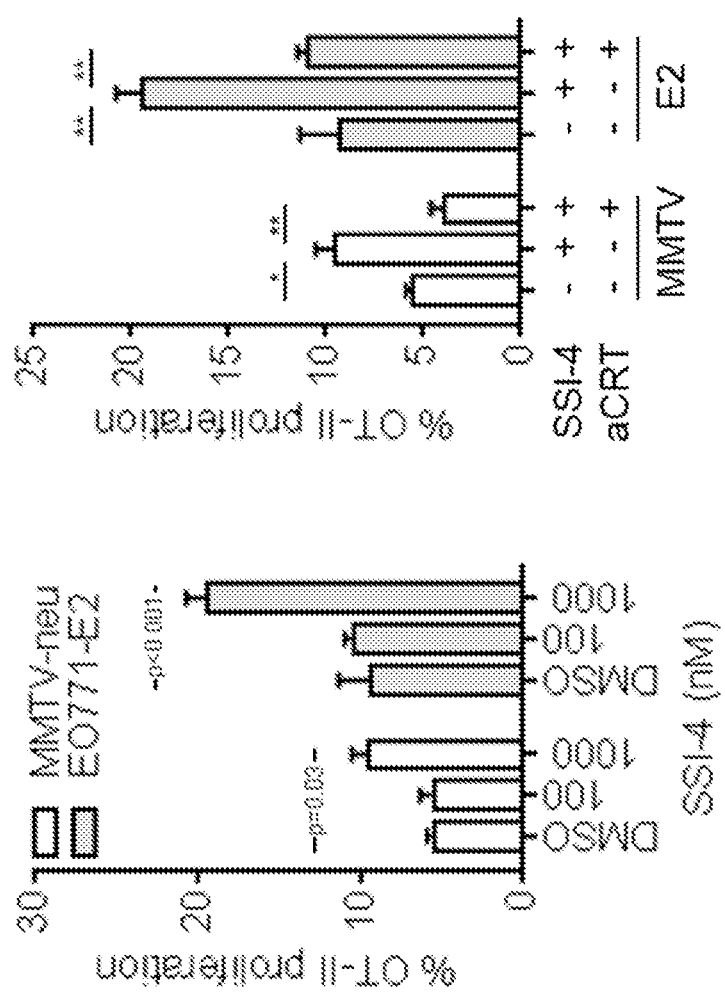
FIG. 12 shows that SSI-4 treatment (1000 nM) significantly enhanced OT-II CD4 T cell proliferation in both E0771-E2 and MMTV-neu cells, and that this effect was inhibited with adjuvant CRT neutralization.
Figure 13:
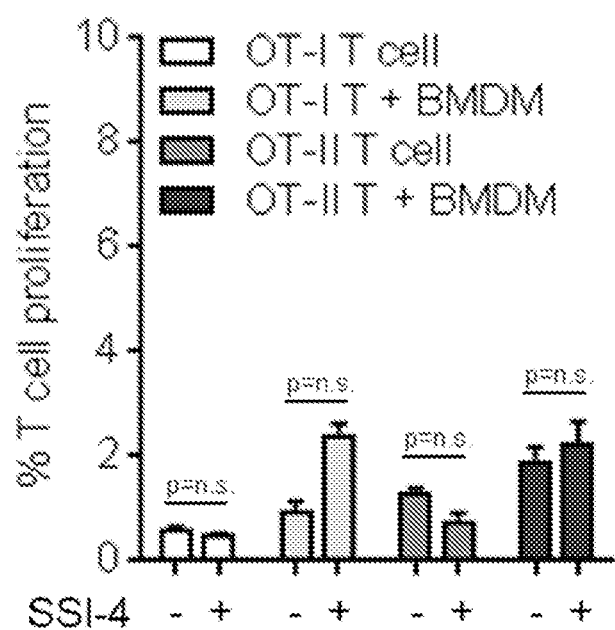
FIG. 13 T cell proliferation in FIG. 2D-F was dependent on the co-presence of macrophages (BMDM), T cells (T), and tumor cells as SSI-4 treated T cells alone and T cells plus macrophages could not induce T cell proliferation.
Figure 14:
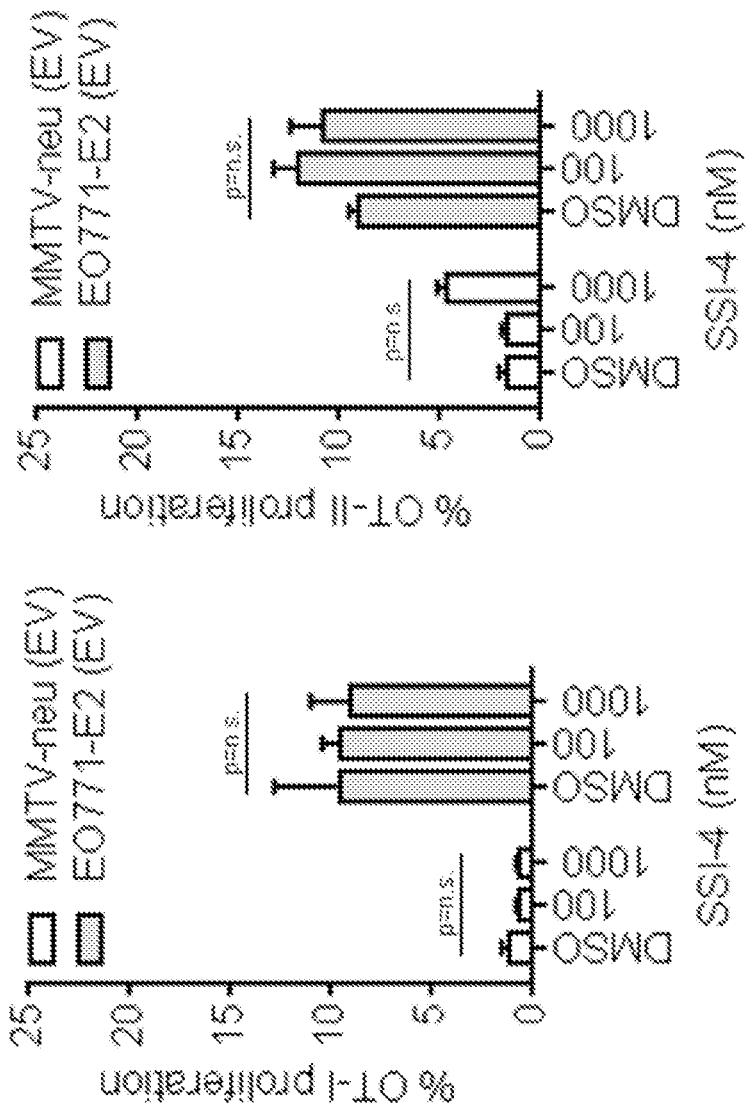
FIG. 14 shows T cell proliferation in response to SSI-4 treatment in FIG. 2D-E is antigen-dependent, as expression of cOVA antigen by tumor cells was required, as those bearing empty vector (EV) could not similarly stimulate T cell proliferation.
Figure 15:
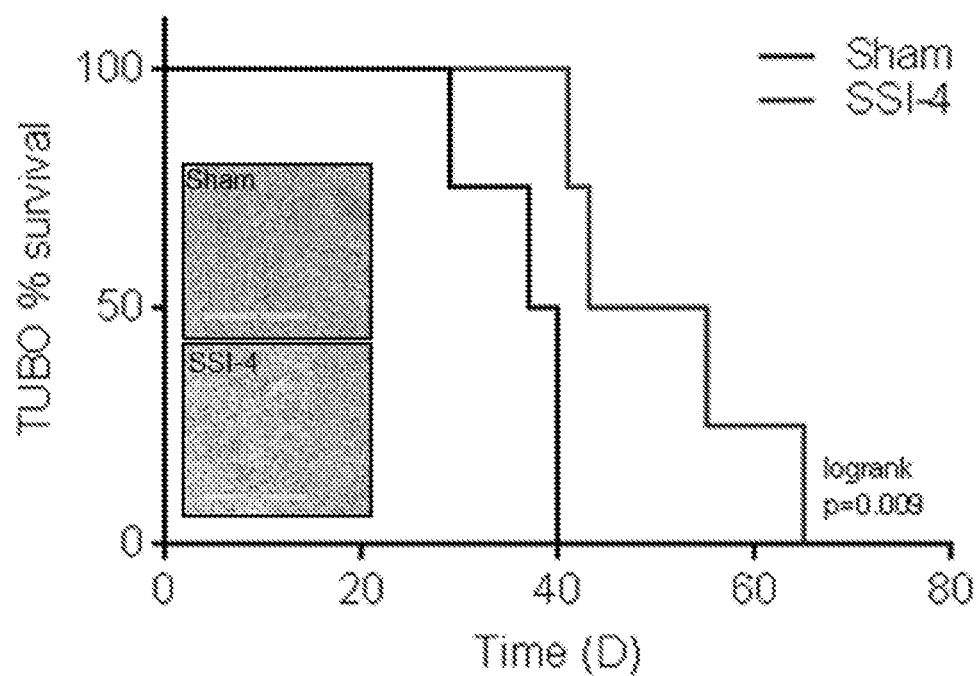
FIG. 15 shows an appreciable increase in overall survival in SSI-4 treated mice. H&E staining of tumor sections did not reveal conspicuous changes in overall tissue morphology between sham and SSI-4 treatment groups.
Figure 16:
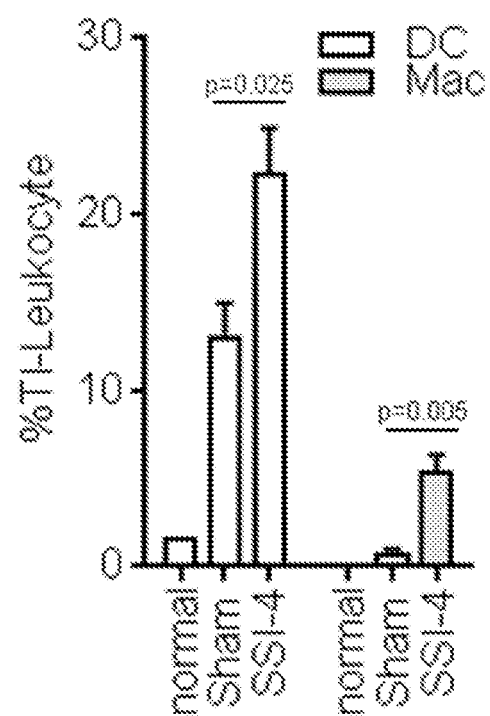
FIG. 16 shows a significant increase in the number of intra-tumor dendritic cells within SSI-4 treated tumors as compared to both control treated tumors, and normal mammary tissue from non-tumor bearing mice.
Figure 17:
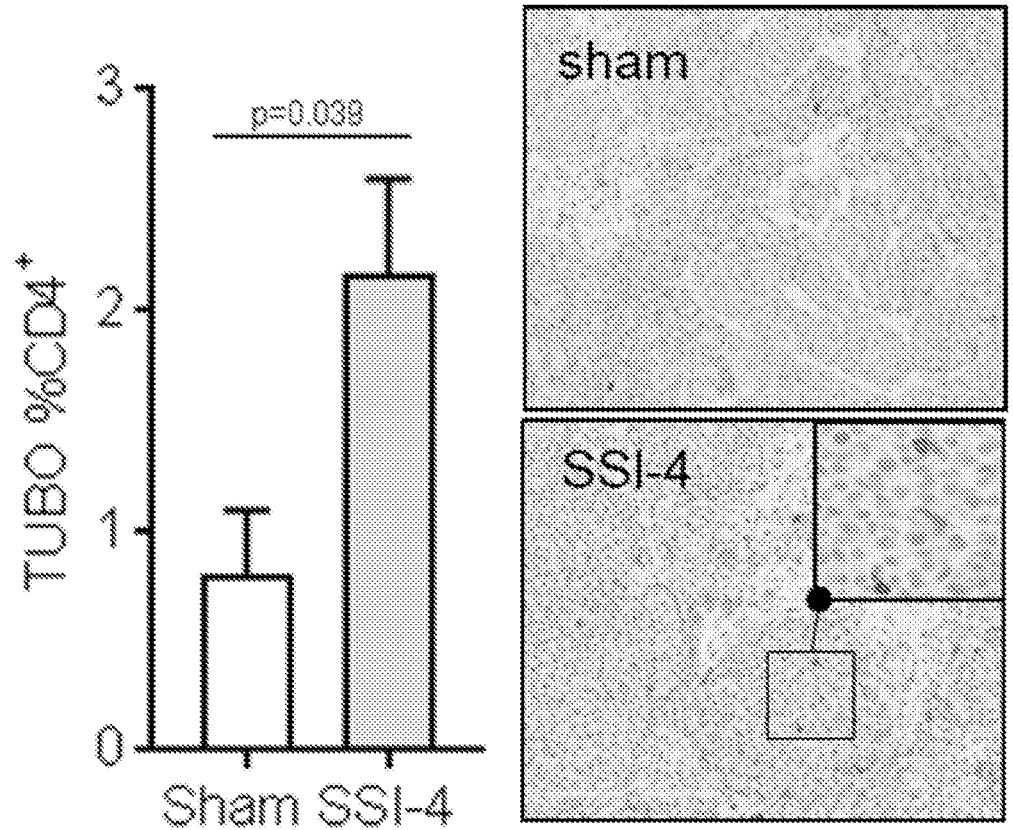
FIG. 17 shows an increase in the number of CD4+ tumor-infiltrating populations in SSI-4 treated tumors.
Figure 18:
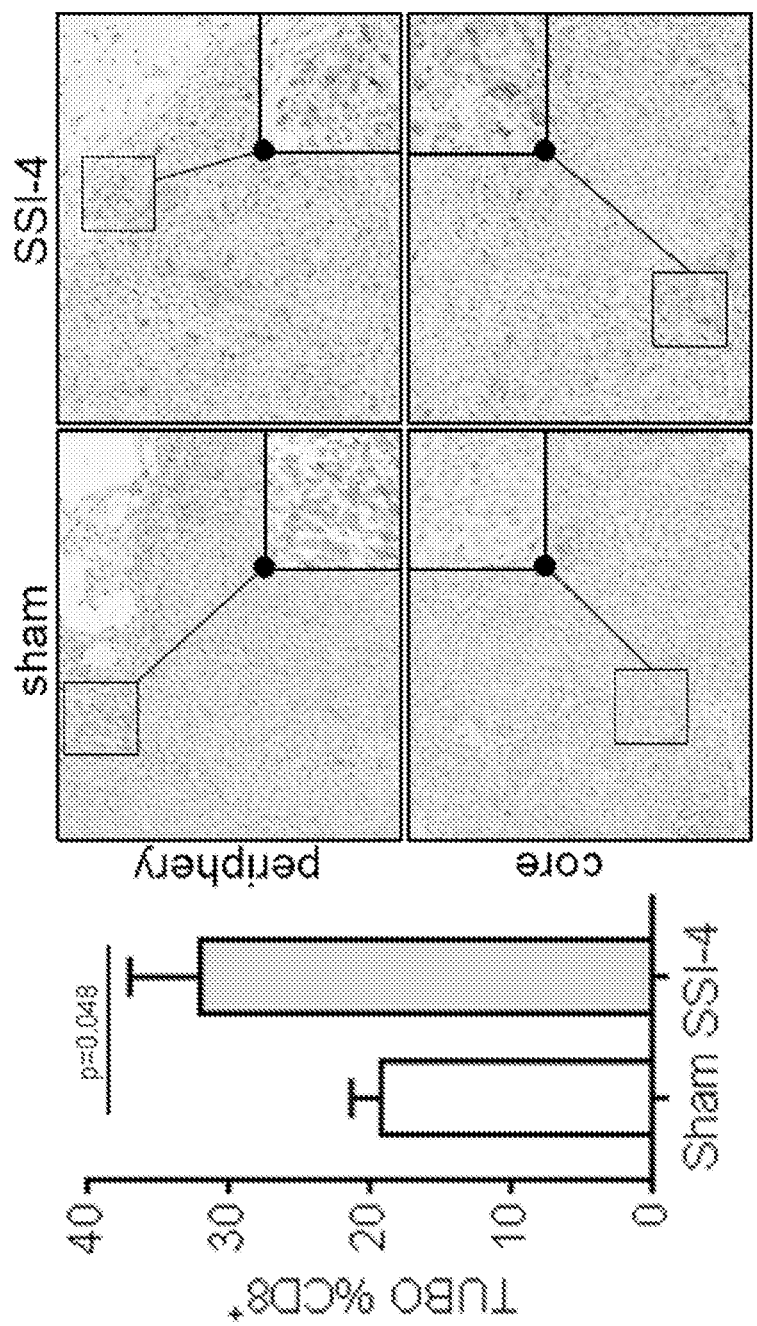
FIG. 18 shows an increase in the number of CD8+ tumor-infiltrating populations in SSI-4 treated tumors. Of note, CD8 T cells were present both peripherally and centrally in SSI-4 treated tumors, whereas those seen in control tumors were predominantly peripheral.
Figure 19:
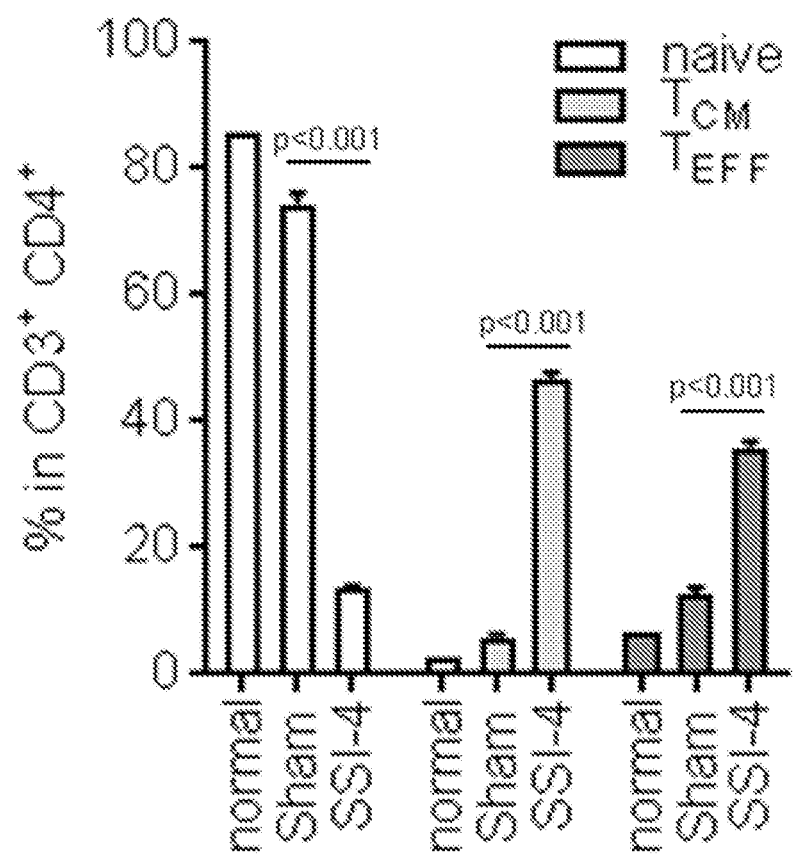
FIG. 19 shows that SSI-4 treatment produced a robust induction of splenic memory ($T_{CM}$) and effector ($T_{EFF}$) T-cells among CD4 positive T cell populations.
Figure 20:
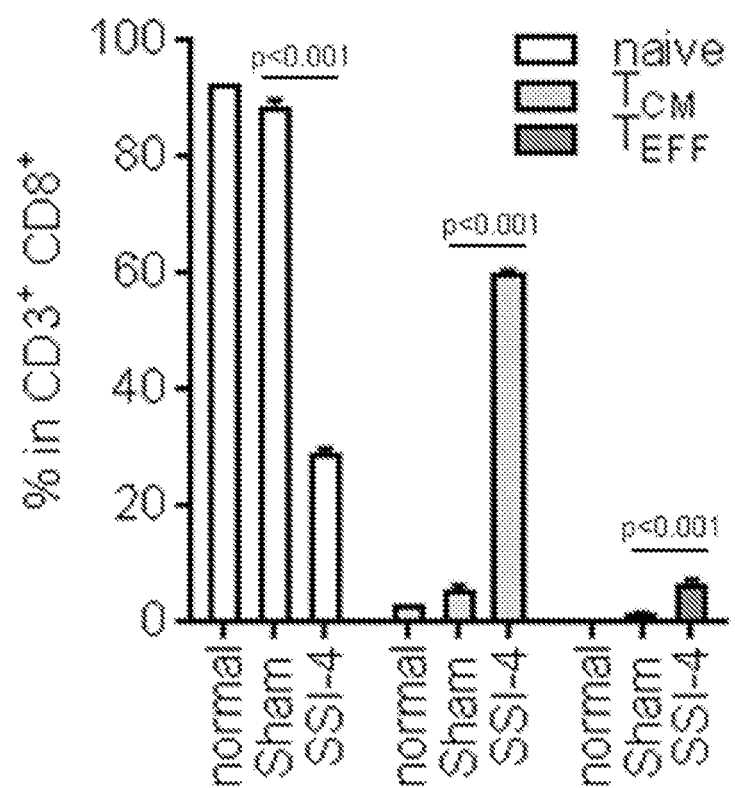
FIG. 20 shows that SSI-4 treatment produced a robust induction of splenic memory and effector T-cells among CD8 positive T cell populations.
Figure 21:
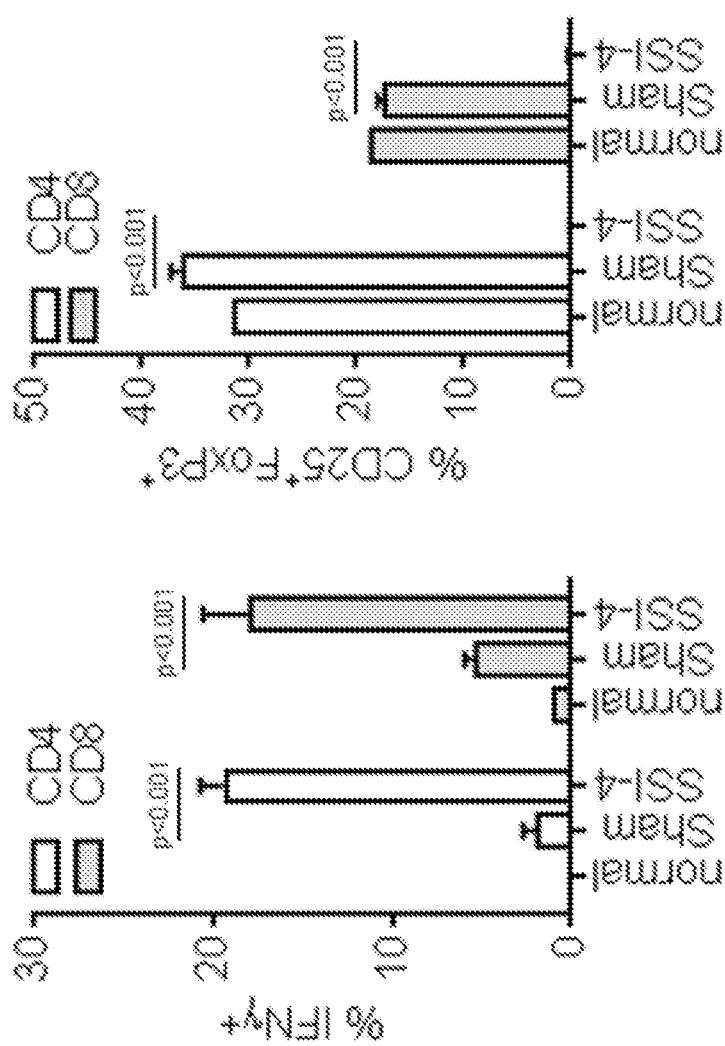
FIG. 21 shows that effector CD4 and CD8 T lymphocytes identified by IFNγ was markedly increased in both CD4 and CD8+ T cell populations from SSI-4 treated TUBO tumors. SSI-4 also significantly reduced the number of intra-tumor CD4+ T regulatory cells identified by dual CD25 and FoxP3 expression.
Figure 22:
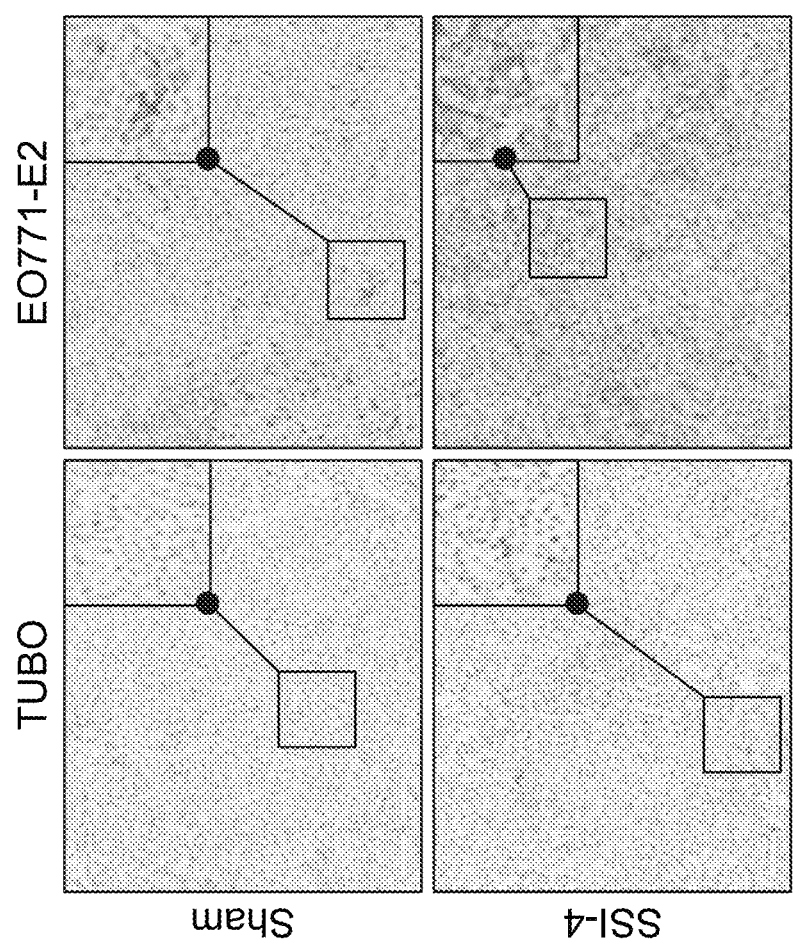
FIG. 22 shows that SSI-4 treatment induces programmed death ligand-1 (PD-L1) 5 expression in both TUBO and EO771-E2 HER2-positive breast tumor bearing mice.
Figure 22:
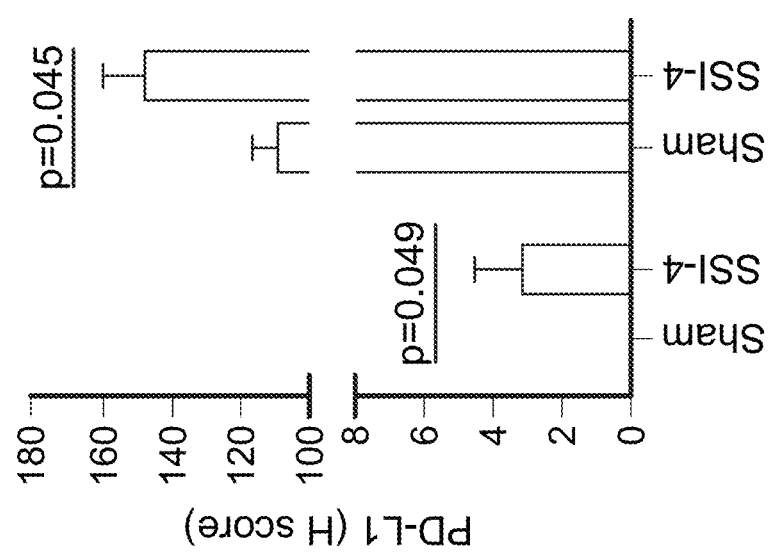
Figure 23A:
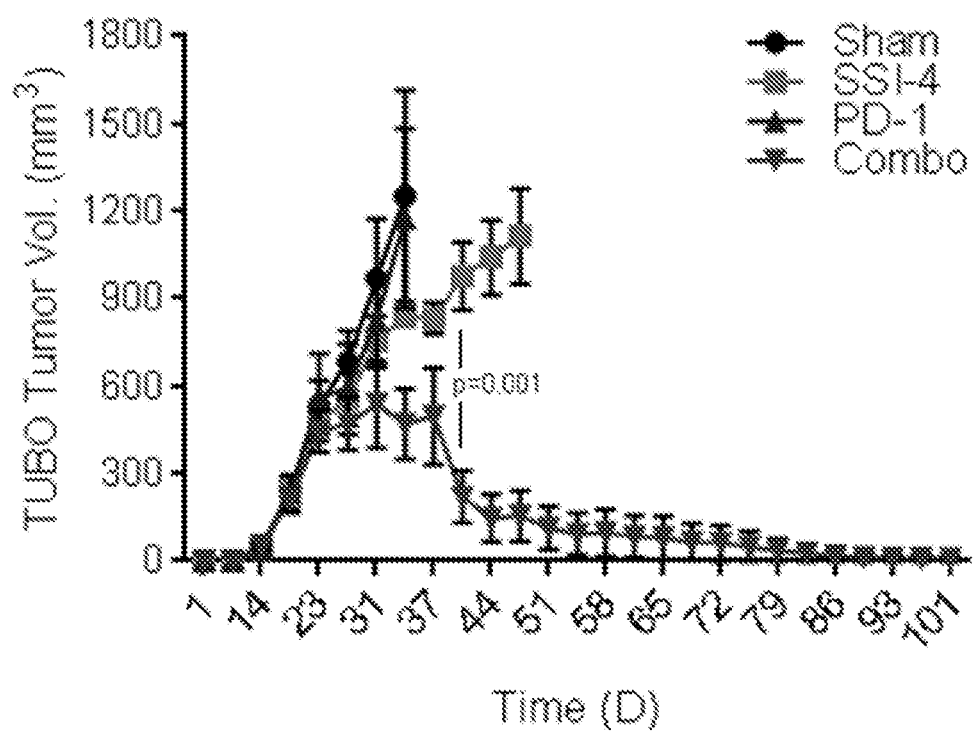
FIGS. 23A-23B show that TUBO HER2-positive tumors do not respond to monotherapeutic PD1 blockade; combination of PD-1 blockade with SSI-4 produced a more durable anti-tumor response; Complete tumor regression and durable survival achieved in 83% of combination treated animals, where all animals in other treatment groups succumbed to tumor burden. SSI-4 monotherapy treated animals demonstrated improved median survival of approximately 37% and 35% as compared to sham and PD-1 monotherapy treated groups, respectively.
Figure 23B:
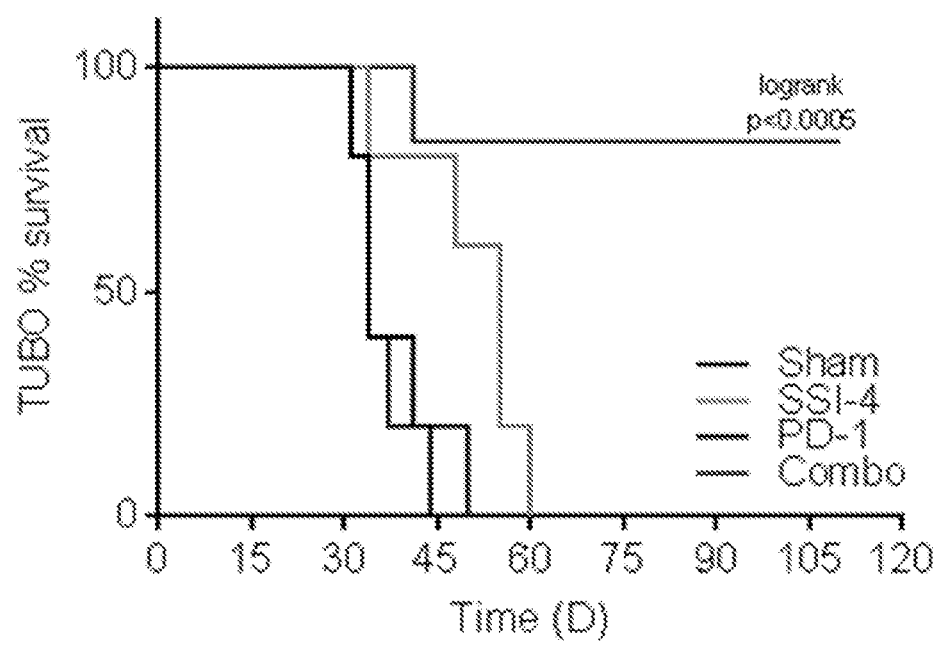
Figure 23C:
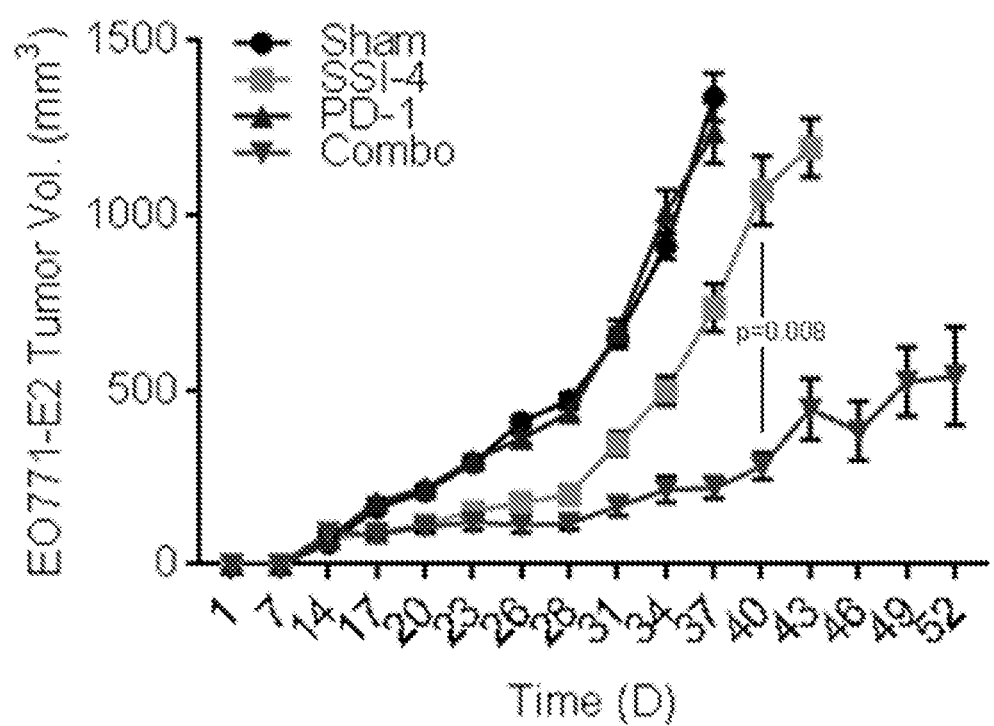
FIGS. 23C-23D show that EO771-E2 HER2-positive tumors do not respond to monotherapeutic PD1 blockade; combination of PD-1 blockade with SSI-4 produced a more durable anti-tumor response; complete tumor regression and durable survival achieved in 28% of combination treated animals, where all animals in other treatment groups succumbed to tumor burden. SSI-4 monotherapy treated animals demonstrated improved median survival of approximately 22% and 20% as compared to sham and PD-1 monotherapy treated groups, respectively.
Figure 23D:
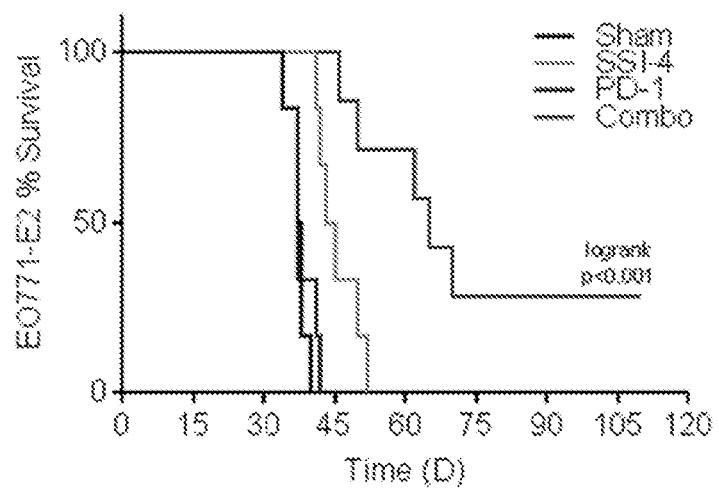
Figure 23E:
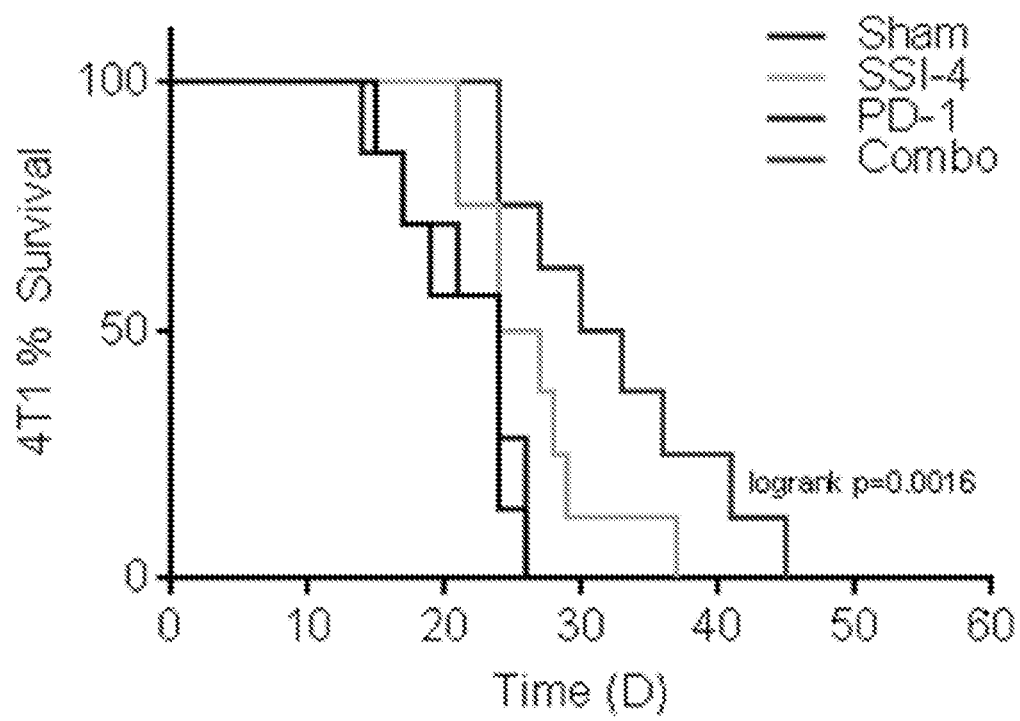
FIGS. 23E-23F show that 4T1 TNBC tumors do not respond to monotherapeutic PD1 blockade; combination of PD-1 blockade with SSI-4 produced a statistically significant anti-tumor response; While no treatment groups achieved complete tumor regression, combination treated animals demonstrated improved median survival of approximately 75%, 104%, and 40.8% as compared to sham, PD-1, and SSI-4 monotherapy treated groups, respectively.
Figure 23F:
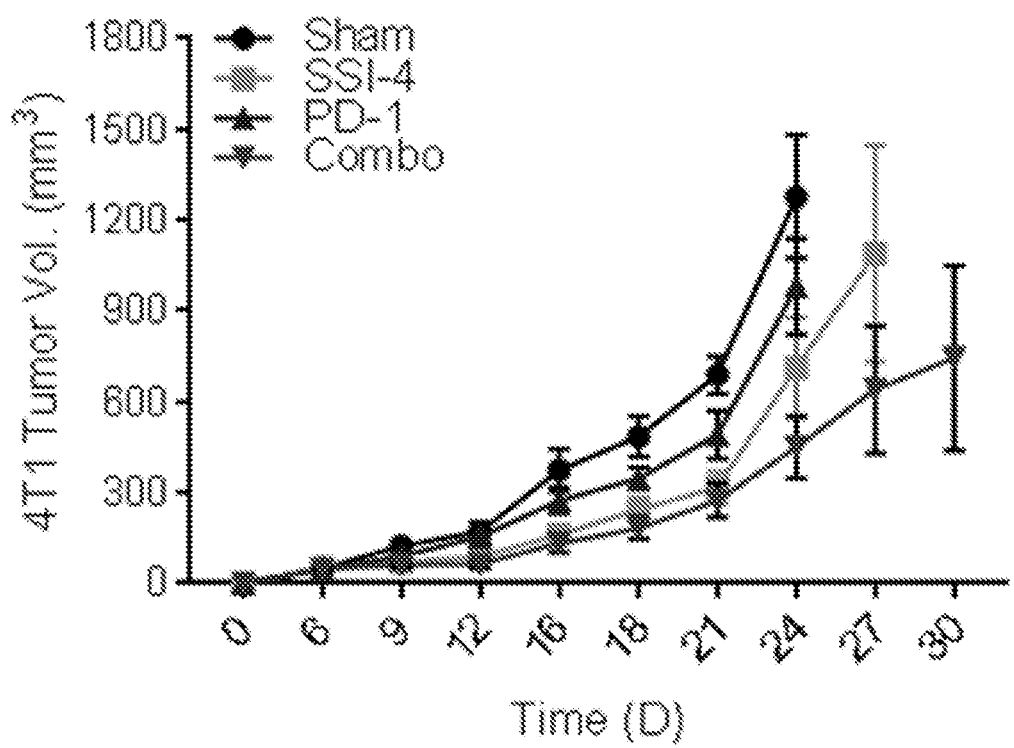
Figure 23G:
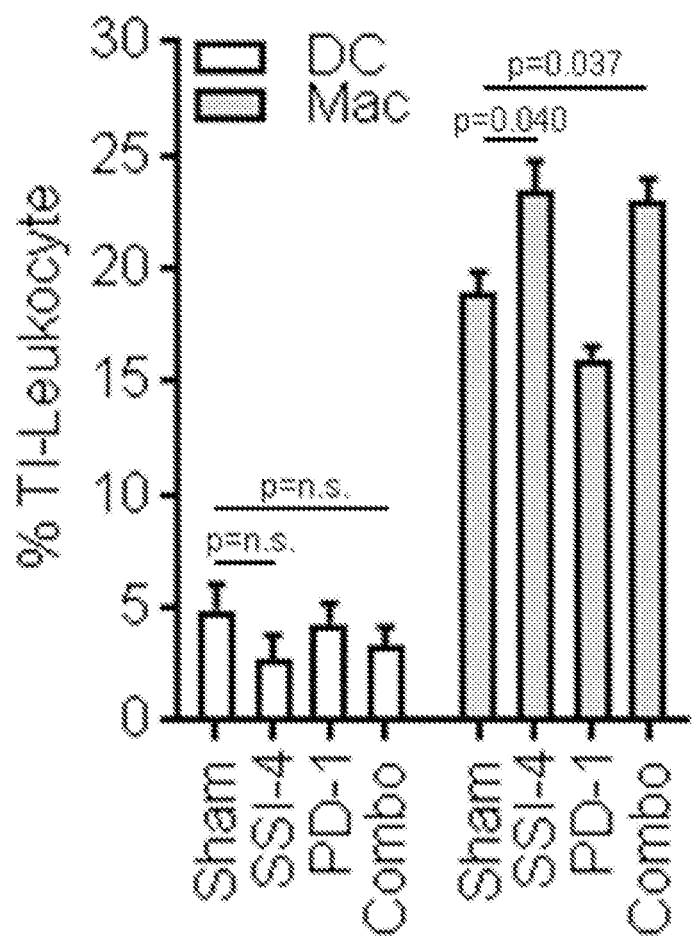
FIG. 23G shows that SSI-4 monotherapy and combination therapy increased the number of tumor infiltrating macrophages in EO771-E2 HER2-positive tumors.
Figure 23H:
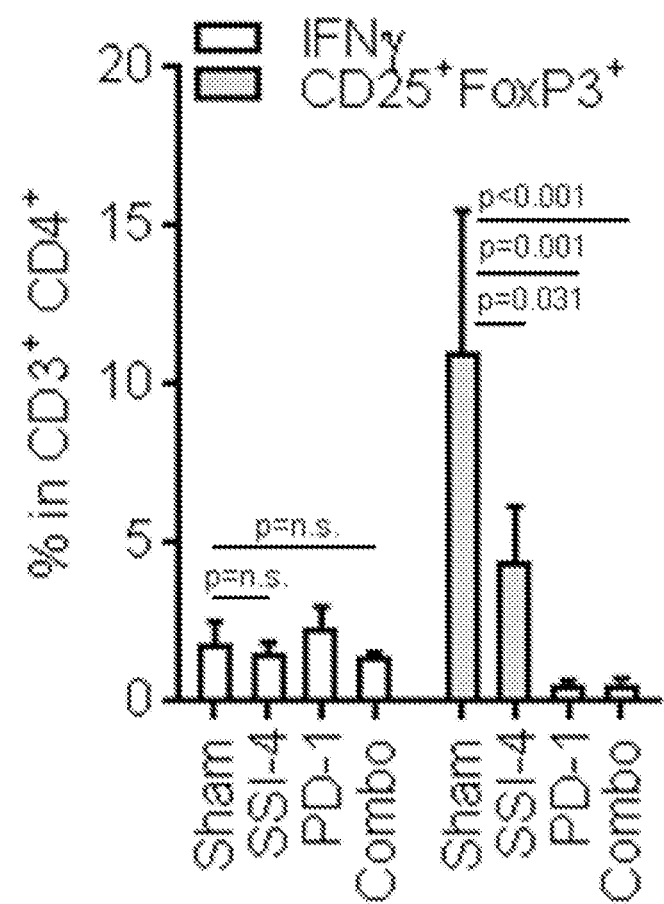
FIGS. 23H-23I shows that SSI-4, PD-1 monotherapy, and combination therapy had a deleterious effect on the intratumor population of CD4-positive T regulatory cells; and SSI-4 monotherapy and combination therapy increased the number of cytotoxic CD8+ T cells in EO771-E2 tumors.
Figure 23I:
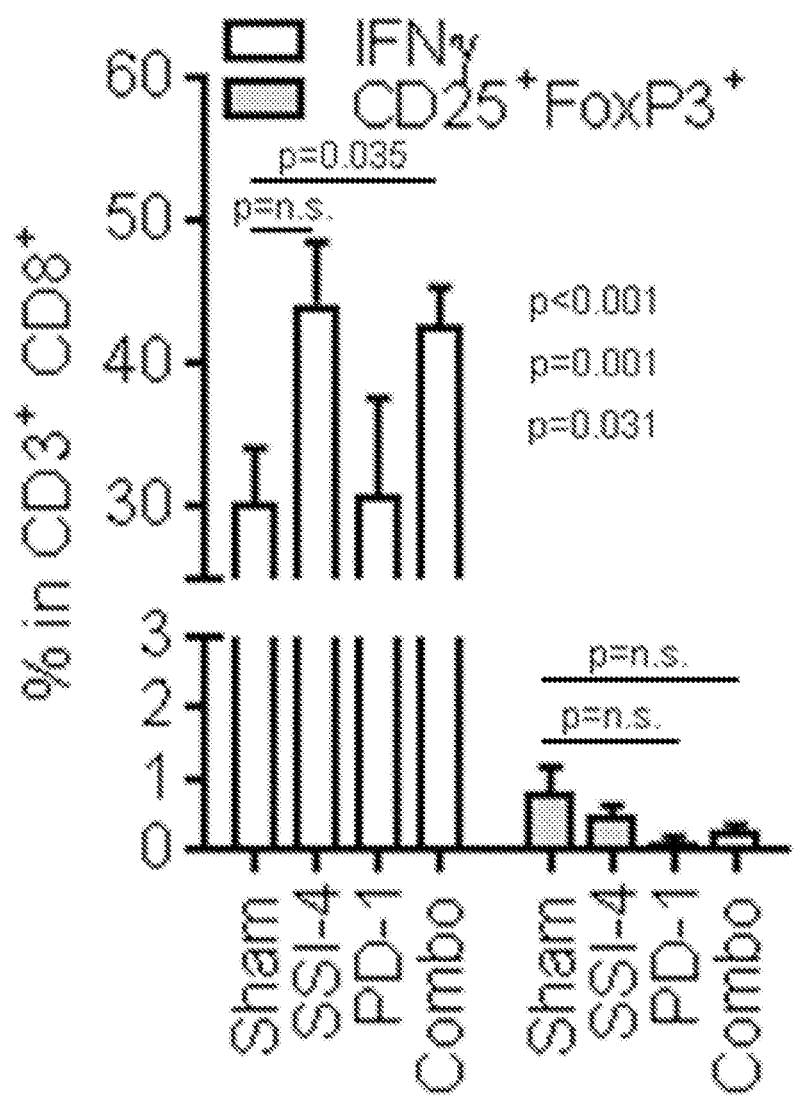
Figure 24A:
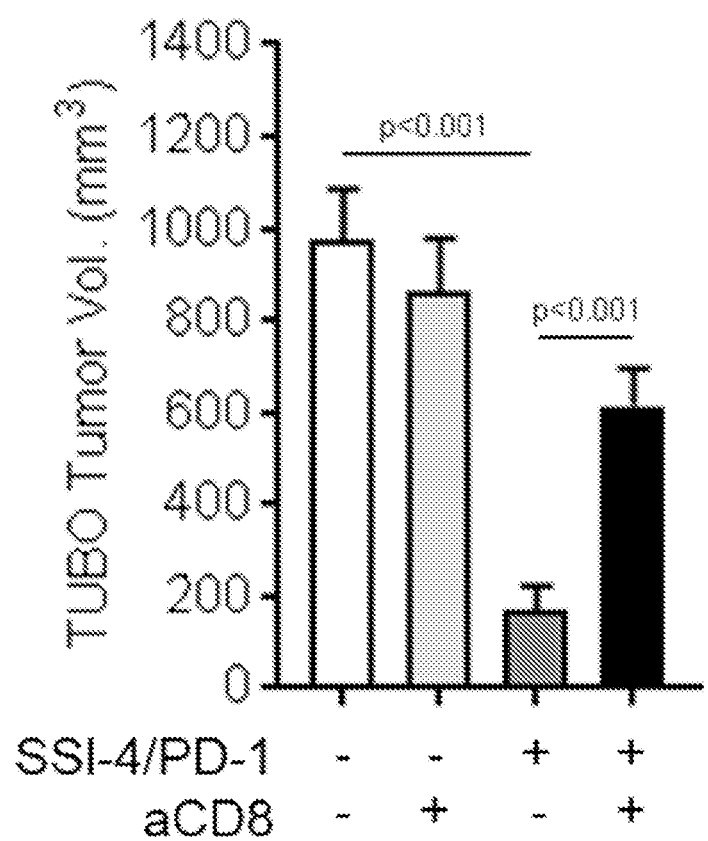
FIGS. 24A-24B shows that depletion of CD8 T lymphocytes rescued the anti-tumor activity of the combination treatment in both TUBO and EO771-E2 HER2-positive tumors.
Figure 24B:
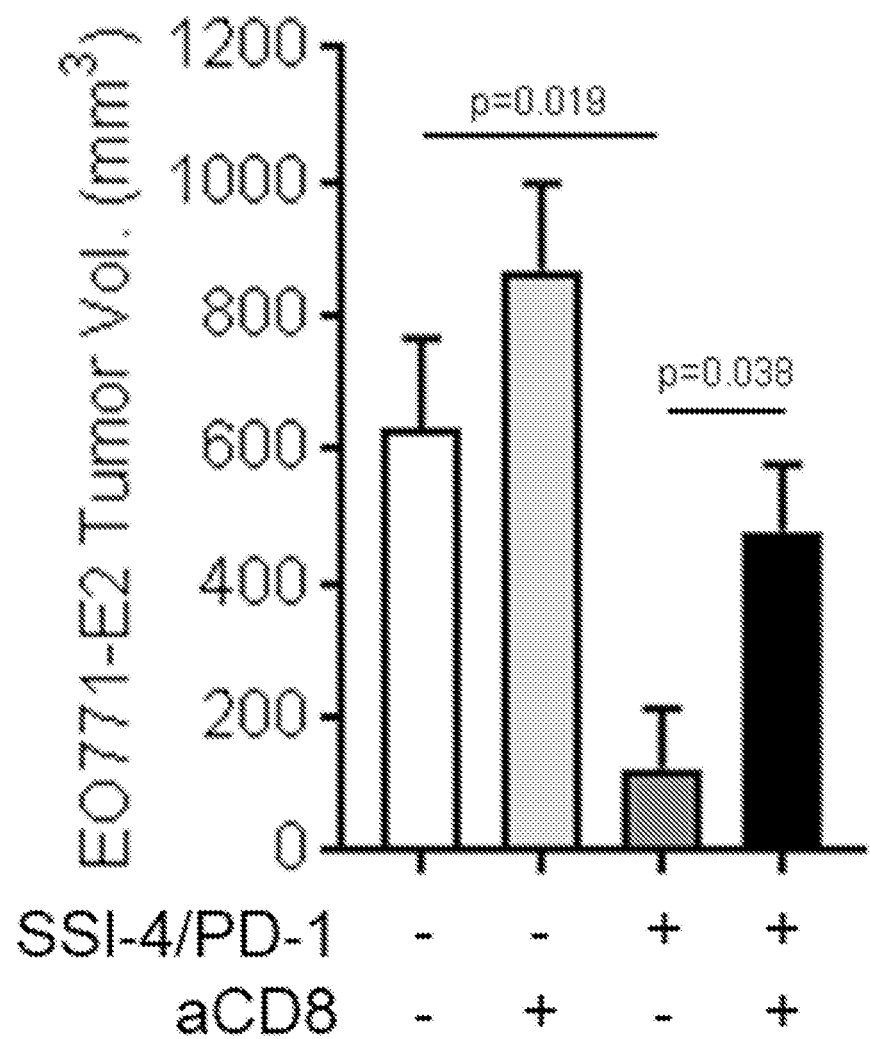
Figure 25:
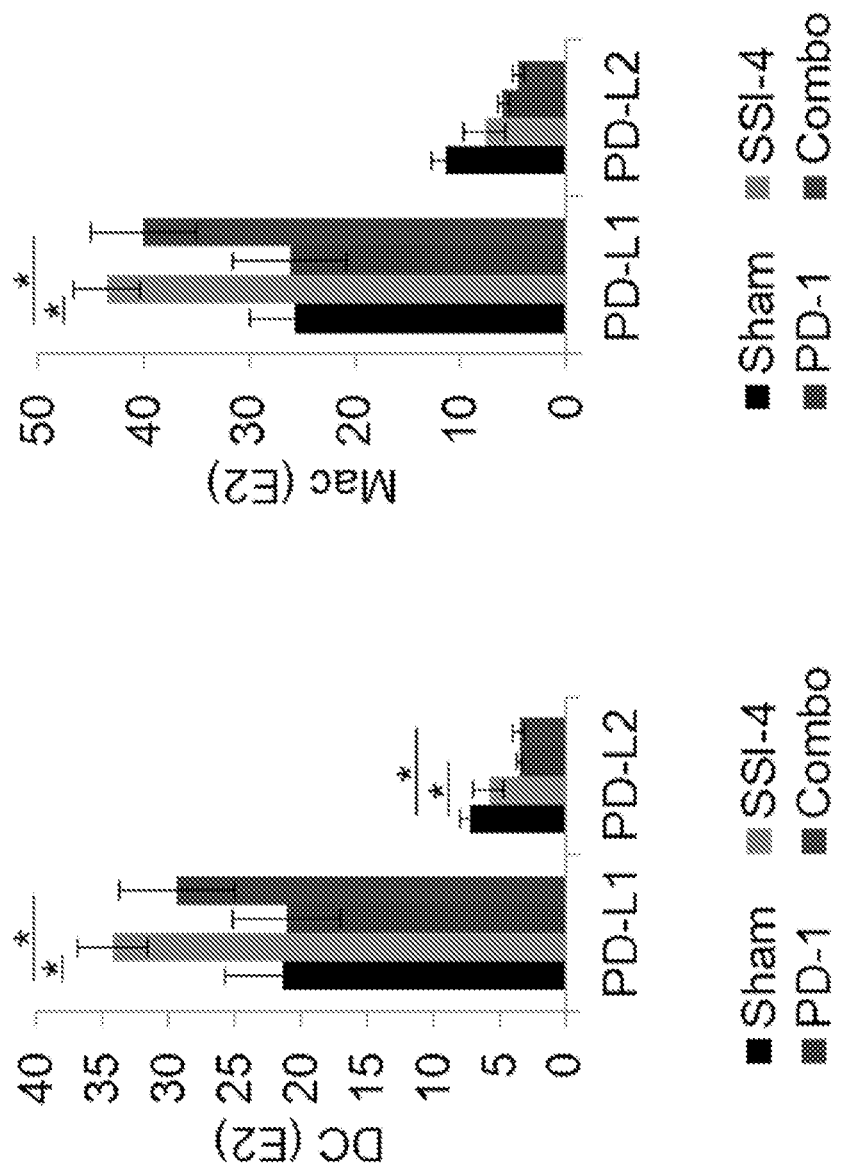
FIG. 25 shows that significant changes in the protein expression of the checkpoint PD-L1 but not PD-L2 were observed in tumor-infiltrating dendritic and macrophage cells in EO771-E2 in response to each SSI-4 monotherapy and combination therapy.
Figure 26:
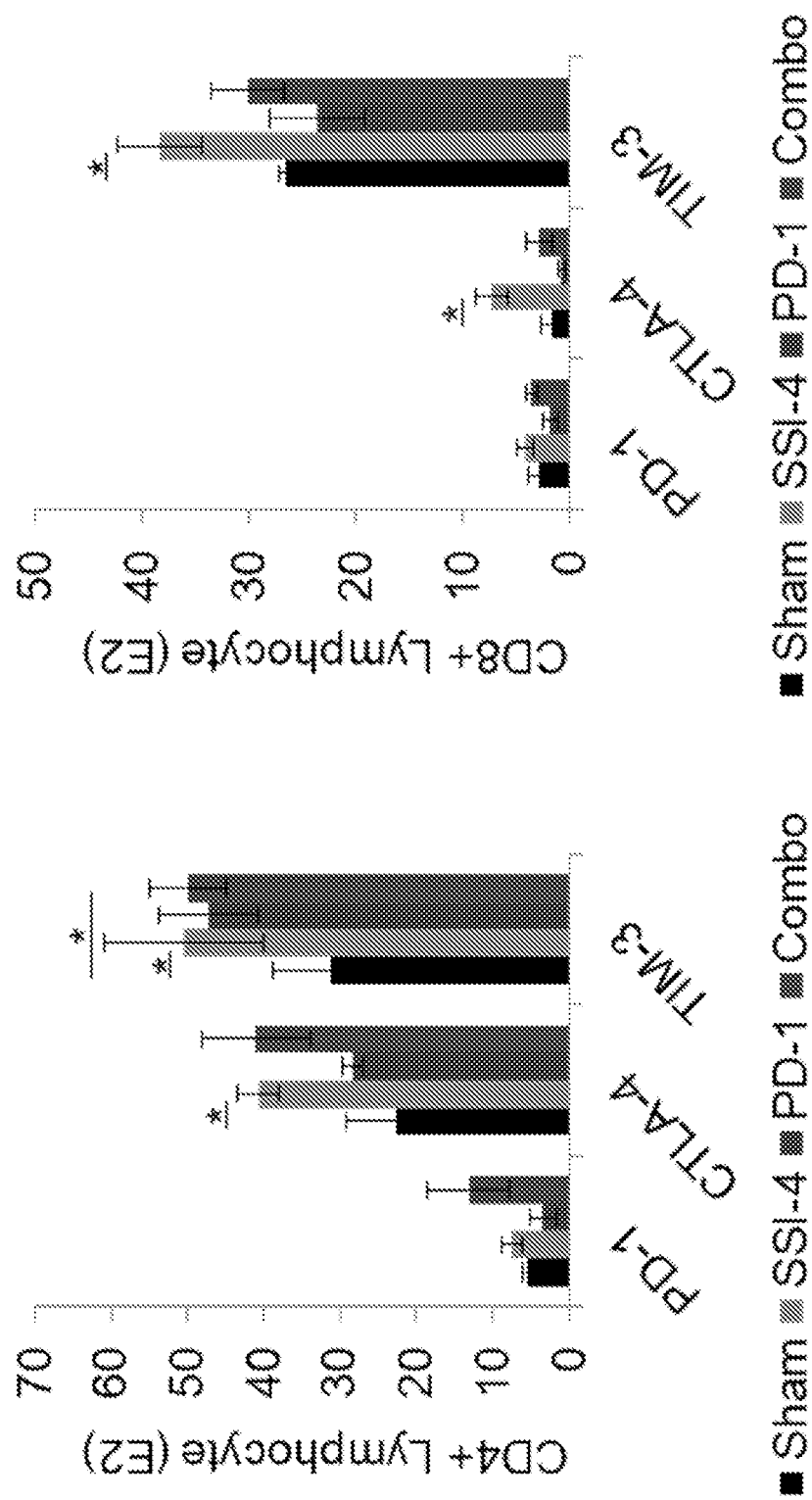
FIG. 26 shows that each CD4+ and CD8+ T lymphocytes demonstrate upregulation of protein expression of various checkpoints in response to therapy, including CTLA-4 and TIM3.

To better understand mechanisms of drug resistance to combination therapy, EO771-E2 tumor tissue was harvested from treated mice, and the expression level of known checkpoint proteins was evaluated on intratumor dendritic cells, macrophages, and T lymphocytes. Results show that macrophages are the predominant resident leukocyte in these tumors, where dendritic cells represent less than 1% of all CD45% cells (FIG. 6a). A significant influx of macrophages into the tumor was observed in response to either SSI-4 or combination therapy (FIG. 6a). No significant changes in the protein expression of the checkpoints PD-L1 or PD-L2 were observed in dendritic cells (FIG. 6b). Macrophages showed increased PD-L1 in response to both SSI-4 and combination therapy (FIG. 6c). Both CD4 and CD8 positive T lymphocytes demonstrate upregulation of protein expression of various checkpoints in response to therapy, including CTLA-4 and TIM3 (FIG. 6d-e). These findings suggest that tumors respond to SSI-4 and combination therapy by upregulating other known checkpoints in an effort to mount tumor-resistance. Combination therapy with SSI-4 that includes a cocktail of checkpoint inhibitors such as anti-PD-L1, anti-CTLA4, and/or anti-TIM3 may provide a more durable anti-tumor response.

FIGS. 5G-5H, 6A-6E:

Tumor-infiltrating (TI) leukocytes and lymphocytes were assessed by multicolor flow cytometry on dissociated treated tumor tissue extracted from E0771-E2 bearing mice on day 27 of the study. 6A: The % of dendritic cells (DC) vs. macrophages (mac) that make up TI-Leukocytes was determined, and demonstrate that mac are the predominant TI-leuk in these tumors. 6B: The expression of the checkpoints PD-L1 and PD-L2 on either DC or Mac in response to therapy demonstrate that SSI-4 (and combinatorial therapy) strongly induce PD-L1 expression on macrophages. The expression of the checkpoints PD-1, CTLA-4, and TIM-3 was assessed in either 6D: CD4-expressing or 6E: CD8-expressing T lymphocytes, and show upregulation of both CTLA-4 and TIM-3 in response to SSI-4 and/or combination therapy. 5G: To determine whether anti-tumor activity of SSI-4/PD-1 combination therapy is dependent on cytotoxic CD8 T lymphocyte activity, CD8 depletion studies were performed in mice receiving either placebo or combination therapy. Combination treated mice bearing E0771-E2 tumors demonstrated significant reduction in tumor burden as compared to placebo mice, and this was reversed in the presence of CD8 depletion. 5H: Flow cytometric analysis was performed on splenic T cells isolated from animals in (5G), and confirm successful depletion of CD8 T cells within animals receiving CD8 blockade.

Without being bound by a particular theory, it is believed that using several poorly immunogenic models of orthotopic HER2 breast cancer, the examples describes herein show that SCD1 inhibitors such as SSI-4 enhance tumor antigen presenting cell (APC) recruitment and maturation, as well as T cell priming both in vitro and in vivo. In monotherapy treated immunocompetent murine models, SCD1 inhibitors such as SSI-4 led to a significant reduction in tumor burden and increase in survival as compared to controls. Tissue analysis revealed tumor infiltration of effector T lymphocytes, and reduction of anti-inflammatory T regulatory (Treg) cells, redolent of a T-cell inflamed phenotype. The results further show that SCD1 inhibitors such as SSI-4 are able to sensitize resistant tumors to programmed death-1 (PD-1) inhibition, resulting in reduced tumor burden and significantly prolonged survival. These findings demonstrate that SCD1 inhibitors such as SSI-4 modulate tumor immunity and synergize with the checkpoint inhibitors such as PD-1 blockers.

OTHER EMBODIMENTS

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A method of treating cancer in a subject, the method comprising administering to the subject a therapeutically effective amount of a compound of formula:

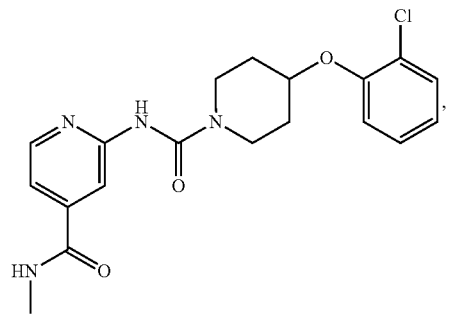 [SMILES: CNC(=O)c1ccnc(NC(=O)N2CCC(Oc3ccccc3Cl)CC2)c1]

or a pharmaceutically acceptable salt thereof, and a therapeutically effective amount of a checkpoint inhibitor selected from an antibody of cytotoxic T-lymphocyte-associated protein-4 (CTLA-4) and an antibody of T-cell immunoglobulin and mucin-domain containing-3 (TIM-3).

2. The method of claim 1, wherein the checkpoint inhibitor is selected from ipilimumab and TSR-022.

3. The method of claim 1, wherein the compound, or a pharmaceutically acceptable salt thereof, is administered in an amount from about 200 mg/kg to about 250 mg/kg; and the checkpoint inhibitor is administered in an amount from about 1 mg/kg to about 15 mg/kg.

4. The method of claim 1, wherein the cancer is selected from the group consisting of: a kidney cancer, a liver cancer, a breast cancer, a lung cancer, a pancreatic cancer, a bladder cancer, a colon cancer, a melanoma, a thyroid cancer, an ovarian cancer, and a prostate cancer.

5. The method of claim 1, wherein the compound, or a pharmaceutically acceptable salt thereof, and the checkpoint inhibitor are administered concurrently.

6. The method of claim 1, wherein the compound, or a pharmaceutically acceptable salt thereof, and the checkpoint inhibitor are administered sequentially.

7. The method of claim 1, wherein the checkpoint inhibitor is an antibody of cytotoxic T-lymphocyte-associated protein-4 (CTLA-4).

8. The method of claim 1, wherein the checkpoint inhibitor is an antibody of T-cell immunoglobulin and mucin-domain containing-3 (TIM-3).

9. The method of claim 1, wherein the checkpoint inhibitor is ipilimumab.

10. The method of claim 1, wherein the checkpoint inhibitor is TSR-022.

* * * * *